(12) United States Patent
Barman et al.

(10) Patent No.: US 9,662,047 B2
(45) Date of Patent: May 30, 2017

(54) PORTABLE RAMAN DIAGNOSTIC SYSTEM

(75) Inventors: Ishan Barman, Boston, MA (US); Narahara Chari Dingari, Somerville, MA (US); Ramachandra Dasari, Shererville, IN (US); Michael Feld, Jamaica Plain, MA (US); Jonathan Feld, legal representative, Somerville, MA (US); David Feld, legal representative, Newark, CA (US); Alison Hearn, legal representative, Jamaica Plain, MA (US); Chae-Ryon Kong, Daegu (KR); Jeon Woong Kang, Melrose, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1055 days.

(21) Appl. No.: 13/167,445

(22) Filed: Jun. 23, 2011

(65) Prior Publication Data

US 2012/0035442 A1 Feb. 9, 2012

Related U.S. Application Data

(60) Provisional application No. 61/430,733, filed on Jan. 7, 2011, provisional application No. 61/370,870, filed on Aug. 5, 2010.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/1455* (2013.01); *G01J 3/0208* (2013.01);
(Continued)

(58) Field of Classification Search
CPC .............. A61B 5/1455; A61B 5/14551; A61B 5/14552; A61B 5/0059; A61B 5/145; A61B 5/14532
(Continued)

(56) References Cited

U.S. PATENT DOCUMENTS 5,199,431 A 4/1993 Kittrell et al.
5,293,872 A 3/1994 Alfano et al.
(Continued)

FOREIGN PATENT DOCUMENTS

WO 96/29925 10/1996
WO 03/087793 10/2003
(Continued)

OTHER PUBLICATIONS

Barman et al. "Accurate Spectroscopic Callibration for Noninvasive Glucose Monitoring by Modeling the Physiological Glucose Dynamics," Analytical Chemistry, vol. 82, No. 14, Jul. 15, 2010.
(Continued)

*Primary Examiner* — Eric Winakur
*Assistant Examiner* — Chu (JJ) Chuan Liu
(74) *Attorney, Agent, or Firm* — McCarter & English, LLP

(57) ABSTRACT

The present invention further relates to the selection of the specific filter combinations, which can provide sufficient information for multivariate calibration to extract accurate analyte concentrations in complex biological systems. The present invention also describes wavelength interval selection methods that give rise to the miniaturized designs. Finally, this invention presents a plurality of wavelength selection methods and miniaturized spectroscopic apparatus designs and the necessary tools to map from one domain (wavelength selection) to the other (design parameters). Such selection of informative spectral bands has a broad
(Continued)

scope in miniaturizing any clinical diagnostic instruments which employ Raman spectroscopy in particular and other spectroscopic techniques in general.

43 Claims, 26 Drawing Sheets

(51) Int. Cl.
    *G01J 3/02* (2006.01)
    *G01J 3/44* (2006.01)
    *G01N 21/65* (2006.01)
    *A61B 5/00* (2006.01)

(52) U.S. Cl.
    CPC ........... *G01J 3/0216* (2013.01); *G01J 3/0218* (2013.01); *G01J 3/0272* (2013.01); *G01J 3/44* (2013.01); *G01N 21/65* (2013.01); *A61B 5/4312* (2013.01); *A61B 5/444* (2013.01); *A61B 2560/0223* (2013.01); *G01N 2201/129* (2013.01)

(58) Field of Classification Search
    USPC ....... 600/310, 316, 322, 323, 324, 326, 331, 600/340, 473, 476
    See application file for complete search history.

(56) References Cited

U.S. PATENT DOCUMENTS

| | | | |
|---|---|---|---|
| 5,452,723 A | 9/1995 | Wu et al. | |
| 5,517,315 A | 5/1996 | Snail et al. | |
| 5,553,616 A | 9/1996 | Ham et al. | |
| 5,615,673 A * | 4/1997 | Berger et al. | 600/326 |
| 5,617,205 A * | 4/1997 | Dou | G01J 3/44 356/301 |
| 5,625,451 A | 4/1997 | Schiff et al. | |
| 5,661,556 A | 8/1997 | Schiff et al. | |
| 5,754,289 A * | 5/1998 | Ozaki | G01N 21/65 356/301 |
| 5,971,551 A | 10/1999 | Winston et al. | |
| 6,008,889 A | 12/1999 | Zeng et al. | |
| 6,044,285 A | 3/2000 | Chaiken et al. | |
| 6,064,897 A * | 5/2000 | Lindberg et al. | 600/316 |
| 6,069,689 A | 5/2000 | Zeng et al. | |
| 6,070,093 A * | 5/2000 | Oosta et al. | 600/316 |
| 6,128,525 A | 10/2000 | Zeng et al. | |
| 6,151,522 A * | 11/2000 | Alfano | A61B 5/0075 600/310 |
| 6,167,290 A | 12/2000 | Yang et al. | |
| 6,184,528 B1 | 2/2001 | DiMarzio et al. | |
| 6,223,063 B1 | 4/2001 | Chaiken et al. | |
| 6,289,230 B1 | 9/2001 | Chaiken et al. | |
| 6,292,686 B1 | 9/2001 | Chaiken et al. | |
| 6,352,502 B1 | 3/2002 | Chaiken et al. | |
| 6,370,406 B1 * | 4/2002 | Wach et al. | 600/310 |
| 6,377,828 B1 | 4/2002 | Chaiken et al. | |
| 6,377,841 B1 | 4/2002 | Lin et al. | |
| 6,389,306 B1 | 5/2002 | Chaiken et al. | |
| 6,483,590 B1 | 11/2002 | Davis | |
| 6,503,478 B2 | 1/2003 | Chaiken et al. | |
| 6,556,343 B1 | 4/2003 | Fludger et al. | |
| 6,681,133 B2 | 1/2004 | Chaiken et al. | |
| 6,826,424 B1 | 11/2004 | Zeng et al. | |
| 6,898,458 B2 | 5/2005 | Zeng et al. | |
| 6,965,431 B2 | 11/2005 | Vo-Dinh et al. | |
| 7,050,842 B2 | 5/2006 | Chaiken et al. | |
| 7,115,841 B2 | 10/2006 | Zeng et al. | |
| 7,190,452 B2 | 3/2007 | Zeng et al. | |
| 7,253,894 B2 | 8/2007 | Zeng et al. | |
| 7,497,992 B2 | 3/2009 | Cunningham et al. | |
| 7,508,524 B2 | 3/2009 | Mahadevan-Jansen et al. | |
| 7,573,570 B2 | 8/2009 | Zhang | |
| 7,583,381 B2 | 9/2009 | Wilson et al. | |
| 7,599,732 B2 | 10/2009 | Sevick-Muraca et al. | |
| 7,602,488 B2 | 10/2009 | Claps et al. | |
| 7,610,080 B1 | 10/2009 | Winchester, Jr. et al. | |
| 7,654,957 B2 | 2/2010 | Abreu | |
| 7,664,605 B2 | 2/2010 | Chaiken et al. | |
| 7,672,702 B2 | 3/2010 | Hwang et al. | |
| 7,700,928 B2 | 4/2010 | Rasnow et al. | |
| 7,830,522 B2 | 11/2010 | Han et al. | |
| 7,837,371 B2 | 11/2010 | Grotsch et al. | |
| 7,862,216 B2 | 1/2011 | Friedrichs et al. | |
| 8,306,593 B2 | 11/2012 | Hwang et al. | |
| 2002/0091322 A1 | 7/2002 | Chaiken et al. | |
| 2003/0176777 A1 | 9/2003 | Muller-Dethlefs | |
| 2003/0225362 A1 | 12/2003 | Currie et al. | |
| 2003/0227628 A1 | 12/2003 | Kreimer et al. | |
| 2004/0073120 A1 | 4/2004 | Motz et al. | |
| 2004/0160601 A1 | 8/2004 | Womble et al. | |
| 2004/0169854 A1 | 9/2004 | Vo-Dinh et al. | |
| 2004/0181344 A1 | 9/2004 | Stephanopoulos et al. | |
| 2006/0001872 A1 | 1/2006 | Naya | |
| 2006/0237639 A1 | 10/2006 | Kley | |
| 2007/0049809 A1 * | 3/2007 | Bechtel et al. | 600/316 |
| 2007/0060806 A1 | 3/2007 | Hunter et al. | |
| 2007/0087430 A1 | 4/2007 | Siegel et al. | |
| 2007/0127019 A1 | 6/2007 | Zribi et al. | |
| 2007/0195320 A1 | 8/2007 | Sriram et al. | |
| 2007/0197880 A1 * | 8/2007 | Maynard et al. | 600/300 |
| 2007/0219434 A1 | 9/2007 | Abreu | |
| 2007/0258894 A1 | 11/2007 | Melker et al. | |
| 2008/0200781 A1 | 8/2008 | Van Herpen et al. | |
| 2008/0274489 A1 | 11/2008 | Siegel et al. | |
| 2008/0306363 A1 | 12/2008 | Chaiken et al. | |
| 2009/0024019 A1 | 1/2009 | Stein et al. | |
| 2009/0073432 A1 | 3/2009 | Jalali et al. | |
| 2009/0219525 A1 | 9/2009 | Marcus et al. | |
| 2009/0303462 A1 | 12/2009 | Munger et al. | |
| 2010/0010325 A1 | 1/2010 | Ridder et al. | |
| 2010/0028853 A1 | 2/2010 | Harmon | |
| 2010/0067000 A1 | 3/2010 | Baumberg et al. | |
| 2010/0076319 A1 | 3/2010 | Mannheimer et al. | |
| 2010/0079753 A1 | 4/2010 | Hehlen | |
| 2010/0081901 A1 | 4/2010 | Buice et al. | |

FOREIGN PATENT DOCUMENTS

| | | |
|---|---|---|
| WO | 2004/070368 | 8/2004 |
| WO | 2006/116637 | 11/2006 |
| WO | 2007/014173 | 2/2007 |
| WO | 2008/002488 | 2/2008 |
| WO | 2009/117603 | 9/2009 |
| WO | 2011/083111 | 7/2011 |

OTHER PUBLICATIONS

Lipson et al., "Requirements for Calibration in Noninvasive Glucose Monitoring by Raman Spectroscopy," Journal of Diabetes Science and Technology, vol. 3, Issue 2, Mar. 2009.

Patil et al., "Combined Raman Spectroscopy and Optical Coherence Tomography Device for Tissue Characterization," Optical Society of America, Optics Letters, vol. 33, No. 10, May 15, 2008.

Enejder et al., "Blood Analysis by Raman Spectroscopy," Optical Society of America, Optics Letters, vol. 27, No. 22, Nov. 15, 2002.

Kodach et al., "Optics Communication," Optics Communications 281 4975-4978, 2008.

Lieber et al., "Automated Method for Subtraction of Fluorescence from Biological Raman Spectra," Society for Applied Spectroscopy, Applied Spectroscopy, vol. 57, No. 11, 2003.

Cullum et al., "Development of a Compact, Handheld Raman Instrument with No Moving Parts for Use in Field Analysis," American Institute of Physics, Review of Scientific Instruments, vol. 71, No. 4, Apr. 2000.

Liu et al., "Determination of Effective Wavelengths for Discrimination of Fruit Vinegars Using Near Infrared Spectroscopy and Multivariate Analysis," SciendDirect, Analytica Chimica ACTA 615, 10-17, 2008.

(56) References Cited

OTHER PUBLICATIONS

Kodach et al., "Wavelength Swept Ti:sapphire Laser," Optics Communications, p. 4975-4978, Jun. 16, 2008.

* cited by examiner

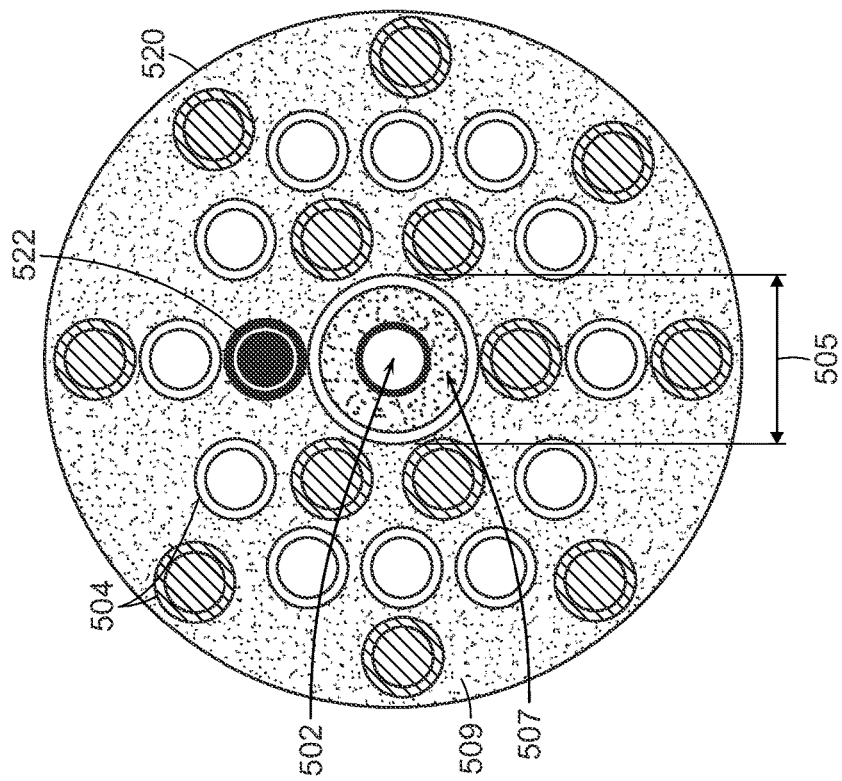
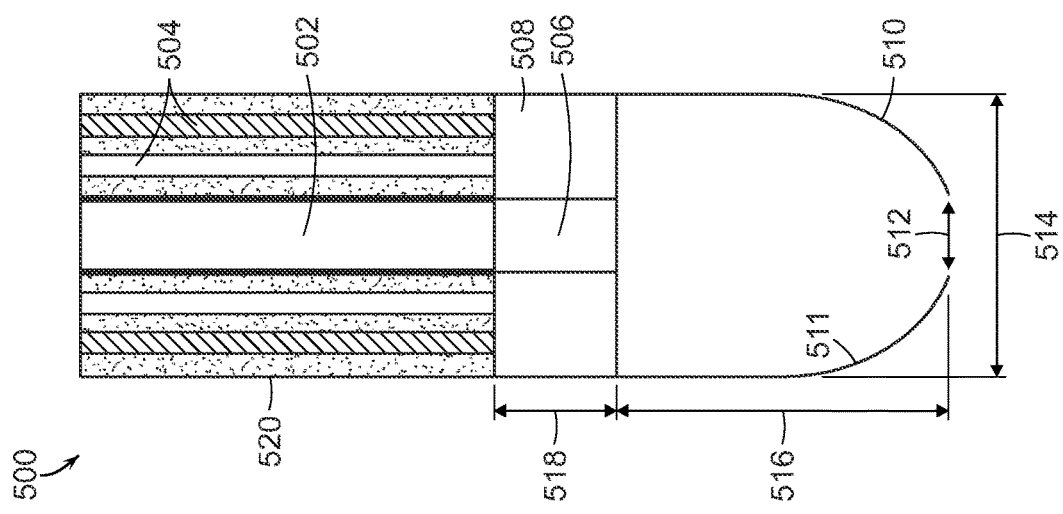

(Profile I)

(Profile II)

PORTABLE RAMAN DIAGNOSTIC SYSTEM

CROSS-REFERENCE TO RELATED APPLICATION

This application claims the benefit of U.S. Provisional Application No. 61/370,870 filed Aug. 5, 2010 and U.S. Provisional Application No. 61/430,733 filed Jan. 7, 2011, the entire contents of which are incorporated herein by reference.

STATEMENT REGARDING FEDERALLY SPONSORED RESEARCH OR DEVELOPMENT

This invention was supported, in whole or in part, by NIH Contract No. P4102594. The Government has certain rights in the invention.

BACKGROUND OF THE INVENTION

The wealth of information available in Raman spectra has led to accurate quantification of molecular and morphological components embedded in complex biological samples. The great interest in Raman spectroscopy lies in its potential for accurate and real time clinical diagnosis for a wide variety of diseases such as malignant tumors (cancers) and vulnerable arterial plaques (atherosclerosis). In addition, near-infrared (NIR) Raman spectroscopy can be employed for non-invasive applications such as continuous monitoring of glucose in diabetics and creatinine and urea in neonates and patients in intensive care units.

While successful application in terms of tissue classification as well as analyte concentration prediction has been achieved in several in vitro, animal model and even human subject studies, few of the promising results have been translated into clinical practice. This is in sharp contrast to its widespread applications in the process monitoring industry. The lack of similar usage in the health-care and medical devices sector can be attributed to two primary factors, namely the lack of robustness in Raman diagnostic methods that results in unsuccessful calibration transfer from one human subject to another. This is a direct consequence of the presence of spurious correlations in the diagnostic analysis between the analyte of interest and the spectral interferents, and further, the large spatial footprint of the developed Raman systems, which prevents its usage in a clinical facility. This factor is even more pronounced when a diagnostic tool has to be developed for a home user such as continuous blood glucose monitoring, where its feasibility is dependent on the convenience of the device, as well as its cost. Typically, the reduction in the size of a Raman system is constrained by the light source (e.g. NIR laser) and the spectrograph. Since Raman signals are intrinsically weak, the CCD detectors are often (especially for NIR Raman spectroscopy) cooled to reduce thermal and dark current noise. The additional cooling element also adds to the size of the clinical instrument. Further improvements are needed for both clinical and laboratory use.

SUMMARY OF THE INVENTION

The present invention relates to an integrated approach utilizing a process of eliminating the uninformative or spurious spectral regions which simultaneously removes the necessity for a full spectrograph-CCD system. This approach enables the use of a portable Raman diagnostic system, having significantly reduced size and weight (less than 20 lbs and preferably less than 10 lbs) while retaining the required sensitivity.

In order to provide a quantitative measurement, multivariate calibration has been employed for determining the concentrations of analytes in multi-component mixtures that exhibit linear response. Such analytical methods have been extensively used for spectroscopy, due to the inherently multivariate nature of the spectroscopic data. The application of these methods is critical when complex biochemical systems, such as tissue, need to be analyzed for an analyte of interest (e.g. glucose) in the presence of several spectral interferents. Conventionally, multivariate calibration is performed with the spectral information acquired over the full spectral region (i.e. where the analytes of interest have a characteristic spectral profile). The underlying hypothesis for such full spectrum analysis is that the prediction accuracy of the method can only be enhanced by the presence of larger quantities of spectral information. To acquire the full spectrum necessary for the analysis, a dispersive spectrograph and a CCD detector is typically employed.

It has been found, however, that spurious correlations on the multivariate calibration procedures, especially for implicit schemes (e.g. partial least squares (PLS) and principal component regression (PCR)). Evidently, the presence of such spurious correlations, which may be caused by temporal (system) drifts or by covariations among sample constituents, which impede calibration transfer by introducing non-analyte specific variances.

An important consideration then is how many and which of the spectral bands (also known as wavelength intervals) facilitate accurate prediction. In other words, as large portions of the full spectrum contains spurious information detrimental to the analysis, it is important to select the appropriate wavelength intervals. Addition of uninformative zones also gives rise to more loading vectors/principal components, which tend to incorporate irrelevant sources of variance and noise thereby reducing the efficacy of the system.

A preferred embodiment of the present invention uses wavelength interval selection based on non-linear representation, such as support vector regression. The wavelength selection protocol is based on the minimization of cross-validation error in the training data. This outperforms wavelength selection in typical linear methods such as partial least squares and principal component regression. The present method computes the spectral window(s) or regions of the Raman spectrum where the effects of potential interference with respect to the analyte of interest are minimized. This method also optimizes the selection of spectral bands as opposed to selecting individual (and often isolated) spectral points (pixels). Any vibrational and rotational spectra give Voigt profiles that typically have a full width at half maximum (FWHM) of at least 4-8 $cm^{-1}$. The existence of such intrinsic spectral intervals leads to the selection of minimum spectral band size. The application of the preferred method leads to a significant reduction in number of wavelengths that need to be sampled (upward of three-fold as compared to full spectrum analysis) for the development of an accurate calibration system. This reduction can be partly attributed to the chemical specificity of Raman spectroscopy, which allows the detection of molecules by sampling a limited number of wavelengths. In addition, it has been found that the prediction accuracy and robustness are enhanced as a result of the wavelength selection procedure.

Importantly, the selection of only a limited number of spectral bands allows the construction of a miniaturized Raman instrument by replacing the spectrograph-CCD combination with an array of optical bandpass filters and light detector(s). One of the embodiments of such a design can incorporate a single photodiode as a light detector. The principle is to guide the collected light into the appropriate filter(s), which transmit light of certain wavelength(s) only (corresponding to the selected specific Raman band(s)) to the corresponding photo-detector(s). The spectral band width is limited by the bandwidth of the corresponding filter.

Various embodiments can be used to implement the above methodology. A preferred embodiment can include a single excitation source and multiple detection channels. The detection channels can include a rotating optical filter wheel with a single photodiode. During signal acquisition, the filter wheel can be rotated to collect the signals corresponding to the specific Raman bands at the single photodiode. However, mechanical rotation has limitations including speed of acquisition and pre-assigning of optical filters corresponding to specific spectral bands.

To overcome these drawbacks, a preferred embodiment uses a tunable filter, either a liquid crystal tunable filter (LCTF) or an acousto-optical tunable filter (AOTF), can be employed in conjunction with a photodiode, e.g. avalanche photodiode (APD). As per the analyte of interest in the application, the system controller can be programmed to the specific frequencies that are detected at the APD. Depending on the liquid crystal or acoustic wave frequency, birefringent crystal properties change to enable rapid wavelength tuning. Indeed, in such cases, the temporal limits of the system are from the Raman acquisition process, as opposed to the tuning speed.

A preferred embodiment can include a plurality of excitation sources and a single detector channel. The excitation can be performed by a sweeping source (e.g. polygon mirror scanner sweeping source, Fabry-Perot tunable filter sweeping source, AOTF-based sweeping source) while the detection can be through a single bandpass filter and photodetector. The sweeping source can cycle through a set of pre-assigned excitation frequencies to provide the different wavenumber bands at the defined wavelength range of the bandpass filter. The advantage of using tunable excitation instead of tunable detection is that most of the tunable filters are polarization sensitive and it is easier to ensure proper polarization of the laser rather than correcting for the polarized signal obtained after sample scattering. Depending on the application, coupling multiple monochromatic sources such as diode lasers onto the excitation fiber can also provide another embodiment for implementing. It is essential to understand that incorporation of wavelength selection allows the signal acquisition time to be shortened considerably because the instrument has to cycle through (serially) fewer number of spectral channels. Conversely, use of the same signal acquisition time facilitates better signal-to-noise ratio.

A further embodiment combines the single excitation light source with multiple wavelength detection with multiple excitation, single detection to form a multi-excitation source, multi-detection unit. This system employs a sweeping source and a tunable filter with a corresponding photo-detector. The advantage of such an embodiment lies in the less stringent requirements placed on both the excitation and detection systems. In this embodiment, the sweeping source can cycle through one-fourth of the number of total excitation frequencies if the number of detector channels is increased by a factor of four, for example.

Finally, to accurately analyze a biological sample using a handheld unit, it is critical to collect a large number of backscattered (or transmitted) photons. A preferred embodiment utilizes a reflection geometry, however a transmission Raman system can also be used. To improve the collection efficiency, a compound parabolic concentrator (CPC) lens can be used in conjunction with the fiber-optic probe for delivery and collection of light to and from the sample, respectively. The CPC acts as a reverse angle transformer by collecting light from all angles and converting them to the limited NA (numerical aperture) of the collection fibers. The use of a CPC can enhance collection efficiency between 7-11 times in comparison to using only commercially available fibers. Alternately, hollow core fibers and photonic crystal fibers, which have significantly larger NA than conventional ones, can also be employed. The increase in collection efficiency provides for the application of a handheld instrument for in vivo diagnostics as well as ex vivo histopathological analysis. A further embodiment utilizes a compound hyperbolic concentrator that is matched with a lens for light collection from a tissue sample.

A hand-held Raman diagnostic unit can have extensive applications in the field of disease diagnostics, as well as in analytical chemistry. For example, a miniaturized Raman system can be employed as a non-invasive continuous glucose monitor. The device can be worn around the wrist or around the waist, as is the case for the minimally invasive amperometric glucose sensors. Another embodiment relates to the detection of cancers, such as breast cancer, and its subsequent classification. Margin assessment from tissue biopsies and detection of micro-calcifications in cancerous tissue in breast tissue and for the measurement and diagnosis of skin cancers. Furthermore, handheld units can be used for forensic, pharmaceutical and process monitoring applications. The use of optical fiber probes can also be used for remote monitoring.

BRIEF DESCRIPTION OF THE DRAWINGS

FIG. 9A illustrates a cross-sectional view of a fiber optic delivery and collection system with a CPC.

FIG. 9B illustrates a cross-sectional view of the fiber delivery and collection system.

DETAILED DESCRIPTION OF THE INVENTION

Figure 1:
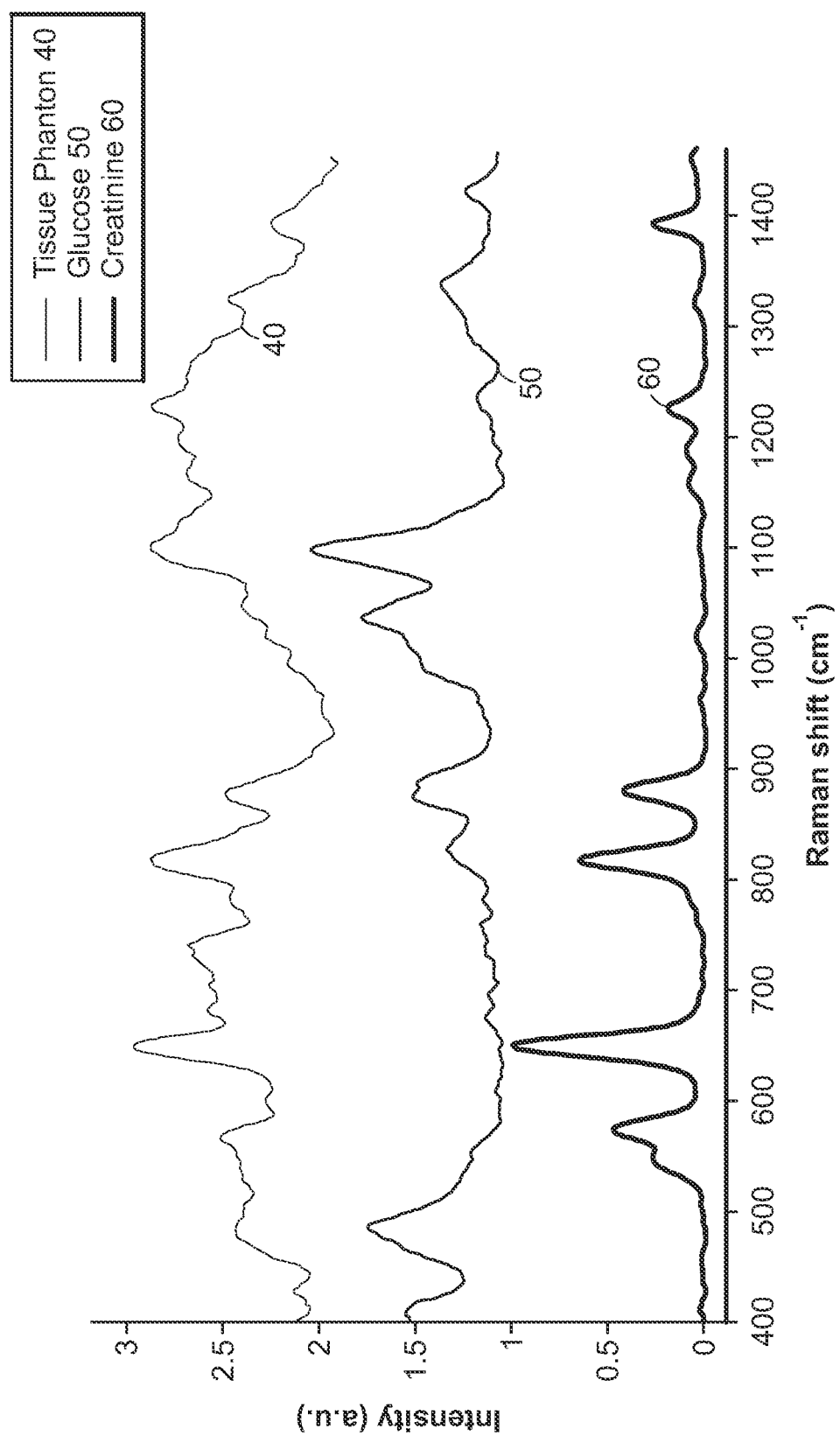
FIG. 1 illustrates a residue error plot for SVM.

The present invention relates to portable Raman diagnostic systems utilizing wavelength selection which significantly refine the performance of the multivariate calibration techniques. However, the addition of uninformative spectral regions give rise to more loading vectors/principal components, which tend to incorporate irrelevant sources of variance and noise. An important consideration then is how many and which of the spectral bands (also known as wavelength intervals) facilitate accurate measurement. In other words, as only small portions of the full spectrum contain useful Raman features, it is important to select the appropriate wavelength intervals. Clearly, such selection is also dependent on the rest of the constituents in the sample being measured, because of the resultant spectral overlap which may be observed in certain regions.

Although existing wavelength selection methods can work in conjunction with any calibration method, such as ordinary least squares (OLS) and partial least squares (PLS) analysis, a number of procedures have been developed to assist in wavelength selection that differ from one another in the objective criterion used for measuring the optimal wavelengths. Stochastic search methods accept transitory reductions of predictive quality during an optimization procedure enabling them to escape local extrema without detailed analysis. However, this stochastic nature (involving predictable processes and random actions) is also a major disadvantage in establishing a robust spectral subset since it is almost impossible to reproduce measurements. While the ability of these methods to rapidly converge to a solution provides a distinct advantage in certain applications, the aforementioned lack of robustness is an impediment to the selection of instrumentation.

Alternatively, spectral interval selection also called moving window partial least squares regression (MWPLSR), can be used for enhancing predictive quality of calibration methods. MWPLSR, and its variants (changeable size moving window partial least squares and searching combination moving window partial least squares), are advantageous in searching for informative spectral regions for multi-component spectral analysis. This method applies PLS calibration in every window which moves over the spectrum and selects informative regions on the basis of the lowest sum of residual errors. Such a moving window approach based on minimization of the residual error can improve prospective prediction of analytes in mixed solutions.

A preferred embodiment for wavelength spectral window selection involves selecting lower residue error wavelength regions for both linear (PLS) and non-linear (support vector regression, SVR) multivariate regression methods. To implement this, construct a spectral window size of w, which starts at the $i^{th}$ spectral channel and ends at the $(i+w-1)^{th}$ spectral channel. The window is moved across the full spectrum range. PLS and SVM models are built and root mean squared error of validation (RMSEV) is calculated for each subset by performing prediction on the validation sets. For all windows, plot the RMSEV as a function of the position of the spectral window. The spectral channels with large errors imply that the responses at these channels are highly contaminated by the factors that cannot be modeled accurately using the calibration samples.

Furthermore, the continuity of the spectral response in vibrational spectra (where the characteristic FWHM is at least 4-16 cm$^{-1}$) channels, the selection to be performed for spectral intervals instead of individual scattered points across the entire spectrum. In other words, if there is a wavelength that is informative for the calibration model, there typically is a spectral interval around the wavelength that contains useful information to build the representation due to the intrinsic bandwidth of the Raman features. Similarly, if a spectral channel is contaminated by the factors that are not related to the concentration of the analyte of interest, the wavelength interval around the channel is also unlikely to contain much useful information. Based on this analysis, a moving window method is employed to select spectral bands, in contrast to isolated wavelengths.

The underlying assumption that the relationship between the spectra and the property of interest (analyte concentration) is linear does not accurately reflect many systems under all circumstances, especially for clinical measurements. For example, in transcutaneous monitoring of blood glucose, the assumption of linearity may fail due to fluctuations in process and system variables, such as changes in temperature, sampling volume and physiological glucose dynamics. Although weak non-linearities can be modeled by the conventional linear methods such as PLS and principal component regression (PCR) by retaining more factors than is necessitated by the chemical rank of the system, this risks the inclusion of irrelevant sources of variance and noise in the calibration process. Such incorporation of non-analyte specific variance renders the process incapable of prospective prediction. To represent the potential curved effects and to avoid overfitting of the data, support vector machines has been introduced for non-linear classification and regression (SVR) been used in classification problems.

In SVR, estimation is calculated with the help of the regression coefficients (w) that relates regressors (x) and the dependent variable (y) $y=w^T x + b$. For a preferred embodiment, x and y represent the acquired sample spectra and the concentration of the analyte of interest, respectively. The regression is calculated by minimizing a cost function, which regularizes the regression coefficients and penalizes the net regression error. Reduction of large regression coefficients improves the generalization ability of the method, as they tend to cause excessive variance. The resultant equation is then solved with Lagrange multipliers as a constrained optimization problem to yield the following regression function:

$$y = \sum_i (\alpha_i - \alpha_i^*)\langle x_i, x\rangle + b \quad (1)$$

where i is the index of the calibration data, α are the Lagrange multipliers and $\langle x_i,x\rangle$ denotes the inner product. From Eq. (1), it is clear that each calibration data point has its own Lagrange multiplier, which decides the impact of the point on the final solution. Eq. (1) can be readily extended to handle non-linear regression by substituting the inner product $\langle x_i,x\rangle$ with a kernel function that satisfies Mercer's conditions:

$$y = \sum_i (\alpha_i - \alpha_i^*) K(x_i, x) + b \quad (2)$$

The most widely used kernel for non-linear regression is the radial basis function (RBF) and can be expressed as:

$$K(x_i, x) = \exp\left(-\frac{\|x - x_i\|^2}{\sigma^2}\right) \quad (3)$$

where $\sigma^2$ is the RBF kernel parameter. In addition to the kernel parameter, solving a support vector regression involves optimizing the regularization parameter, which determines the tradeoff between minimizing the regression error and the regression coefficient sizes.

Thus a preferred embodiment of the present invention utilizes residue error plot based wavelength selection methods to develop optimized PLS and SVR models from the Raman spectra and glucose concentrations in the calibration data sets. The developed calibration methods are subsequently used for leave-one-out cross-validation and prospective prediction to compare the respective performances.

Two data sets have been employed to investigate: (a) the relative prediction performance of wavelength selected linear and non-linear calibration methods, and (b) the transferability of the wavelength selected subset from one sample to another. For (a), a physical tissue model (tissue phantom) is used, which focuses on glucose detection in a multicomponent mixture. To accomplish objective (b), a clinical dataset from human subjects undergoing oral glucose tolerance tests (OGTT) is analyzed.

For the tissue phantom data set, spectra were collected from 50 tissue phantoms containing randomly varying concentrations of two Raman active analytes, glucose and creatinine, the concentrations varying between 5 mM to 30 mM. These samples also contained randomized concentrations of India ink and intralipid to introduce varying amounts of turbidity in the samples mimicking the absorption and scattering parameters in human skin tissue. Spectroscopic measurements were performed on aliquots of these tissue phantoms in a fused silica cuvette by exciting with a 830 nm external cavity diode laser (obtained from Process Instruments). The back-scattered light was passed through a modified f/1.4 spectrograph (Kaiser Optical Systems, Inc.) before spectral acquisition using a liquid-nitrogen cooled CCD (Princeton Instruments). Further descriptions of systems used to acquire this data can be found in U.S. Pat. No. 5,615,673 and U.S. patent application Ser. No. 11/412,418 filed Apr. 27, 2006 and Ser. No. 11/492,214 filed on Jul. 24, 2006, the above patent applications being incorporated herein by reference. A representative tissue phantom spectrum (bottom) is shown in FIG. 1 along with the glucose (middle) and creatinine (top) Raman spectra (spectra are offset for clarity). The background including the cuvette Raman features have been removed from the tissue phantom as well as the constituent spectra using an automated subtraction method.

For the human subject data set, transcutaneous blood glucose measurements were performed on thirteen healthy individuals. Following standard OGTT protocol, the subjects were given 220 mL of a beverage containing 75 g of glucose before the measurement. In this system, a laser was focused onto the forearm of the human with an average power of 300 mW and a spot size of ~1/mm$^2$. 20-32 Raman spectra were taken for each person over the 2-3 hour period. Concomitant blood glucose measurements were performed every 10 minutes from extracted blood samples, and spline interpolation was used to correlate the measured blood glucose concentrations with the spectra collected at the intermediate time points. For the analysis below, datasets from subjects exhibiting motional artifacts, inadequate SNR and impaired glucose tolerance profiles in the acquired spectra have been excluded.

Figure 2:
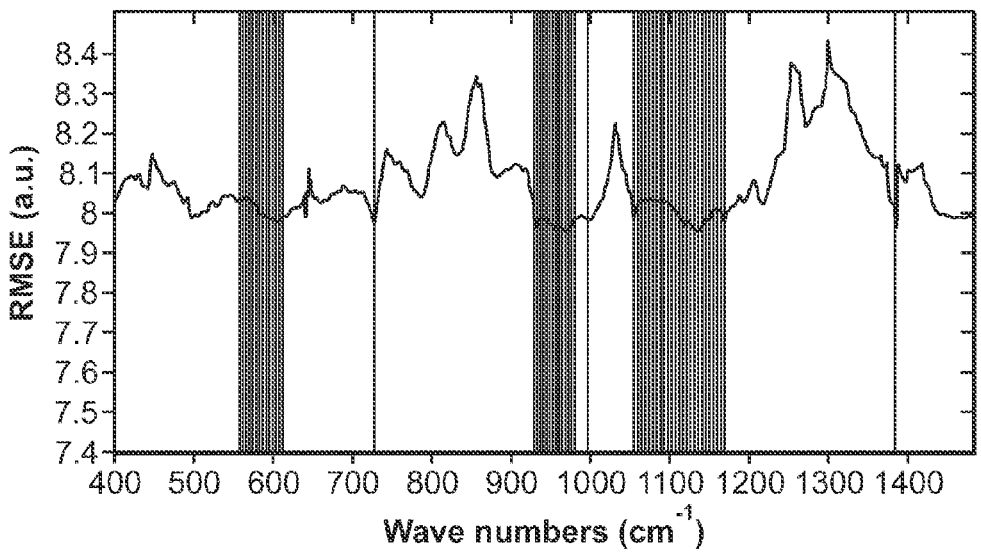
FIG. 2 illustrates a comparison of prediction errors in PLS and SVM across feature-selection range.

In the tissue phantoms, twenty prediction samples were randomly chosen from the entire data set and kept aside for prospective application. The remaining thirty tissue phantoms were randomly split into twenty calibration samples and ten validation samples. First, the moving window approach is used to generate a regression vector from the calibration sample spectra corresponding to the specific window. This regression vector is then used on the validation samples to obtain the root-mean-squared error of validation (RMSEV). The window is subsequently moved over the full spectrum to construct the residue error plot as a function of the moving window position (Raman shift). In addition, to be consistent with the continuity of the spectral response, only spectral bands having a minimum FWHM of 4 $cm^{-1}$ are selected. FIG. 2 shows a residue error plot calculated from a representative partition of calibration and validation sets. From the residue plot, pixels (spectral points) are selected which provide the least RMSEV. In analysis, 300 to 900 spectral points in increments of 100 were selected (for this analysis, 1 pixel approximately corresponds to 1.45 $cm^1$). For each subset of spectral points, the regression vector is generated from the thirty tissue phantoms constituted by the calibration and validation data sets. The computed regression vector is then used prospectively on the corresponding prediction set (i.e. prediction spectra at the previously selected wavelengths) and RMSEP is calculated for the specific subset of spectral points. To ensure the reproducibility of the prediction results, 100 iterations are performed to obtain an average RMSEP.

In a preferred method, different window sizes from 10 to 20 spectral points are selected. This size range corresponds to the FWHM of the prominent bands in the glucose Raman spectrum.

Assigning window sizes beyond this range exhibited little adverse effect on the resultant residue lines. Wavelength selection using the above protocol was performed for both PLS and SVR calibration. PLS models are created based on the number of loading vectors (six) that provide the least error in cross-validation for full spectrum analysis. (The number of loading vectors is also consistent with the chemical rank of the system.) A standard recommendation for PLS calibration is to incorporate at least three times the number of samples as the rank of the calibration model. To satisfy this criterion, twenty samples are chosen for calibration analysis. In addition, the SVR calculations are carried out using a SVM MATLAB toolbox. Prior to wavelength selection for SVR processing, the Raman spectra are linearly scaled by dividing each spectrum by the maximum intensity value to prevent the skewed effect arising from the larger pixel intensity values. The optimal parameters C and $\sigma^2$ are obtained by employing a grid search procedure in the range of 1 to 10000 (C) and 0.01-10 ($\sigma^2$), respectively.

Similar analysis steps are also followed for the human subject dataset. Summary statistics of individuals are given in Table 1.

TABLE 1

Summary statistics of human subject dataset

| Subject | Total_ Samples | Cali-bration_ Samples | Average_ Concen-tration | Minimum_ Concen-tration | Maximum_ Concen-tration |
|---|---|---|---|---|---|
| 3 | 25 | 15 | 144.1 | 83 | 188 |
| 4 | 26 | 16 | 146.3 | 78 | 204 |
| 6 | 26 | 16 | 145.4 | 84 | 191 |
| 7 | 30 | 20 | 173.5 | 95 | 223 |
| 9 | 20 | 10 | 134.4 | 82 | 169 |
| 11 | 32 | 22 | 167.9 | 71 | 201 |
| 13 | 25 | 15 | 135.2 | 80 | 190 |
| 14 | 26 | 16 | 153.1 | 79 | 208 |
| 15 | 28 | 18 | 160.1 | 70 | 209 |
| 17 | 25 | 15 | 110.7 | 69 | 142 |
| 18 | 29 | 19 | 121.9 | 85 | 167 |
| 19 | 31 | 21 | 139.2 | 68 | 198 |
| 20 | 27 | 17 | 159.2 | 69 | 201 |

From a representative human data set (subject A) all but five data points are used to develop the wavelength-selected regression representation. The developed regression representation is then applied on the remaining five data points of subject A to evaluate the RMSEV as a function of the moving window position and subsequently for the construction of the residue error plots. To obtain enhanced robustness in the wavelength subset selection, perform 100 iterations by re-partitioning the calibration and validation data sets of subject A. The residue error plots from these iterations are added to form a cumulative error plot as a function of wavelength. The spectral bands with the least cumulative error are selected for prospective application in the other human datasets. For clarity, henceforth call the remaining subjects as $B_i$, where i represents the index of the individual. To analyze $B_i$, the data points are split into calibration and prediction. The regression methods are constructed on the calibration data points of $B_i$ using only the spectral bands selected from subject A. These methods are subsequently used to estimate the glucose concentrations of the prediction data points in subject B. The resultant prediction errors provide a true measure of the prospective applicability of the pre-selected spectral subset, i.e. the transferability and robustness of the selected bands across humans. The loading vectors for PLS analysis can be optimized for each subject based on leave-one-out cross-validation on the calibration data points. Similar SVR optimization is also carried out for C and $\sigma^2$ in the range of 1 to 1000 and 0.01 to 1, respectively.

In conjunction with measurement of RMSEP, the relative predictive determinant (RPD) metric can be employed to classify the overall prediction quality of different analytes in the tissue phantoms. RPD is defined as the ratio of the standard deviation of the reference concentration in the sample population ($\sigma_R$) to the standard error of prediction (the standard deviation of the differences between predicted and reference values) ($\sigma_{R-P}$):

$$RPD = \frac{\sigma_R}{\sigma_{R-P}} \qquad (4)$$

Typically, a RPD value of 5 is considered to be good for quality control while a value larger than 6.5 is acceptable for process monitoring. A calibration method with a RPD value higher than 8 may be used for any application.

Figure 3:
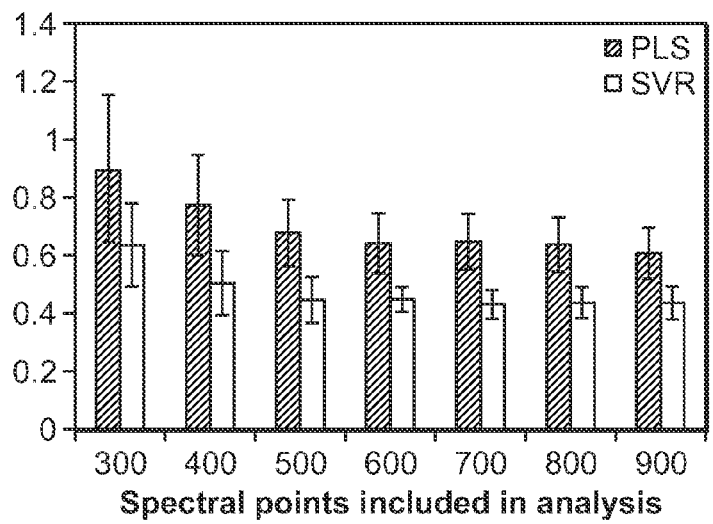
FIG. 3 illustrates a comparison of selected wavelength features using PLS and SVM.
Figure 4:
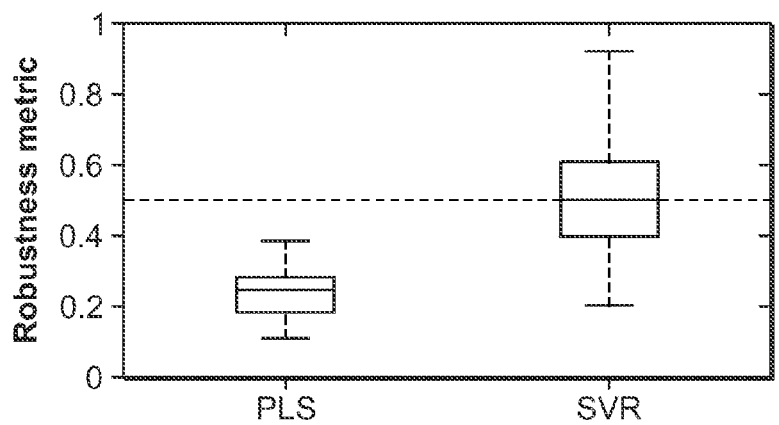
FIG. 4 compares a metric for linear and nonlinear systems for spectral window selection based on measured human data.
Figure 5C:
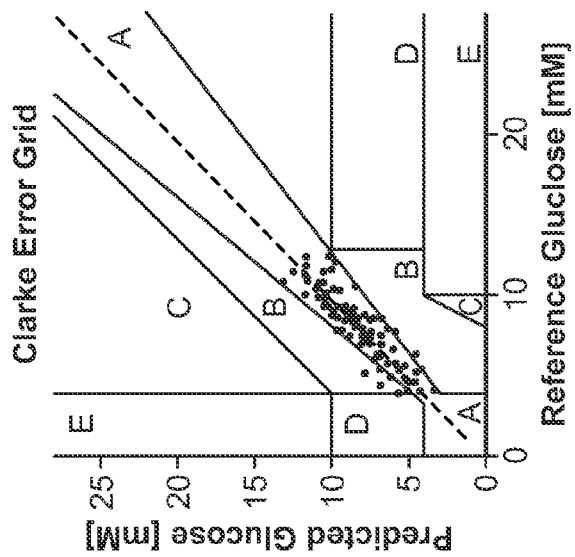
FIGS. 5A-5F illustrates a Clarke error grid analysis figures for (A) PLS using 100 pixels (B) PLS using 300 pixels (C) PLS using full spectrum (D) PLS using 100 pixels (E) PLS using 300 pixels and (F) PLS using full spectrum.
Figure 5B:
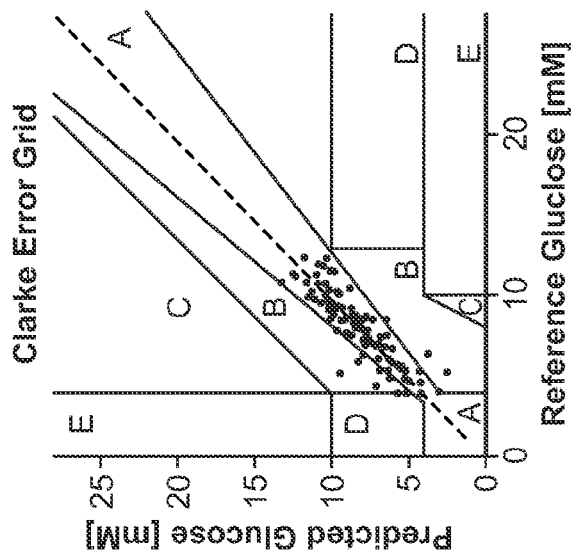
Figure 5A:
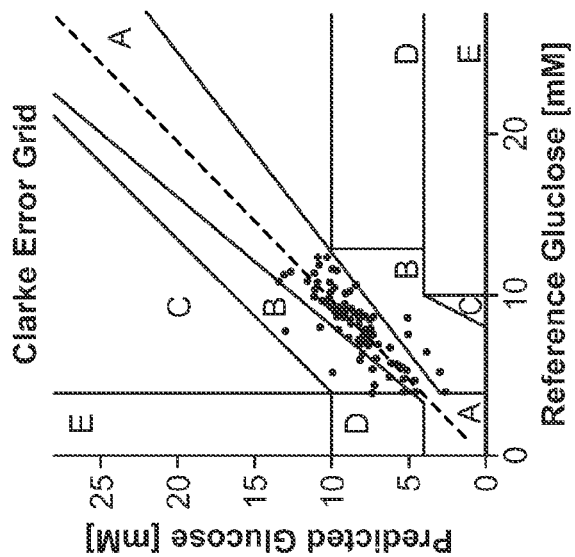
Figure 5F:
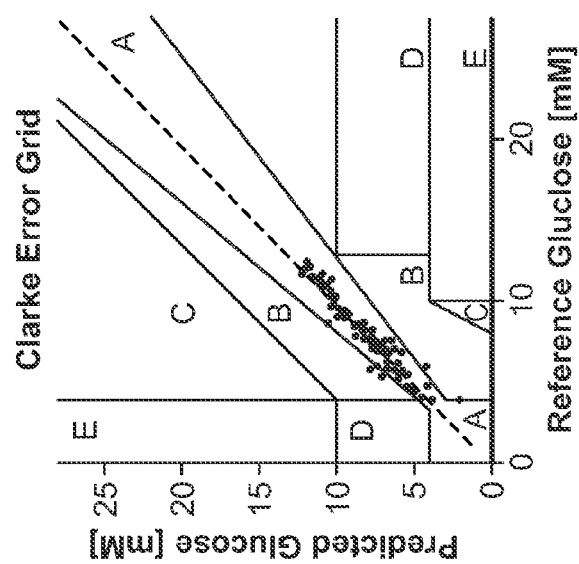
Figure 5E:
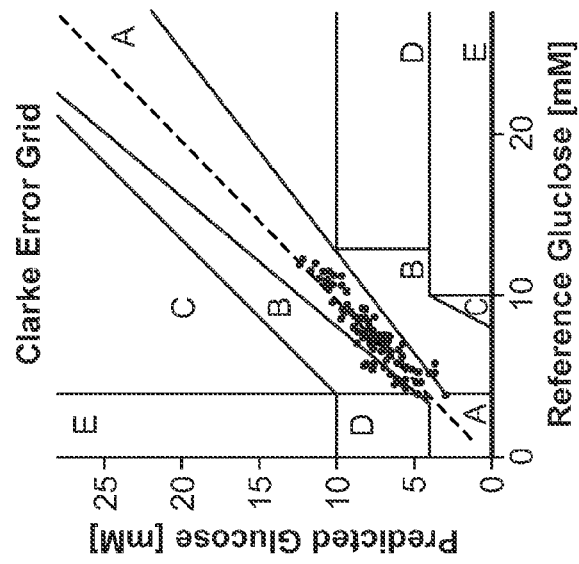
Figure 5D:
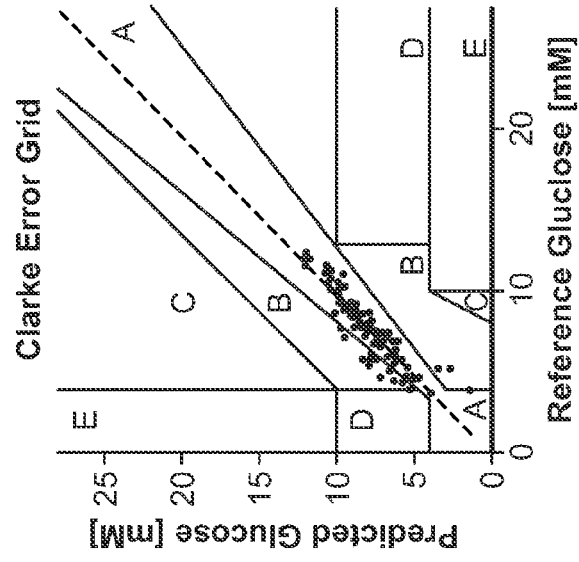

Wavelength selection was performed on the tissue phantom dataset using both PLS and SVR methods. FIG. 3 shows the results of prospective prediction for glucose obtained with PLS (left columns) and SVR (right columns) methods, where the lengths of the bars are proportional to the average RMSEP and the associated error bars represent the standard deviation of the RMSEP over the 100 iterations. FIG. 3 provides a comparative estimate of predictive performance of calibration models corresponding to the selection of minimum residue wavelength subsets of different sizes, ranging from 300 to 900 spectral points. It is evident that the SVR calibration methods always outperform the PLS calibration methods with identical size of spectral subset in regard to prospective prediction. For example, given a spectral subset size of 300 points, the mean prediction errors for glucose were measured to be 0.89 mM and 0.63 mM for the PLS and SVR methods, respectively. In fact, the SVR methods with 300 spectral points, provides approximately equivalent levels of prediction accuracy as the full spectrum PLS method (mean RMSEP of 0.6 mM).

These results, showing the improvement of prediction accuracy by performing non-linear calibration. The curved effects in the spectral data set can be attributed, for example, to the fluctuations in sampling volume due to the change in phantom turbidity (absorption and scattering). Another reason for the better performance of SVR may be the weighting of the relative importance of the calibration samples by means of the Lagrange multipliers. This facilitates the rejection of redundant and unimportant samples while emphasizing those that help in minimizing the regression error.

Further, note that as the spectral subset size is decreased initially from 900 to 500 spectral points, the prediction errors are not substantially altered, as shown in FIG. 3. However, with further decrease of the size of the spectral subset (in the range of 300 to 400 spectral points), the prediction errors rise considerably. This quantitative measure of threshold of the spectral subset size provides information specific to the analyte of interest present in the full spectrum. Particularly for the tissue phantom analysis, the glucose-specific informative regions constitute less than half of the full spectrum. Wavelength selection enhances the stability of the method relative to the collinearity in the acquired Raman spectra as well as increases the interpretability of the relationship between the method and the sample compositions by reducing the number of loading vectors to the chemical rank of the system.

Results for creatinine confirm the prediction quality for both glucose and creatinine in which a RPD metric was employed. Table 2 lists the RPD values for various calibration methods and analytes of interest.

TABLE 2

Comparison of RPD values for glucose and creatinine in tissue phantoms

|  | PLS | | | SVM | | |
| --- | --- | --- | --- | --- | --- | --- |
|  | 100 pixels | 300 pixels | Full spectrum | 100 pixels | 300 pixels | Full spectrum |
| RPD (glucose) | 3.9 | 8.45 | 12.4 | 1.6 | 12.2 | 16.9 |
| RPD (creatinine) | 5.9 | 11.4 | 17.1 | 2.4 | 15.2 | 24.2 |

Observe that both PLS and SVR methods including at least 300 spectral points show useful prediction quality. To this end, RPD provides a useful tool in evaluating the allowable minimum size of the spectral subset for different applications and analytes of interest.

The number of spectral points that provides adequate predictive ability for an analyte of interest is a function of the signal-to-noise ratio of the acquired spectra, the Raman scattering cross-section of the analyte and the spectral overlap factor between the analyte and the spectral interferents. Since this is a complex optimization problem, which invariably does not lend itself to an analytical solution, different numerical wavelength selection strategies can be pursued depending on the sample set and the analyte of interest. For example, if the Raman scattering cross-section of the analyte is appreciably larger than that of the interferents, only a small subset of features specific to the analyte may be sufficient. For example, given the very strong spectral features, around $1447\ cm^{-1}$ ($\delta CH_2$ protein/lipid) and $1650\ cm^{-1}$ (Amide I protein/lipid), in Raman spectra acquired from breast tissue, differentiation of malignant, benign and normal issue types only requires a few sets of spectral bands. This can be seen in Haka et al. Proc. Natl. Acad. Sci. USA 102, 12371 (2005) and in Scepanovic et. al., Review of Scientific Instruments 80, 043103 (2009), the entire contents of these publications being incorporated herein by reference. On the other hand, for glucose detection in a transcutaneous manner (where it is well-known that glucose constitutes approximately 0.1-0.3% of the tissue Raman spectrum), further optimization must be performed and a larger subset of wavelengths must be selected to differentiate from the interferents.

The Clarke Error Grid analysis (EGA) is a method to quantify clinical accuracy of predicted blood glucose as compared to the reference blood glucose value. EGA is known as a standard for determining the accuracy of blood glucose meters. In the Clarke error grid, region A gives values within 20%, region B gives outside of 20% but would not give inappropriate treatment, region C values lead to unnecessary treatment, region D values lead to potentially dangerous failure to detect hypo or hyperglycemia and region E values tend to confuse treatment of hypoglycemia for hyperglycemia and vice-versa. Glucose monitoring system performance is typically considered acceptable if >95% of points fall within zones A and B and no negligible points fall in zones D and E. In FIGS. 5A-5F, Clark error grids for different pixels selected in PLS and SVM models have been shown.

The FDA has proposed the use of the ISO 15197 guideline for clinical glucose measurements. According to ISO 15197 guideline, the meter measurements are within 15 mg/dL (0.83 mM) of reference for glucose concentration <75 mg/dL (4.2 mM) and within 20% for glucose concentration ≥75 mg/dL (4.2 mM). Percentage of data points following ISO 15197 criteria are tabulated in Table 3 for different pixels selected and both PLS and SVM models.

TABLE 3

Comparison of wavelength selection for PLS and SVM calibration models in human subjects based on ISO statistics

|  | PLS | | | SVM | | |
| --- | --- | --- | --- | --- | --- | --- |
|  | 100 spectral points | 300 spectral points | 900 spectral points | 100 spectral points | 300 spectral points | 900 spectral points |
| RMSEP | 23.7 | 18.6 | 16.9 | 16.9 | 15.1 | 11.3 |
| $R^2$ | 0.79 | 0.87 | 0.89 | 0.89 | 0.92 | 0.95 |
| Percentage of points satisfying ISO criteria | 83.33 | 86.66 | 89.17 | 85 | 88.33 | 94.17 |

Transferability of the method is an important aspect in building hand-held Raman clinical instrument. The cross validated calibration results of blood glucose data from human subjects and $R^2$ has been reported as 0.87.

Continuous glucose monitoring involves the use of a handheld or wearable device because of the frequency of measurements necessary. The use of fiber probe-based instruments provide for flexibility and anatomic accessibility. In a preferred embodiment the combination of AOTF for wavelength selection and APD, is a preferred embodiment that can be implemented provide a portable system having reduced weight and size. Thus, a preferred embodiment of the present invention relates to a handheld Raman spectroscopic system based on wavelength selection using non-linear calibration. The use of SVM in glucose monitoring is further described in I. Barman et al., "Development of Robust Calibration Models Using Support Vector Machines for Spectroscopic Monitoring of Blood Glucose," Anal. Chem., 82, 9719 (2010), the entire contents of which is incorporated herein by reference. Further details can also be found in I. Barman et al., J. Biomed Opt. 16, 011003 (2010) the entire contents of which is incorporated herein by reference.

A first embodiment for substituting a compact detection system for the dispersive spectrograph-CCD combination, employs a set of optical bandpass filters with corresponding photo-detectors. However, this approach is feasible only when a limited number of bands (spectral points) are sufficient to provide clinical accuracy in spectroscopic predictions. In multi-component mixtures, such as in biological samples, this is rarely possible as illustrated by FIG. 2, where reduction of sampled spectral points below 300 results in a steep rise in prediction error. The application of tunable filters, such as liquid crystal tunable filter (LCTF) or an AOTF, circumvents the need for individual bandpass filters by electronically modulating the transmission band. In a typical wavelength-selective liquid crystal tunable filter, a stack of fixed filters are used that employ interwoven birefringent crystal/liquid-crystal combinations and linear polarizers. The spectral region passed by LCTFs is dependent upon the choice of polarizers, optical coatings, and the liquid crystal characteristics. On the other hand, AOTFs are solid-state optical band pass filters that can be tuned to a desired wavelength by varying the frequency of ultrasound propagating through the device medium.

This rapid tunability and appropriate transmission band selection of the aforementioned filters can be employed in two embodiments for a miniaturized Raman clinical device: tunable laser excitation with fixed wavelength detection shown in FIG. 6 and a fixed laser line excitation with tunable detection shown in FIG. 7. Note that these systems operate by changing either the excitation or detection wavelength while keeping the other constant, which results in acquisition of the same Raman bands (as Raman shift is a measure of the change in photon emission energy from that of the excitation source). An important difference between these embodiments and the conventional spectrometer-CCD systems is that while the latter can be used to acquire spectral information at all wavelengths simultaneously, these embodiments only allow serial sampling of the selected wavelengths. However, when the filters are used in conjunction with an APD which provides 3 to 4 orders of magnitude signal amplification, the serial acquisition process can be implemented in a fast time domain so that acquisition times are less than 1 minute, preferably in a range of about 20 seconds. The serial sampling of the preferred embodiments does not necessitate additional acquisition time as compared to the conventional spectrograph CCD combination. By using a smaller set of wavelengths, spectra of equivalent SNR can be acquired in a shorter period of time.

Figure 6A:
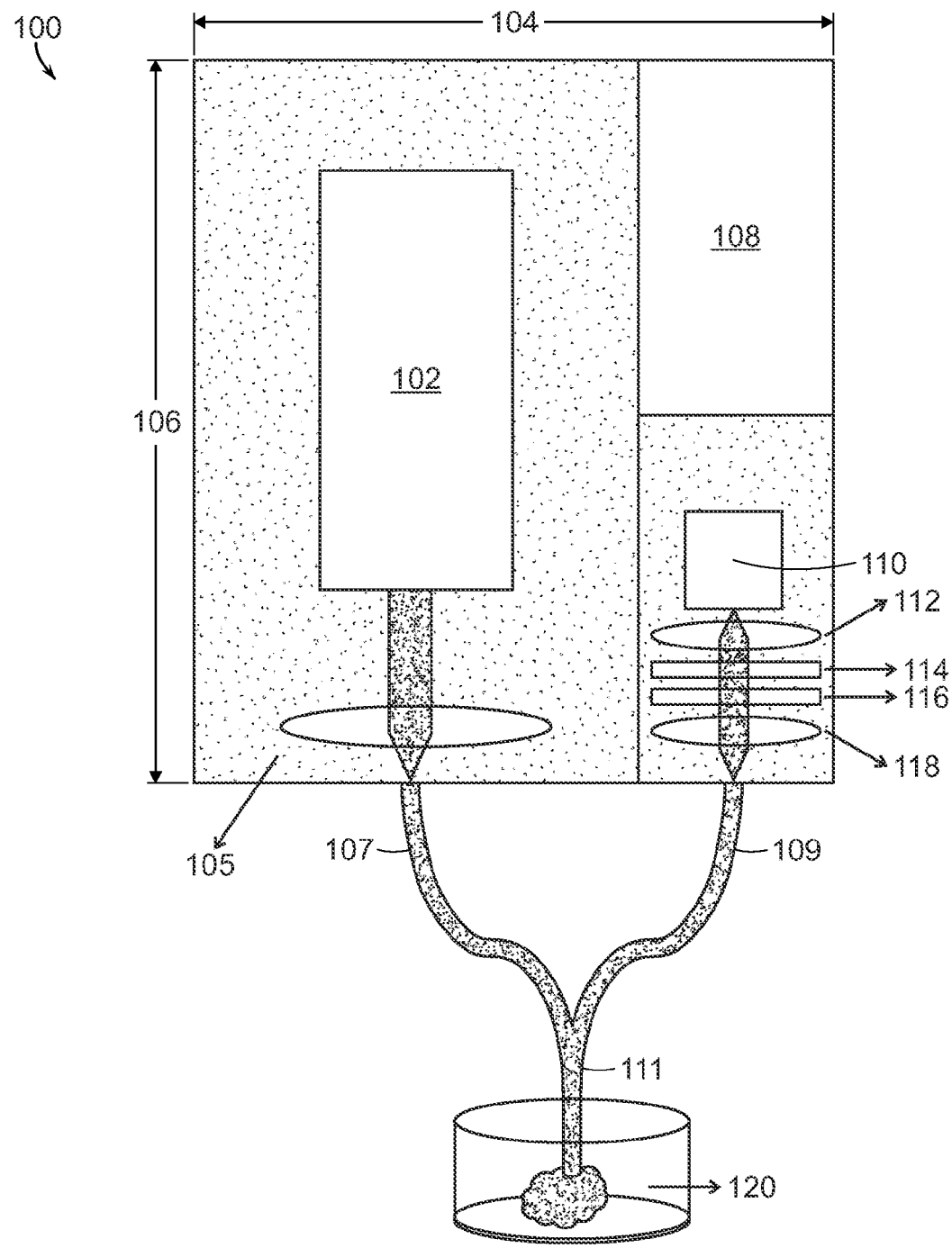
FIG. 6A illustrates a handheld instrument using single-wavelength excitation and multi-wavelength light collection.

The embodiment of FIG. 6A comprises a housing 100 that encloses a tunable light source 102 with a lens 105 that couples Raman excitation light into the delivery fiber 107 of a fiber optic probe 111. Light returning from the tissue or biological sample 120 through one or more collection fibers 109. Light exiting the proximal end of the fibers 109 can be coupled by lens 118 through a combination of two bandpass filters 114 and 116 before lens 110 focuses the collected light onto photodiode 110. These provide for transmission of selected bands and rejection of Rayleigh scattering. The housing 100 contains a controller circuit 108 or computer that is programmed with a software module to implement a control sequence that triggers the laser at selected wavelengths and time intervals to generate the selected Raman spectral bands. This system can also perform chemometric calibration and classification that is appropriate for the application of interest such as the detection of microcalcification found in breast tissue or for blood glucose monitoring, for example.

Figure 6B:
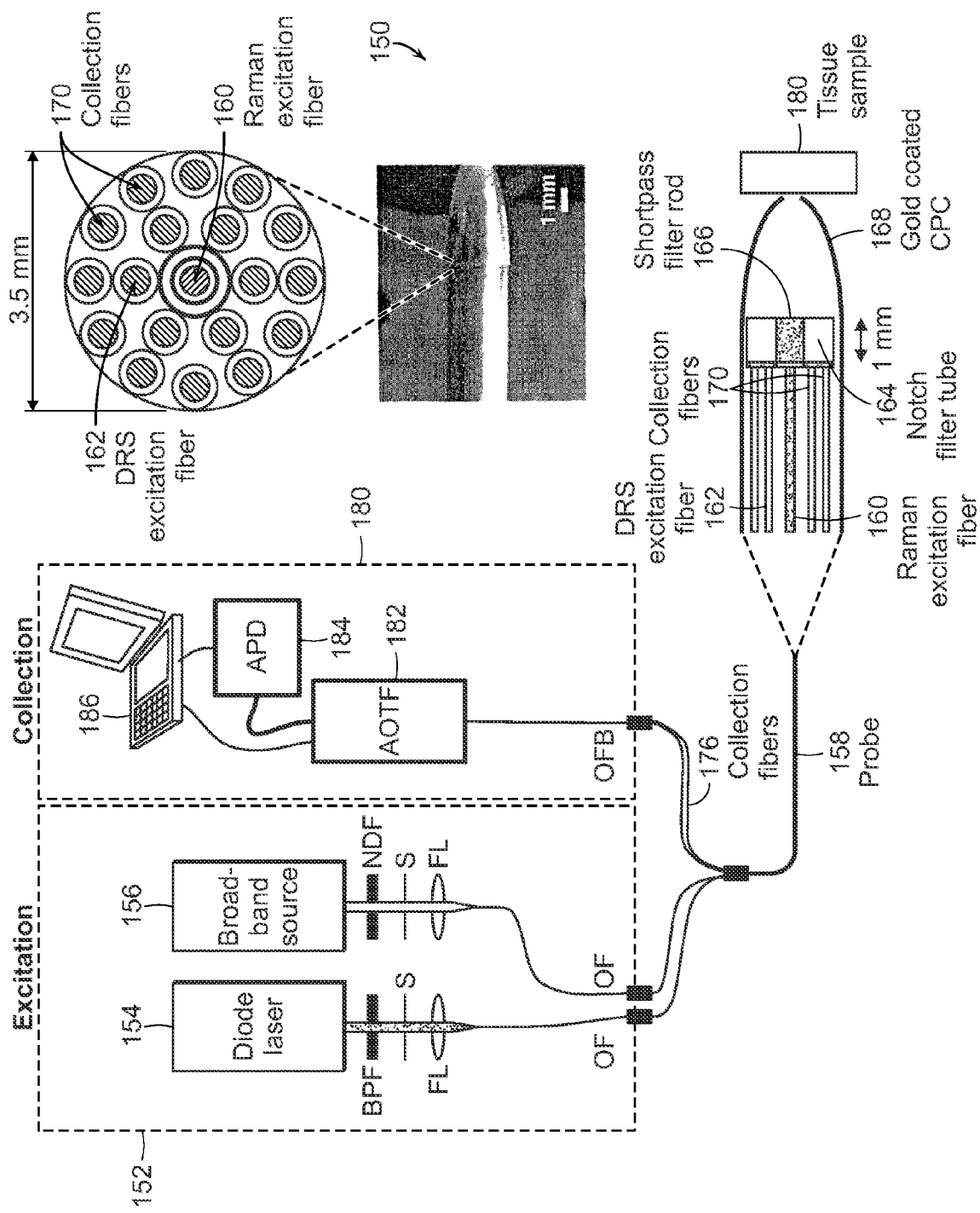
FIG. 6B illustrates another preferred embodiment of a diode laser and broadband light source system coupled to a fiber optic probe and adjustable wavelength detector system.

Shown in FIG. 6B is a preferred embodiment of a Raman measurement system 150. The system 150 includes a light source system 152 including a diode laser 154 and optionally also includes a broadband light source 156 for reflectance measurements of tissue 180. Filters (BPF, NDF), shutter(s) and lenses (FL) couple light into the delivery optical fibers 160, 162 of the probe. The expanded view of the distal end of the probe 158 shows a distal filter system including a short pass filter rod 166 and a notch filter tube 164, a CPC 168 and collection fibers 170. The detector system 180 includes an AOTF 182 to select the wavelengths for detection by photodiode detector 184. The computer 186 includes a processor that processes spectral data as described in the present application and can also controls system operation.

Figure 7A:
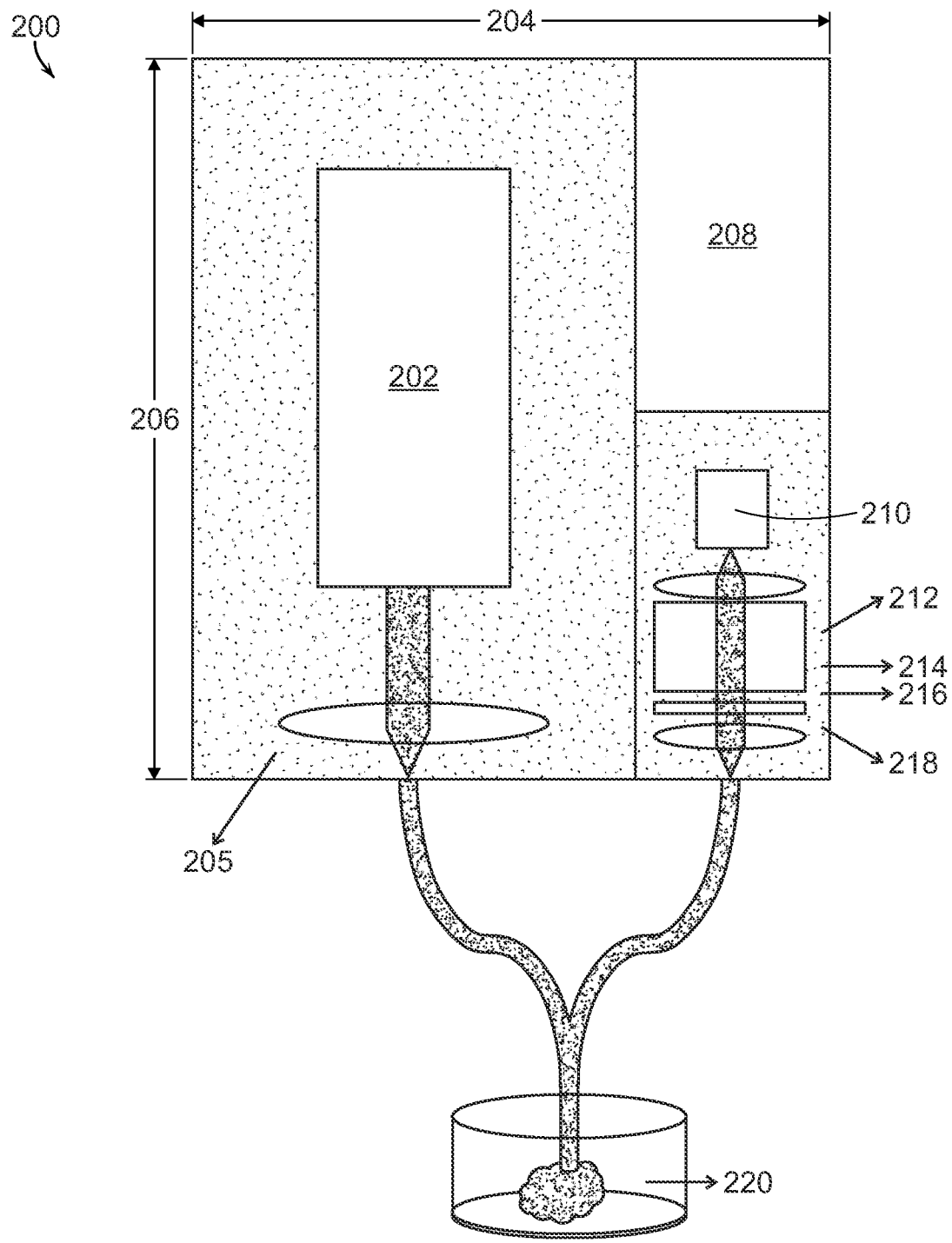
FIG. 7A illustrates a preferred embodiment using multi-wavelength excitation source with a single detector.

In FIG. 7A, a single wavelength source is used, such as a diode laser 202, within a housing 200. The output power of the source is stabilized. Excitation light is coupled by lens 205 to a fiber optic probe as described in the present application. The collected Raman light is coupled by lens 218 to notch filter 216, tunable filter 214, and lens 212 for detection by photodiode 210.

Furthermore, the use of tunable sources or/and detectors facilitate the application of the same instrument for multiple diagnostic applications since the selection of wavelengths does not necessitate a change in the hardware such as selection of optical bandpass filters.

Figure 8:
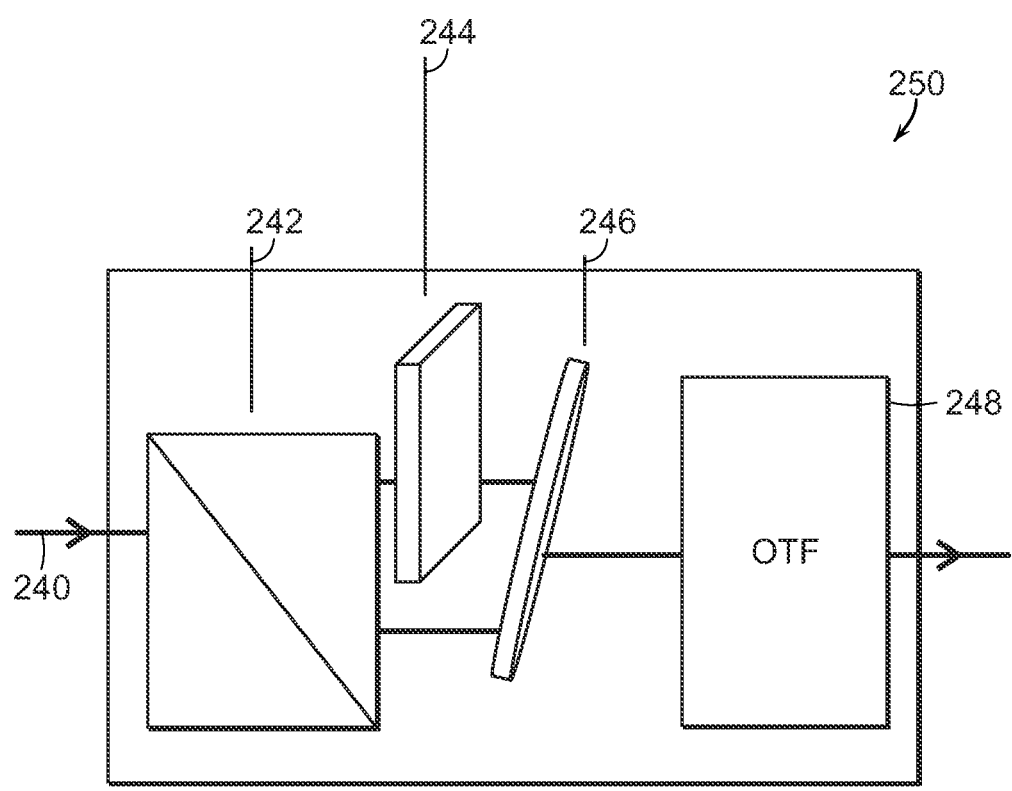
FIG. 8 illustrates a preferred embodiment of a sweeping source system with a polarization controller in accordance with a preferred embodiment of the invention.

Typically, AOTF are polarization-sensitive and the light back scattered by the sample will have mixed polarization components. This can be addressed by compensating using a polarization controller 250. As seen in FIG. 8, light from the sample 240 is split using beam splitter 242. A first beam is directed through a half wave plate 244. Both beams are directed through a polarizer 246 onto the AOTF 248. Light exiting the AOTF 248 is then coupled to the detector.

Figure 7B:
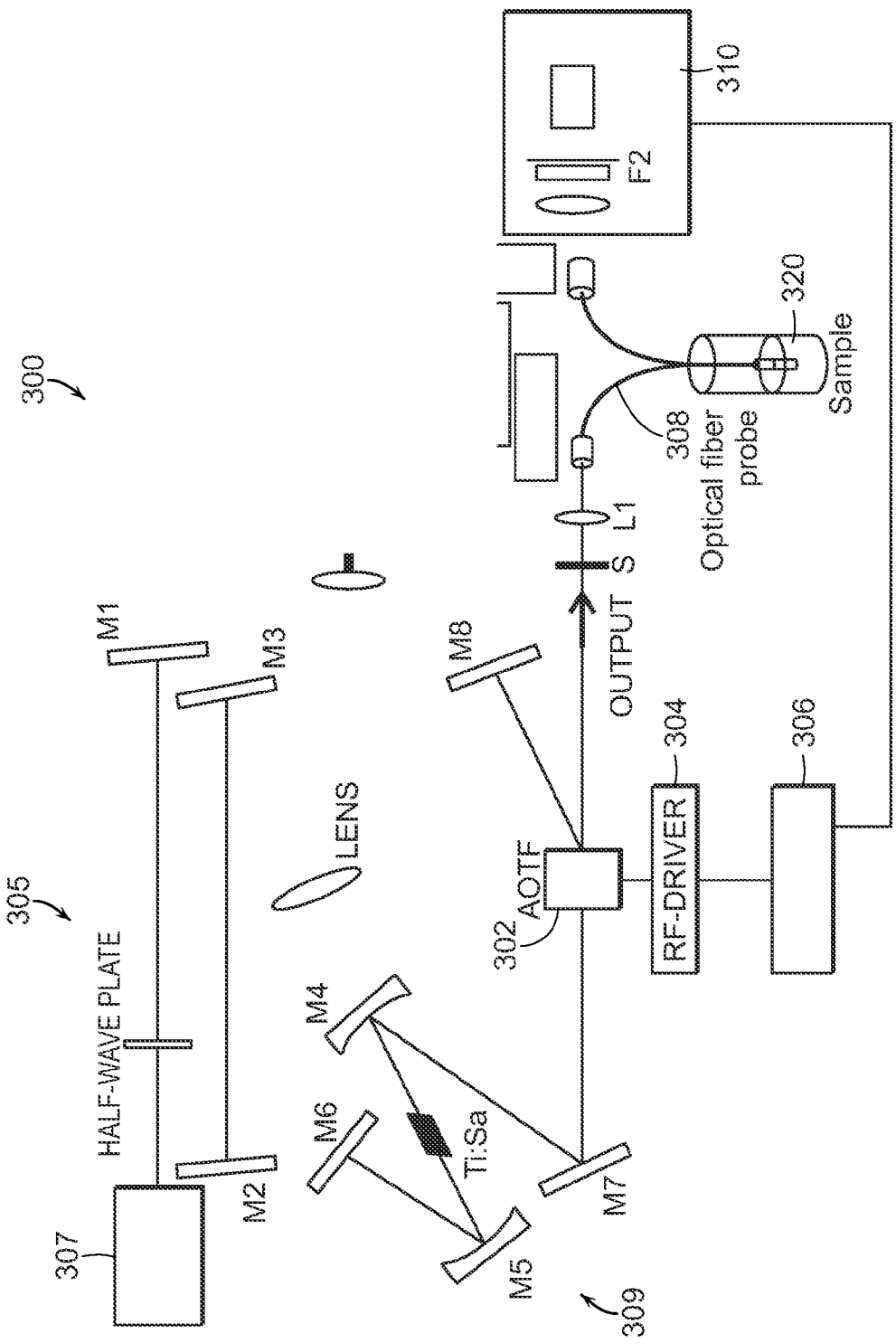
FIG. 7B illustrates an example of a sweeping source with a single detector.

An embodiment of a system using a tunable system is shown in FIG. 7B. In this embodiment a tunable laser system has an AOTF in the cavity to generate an excitation wavelength over a range of 755-855 nm. A tunable filter controlled by 306 computer delivers a selected output wavelength through fiber optic probe 308 to illuminate a sample. Several types of wavelength tunable laser sources can be used. A sweeping wavelength source can use a combination of dispersive optical elements, such as gratings, and mechanical components, such as a polygonal mirror or galvano mirror, inside of the laser cavity. A Fabry-perot tunable filter can also be used. A semiconductor source with an optical amplifier can also be used as a sweeping source. In the embodiment of FIG. 7B, a pump laser source 307 operating at 532 nm is coupled into the cavity 309 of a Ti:Sa laser. An AOTF 302 (or other switching element) situated in the cavity provides for sweeping across a range of 755 nm to 855 nm. Further details regarding this source can be found at Kodack et al., "Wavelength swept Ti:sapphire laser," Optics Communications 281 (2008) 4975-4978, the contents of which is incorporated herein by reference. The RF-driver 304 is controlled by computer 306 that is also connected to the detector assembly 310 as described herein. The probe 308 can be used to measure a tissue sample 320, or mammalian tissue.

One embodiment includes a rotating optical filter wheel with a single photodiode. During signal acquisition, the filter wheel is rotated to collect the signals corresponding to the specific Raman bands at the single photodiode.

Figure 7C:
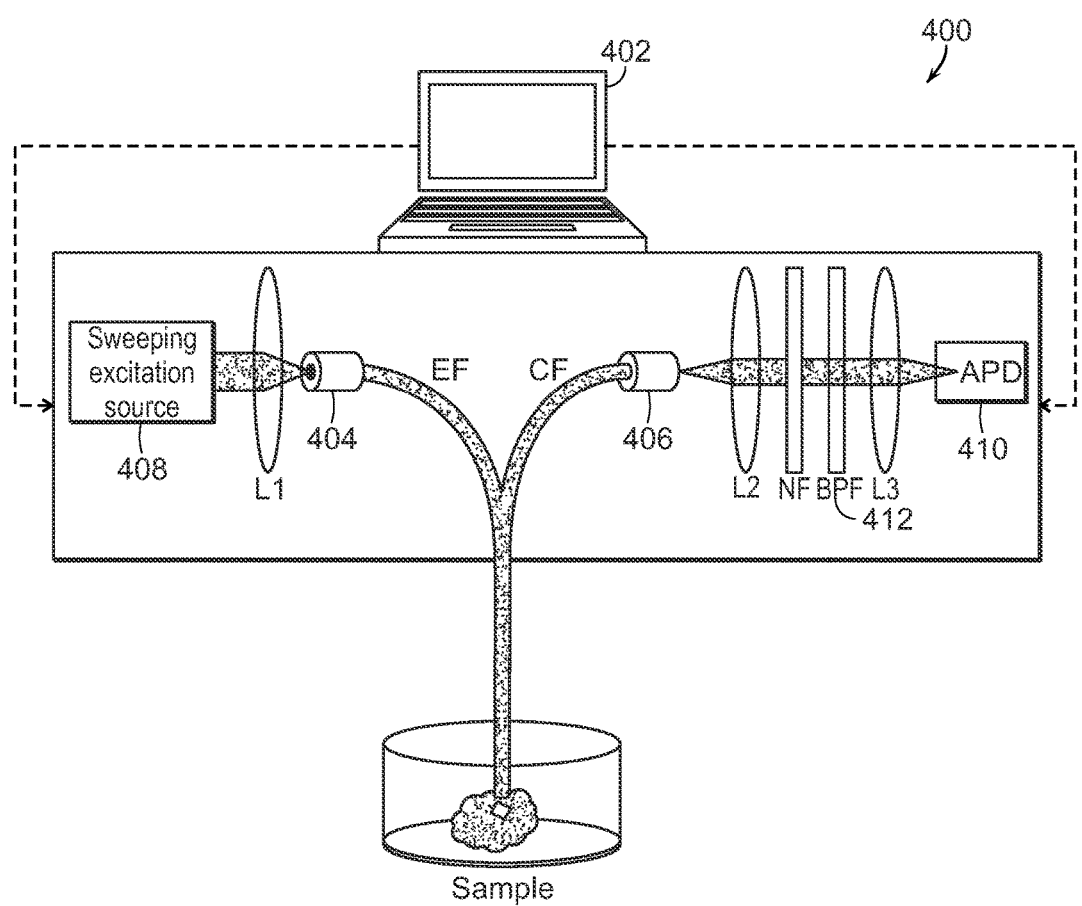
FIG. 7C illustrates a preferred embodiment a system using a sweeping source and a tunable filter.

In the embodiment of FIG. 7C, a sweeping source 408 is controlled by computer, PDS or other handheld computing device 402 to deliver light into a fiber coupling 404 to illuminate a sample. Light collected from the sample, or patient, is directed from emission coupler 406 through collection optics as described herein to APD 410. A tunable filter, or band pass filter 412, can be used to filter light being detected.

Figure 7D:
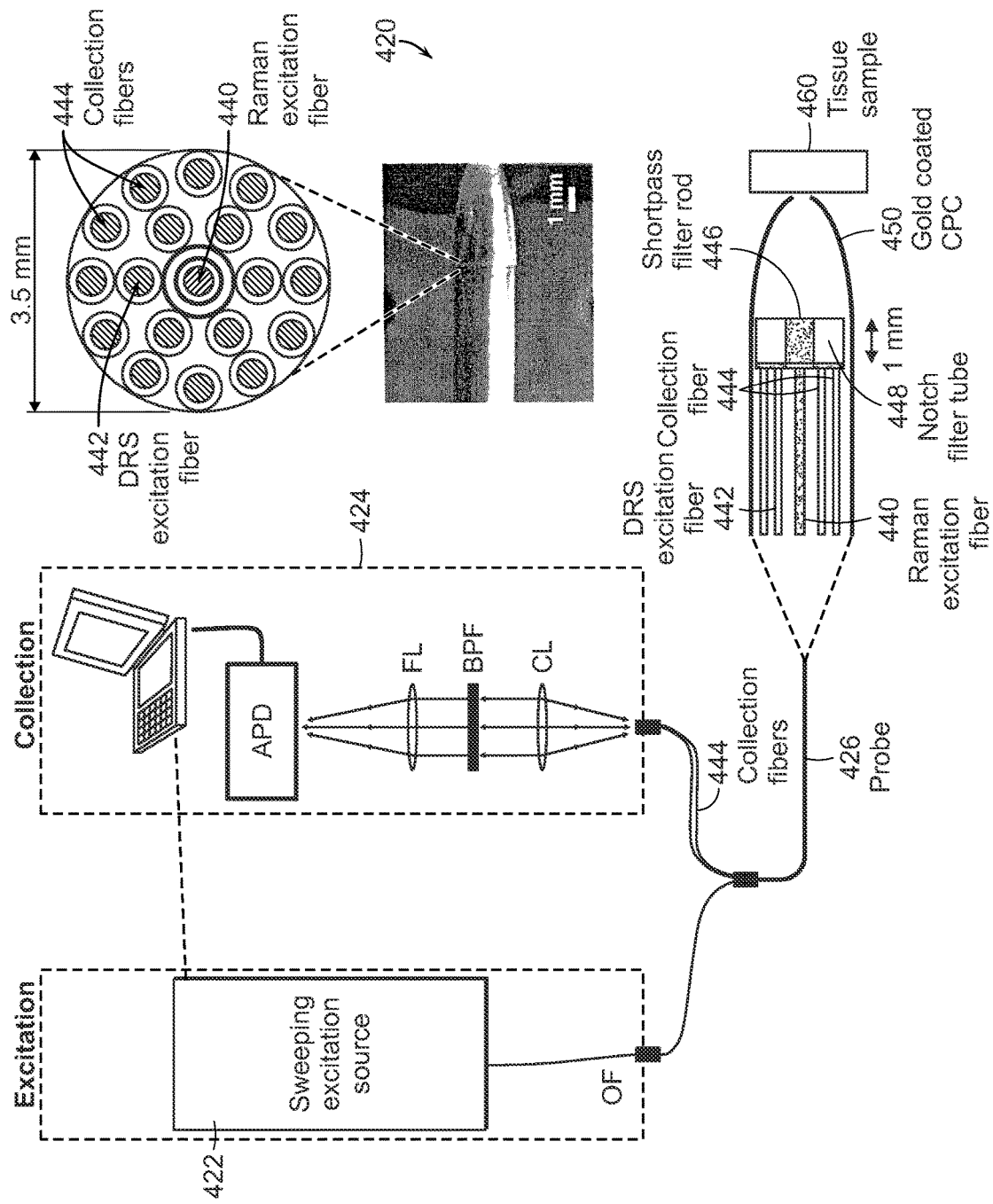
FIG. 7D shows a scanning wavelength source coupled to a fiber optic delivery and collection system and a photodetector for detecting Raman spectral data.

A preferred embodiment of a system 42 using a tunable source 422, a fiber optic probe 426 and a detector system 424 is shown in FIG. 7D. The distal end of the probe 426 includes a central Raman delivery fiber 440, an optional diffuse reflectance delivery fiber 442, surrounding collection fibers 444, a short pass filter rod 446 that filters the Raman excitation light, a notch filter tube 448 that filters the light being collected and an optical concentration (CPC) 450 for coupling light onto the tissue 460 and providing improved light collection efficiency.

Utilizing multiple lasers with a single band pass filter and photodetector is another approach for miniaturizing the device. In this embodiment, the system uses several laser diodes emitting light at different respective wavelengths. Several laser diodes excite different spectral regions (spectral bands vary between diagnosis of breast cancer, cervical cancer, malaria and diabetes) and employ only a single photodetector to get spectral information. These spectral regions can be selected using wavelength selection methods discussed above.

Coupled with a small diode laser and a fiber optic probe for excitation and collection, and a detector array, can be used in a hand-held Raman unit having extensive applications in the field of disease diagnostics, as well as in analytical and bio-analytical chemistry. For example, a miniaturized Raman system can be employed as a non-invasive continuous glucose monitor. The device can be worn around the wrist or around the waist, as is the case for the electrochemical minimally invasive sensors. Another potential application is the use of a miniaturized Raman system for testing withdrawn blood samples for glucose levels.

The fiber optic probe of a preferred embodiment of the invention can comprise a Raman probe as described in U.S. Pat. No. 7,647,092 and also in U.S. patent application Ser. No. 10/407,923 filed on Apr. 4, 2003, this patent and application being incorporated herein by reference. Preferred embodiments of a fiber optic probe are illustrated in connection with FIGS. 9A and 9B.

The probe 500 can include an outer tube 520 extending along the length of the probe and forming a seal with the distal optical delivery and collection system. A preferred embodiment of this system uses compound parabolic concentrator (CPC) 520 to increase the collection efficiency of the system. An example of this system for a probe that is about 2-4 mm in diameter can be coupled to a CPC having a distal opening 512 that is 0.8 mm in diameter, a proximal opening 514 that is 3.64 mm in diameter, and a length of 9.85 mm. The inner surface can be coated with a reflective metal surface 511, such as gold. The inner surface 511 has a parabolic shape configured to increase optical efficiency by reflecting the returning light onto a plurality of rings of collection fibers 504. The rings can extend around a central delivery fiber or fiber bundle 502, and can include two, three or more rings to increase the collection efficiency within the space available. By using a larger number of small diameter fibers, the packing factor and thus collection efficiency, can be increased.

The CPC can be filled with a transmissive dielectric material, such as an acrylic. The optical concentration can thus be molded with such a transparent dielectric material where total internal reflection at the air-dielectric interface to obtain the reflective surface. For a fill material having a refractive index $\eta$, the maximum concentration ratio of the CPC is $\eta^2/\sin^2\theta$ where $\theta$ is the maximum output angle of light being directed out of the proximal end of the CPC for collection.

As seen in the cross-sectional view of FIG. 9B, the central delivery fiber 502 directs light through a distal filter rod 506 having a filter layer formed on the distal end of the collection fibers that receive light through a distal collection tube 508 which has a filter 509 formed on the proximal end to filter the collected light. This system can also be adapted for use with an optical fiber 522 for the delivery of broadband light to provide for collection of diffuse reflected light. The filter rod 506 can have a diameter 505.

Figure 9C:
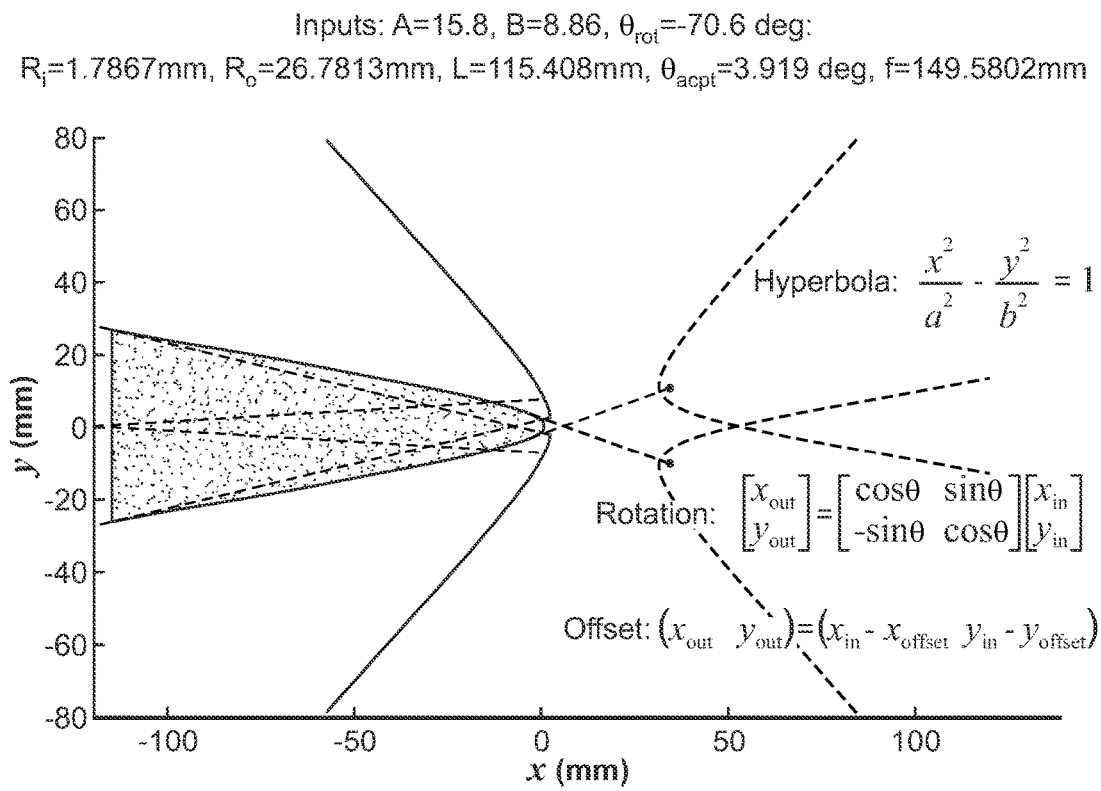
FIG. 9C illustrates the hyperbolic design parameters for a CHC.
Figure 9D:
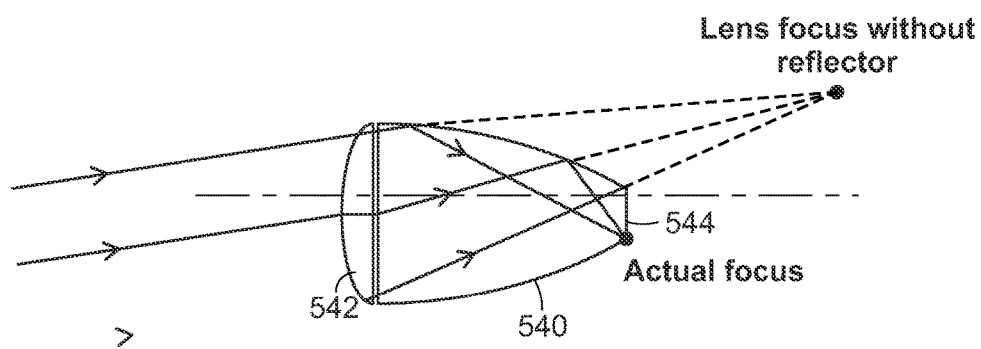
FIG. 9D illustrates a CHC with a matching proximal lens.
Figure 9E:
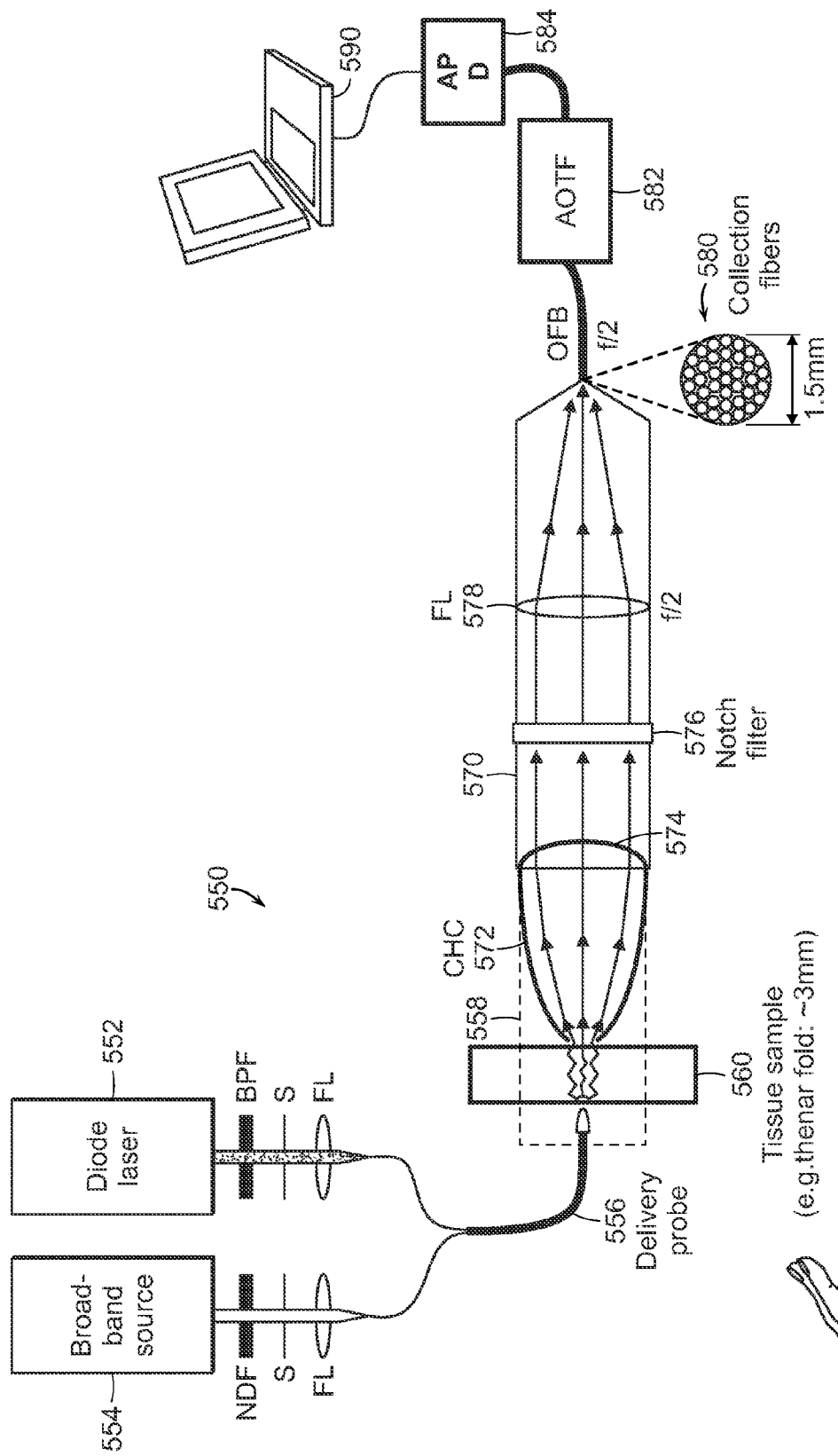
FIG. 9E illustrates the use of a CHC in a transmission Raman system for glucose measurement.

FIGS. 9C-9E illustrate a system using a compound hyberbolic concentration. A compound hyperbolic concentrator (CHC) is non-imaging optical concentrator that efficiently collects the light emanating from highly scattering biological tissues while using optical systems with very low numerical apertures (NA). Unlike a compound parabolic concentrator (CPC), a CHC allows for the collimation of scattered light directions to within extremely small range of angles while also maintaining practical physical dimensions. Such a design allows for the development of a very efficient and compact spectroscopy system for analyzing highly scattering biological tissues.

Many optical systems can receive light at only a limited range of angles specified by their numerical apertures. In addition, efficient light collection is crucial for a tissue Raman spectroscopy system due to the inherently weak nature of Raman scattered light. For this reason, spectroscopic instruments used for the analysis of biological tissues often require a light collection device that redirects the scattered light entering at steep angles to be within a limited range of angles with respect to the receiving optical system. This had been previously achieved with great efficiency by the use of a CPC. However, the CPC length becomes impractically long if a low numerical aperture is desired. For example, certain dielectric coatings on optical filters are effective only at a very limited range of incident angles. The present embodiment of the invention uses of a CHC to efficiently collimate the direction of light scattered at wide angles from biological tissues into a very low numerical aperture while maintaining practical physical dimensions.

The CHC reflector surface is defined by rotating the curve formed by two tilted and offset hyperbolas with the input aperture defined by their foci (FIG. 9C). It is analogous to the CPC where the curve is similarly formed by two parabolas. However, in addition to the reflector, the CHC 540 is also coupled with a matching focusing lens 542 with the focal length defined by the distance between the output aperture and the focus on the opposite side of the symmetric axis of the hyperbola (FIG. 9D). This combination effectively causes the CHC to function as a CPC with a much longer longitudinal dimension. The CHC surface is polished to optical grade (0.3 micron) finish and coated with the appropriate reflective material optimized for the desired wavelength. The focusing lens is coated with an antireflective coating appropriate for the applicable wavelength. Using computer-controlled machining and electroforming techniques, a 0.06 NA CHC with a 4 mm diameter input aperture 544 was fabricated at a length of about 12 cm. (A CPC with the same NA and input aperture would require the length to be 4 times longer.) The incident light entering the CHC at a steep angle (up to +/−90 degrees to normal) exited the CHC at angles within +/−3.4 degrees to normal. With appropriate modifications in the design, even smaller range of angles can be achieved. The collimated light can then be filtered, focused and collected with ease, even in optical systems with very limited range of acceptable angles. This CHC was used to collect of human skin Raman spectra on a portable transmission-mode Raman spectroscopy system 550 as shown in FIG. 9E. Besides collection of Raman spectra from skin tissues in transmission mode, the proposed CHC design can have many other uses in spectroscopy systems requiring efficient collimation of nearly isotropically scattered light as, for example, from biological tissues.

The system 550 can include a diode laser 552 as described herein, an optional broadband source 554, along with suitable filters (BPF, NDF) shutter(s) and lenses (FL) to couple excitation light into a delivery probe. The probe 556 can be aligned with a light collection system 570 using a housing 558. This system can be used, for example, to transmit light through tissue 560, such as the thenar fold of the human hand. A CHC 572 within the housing 570 collects transmitted light and with lens 574, filter 576 and lens 578 couples the light into a collection fiber bundle 580. An AOTF 582 can be used to select wavelengths of light to be detected by detector 584. A system processor and controller 590 can be used to process spectral data and operate the system as described herein.

Figure 10:
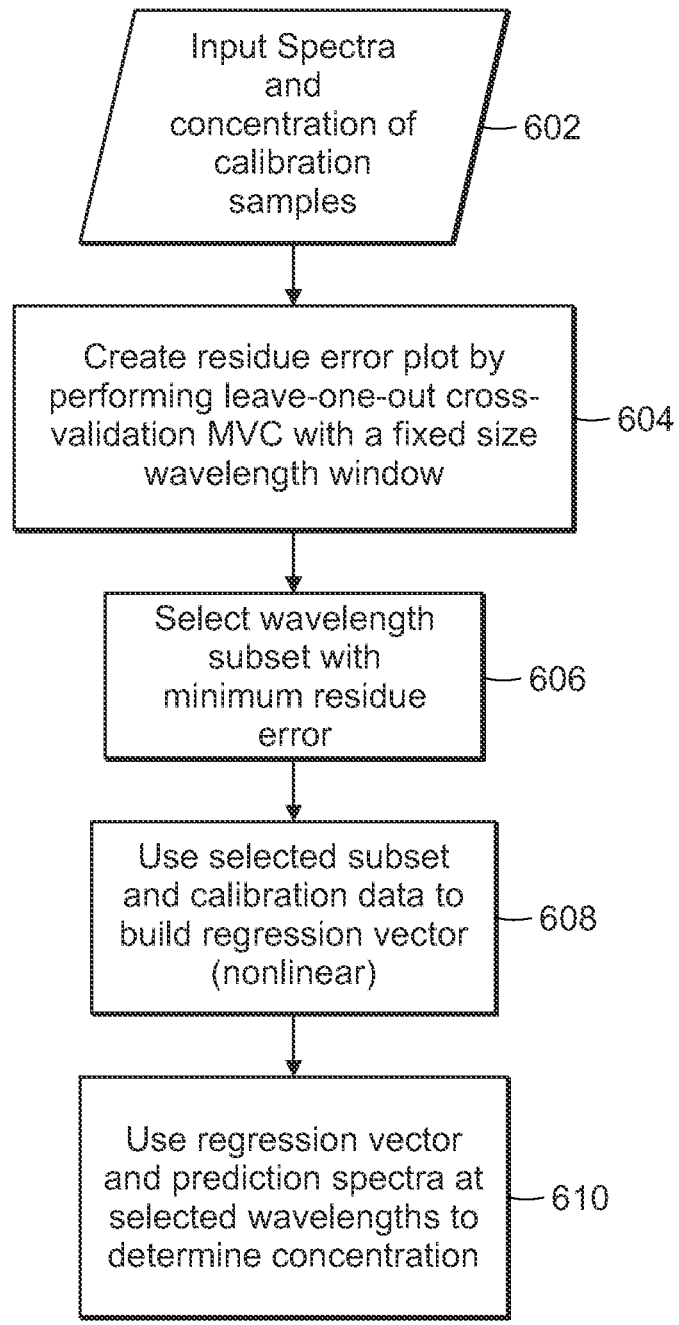
FIG. 10 illustrates a process sequence for a method of wavelength region selection.

Shown in FIG. 10 is a process 600 for selecting wavelengths using a non-linear selection process. Spectra used for wavelength selection are input 602 into the processing sequence. The concentration of calibration samples can be selected from data stored in memory. Using leave one-out cross-validation from a fixed of wavelength window a residue error plot can be created 604. The number of wavelengths is selected 606 to reduce the error to a desired level. These selected wavelengths are then used 608 to construct a regression vector (non-linear) which is then used with reference 610 spectral data to determine the concentration of one or more analytes.

Figure 11:
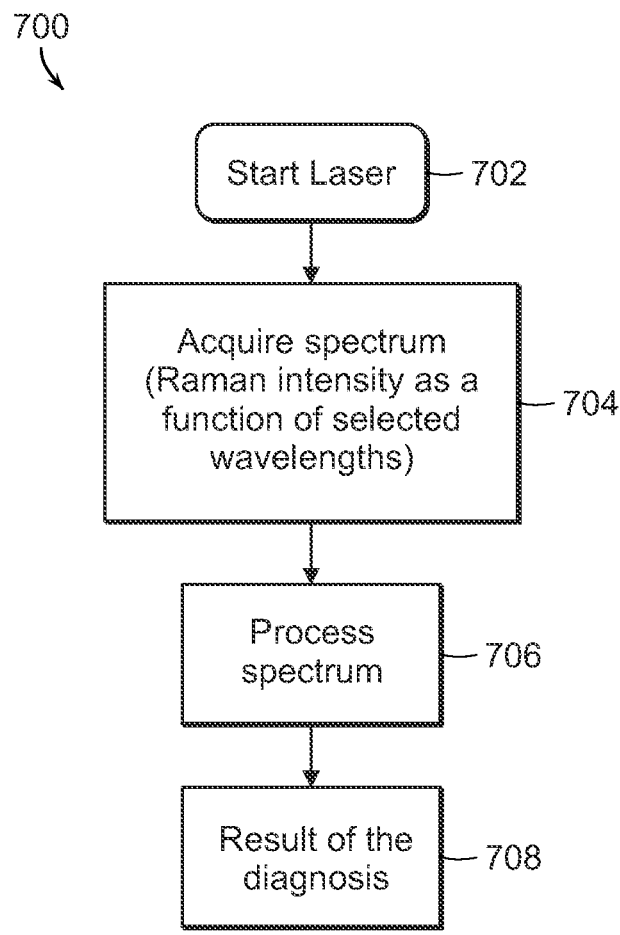
FIG. 11 illustrates a process sequence for a diagnostic measurement in accordance with preferred embodiments of the invention.

A process 700 for using the resulting spectral bands is then implemented as shown in FIG. 11. The light source, such as a laser, is actuated 702 to acquire 704. The desired spectrum using the systems described herein. The spectrum is then processed 706 to provide a diagnostic result 708.

Figure 12:
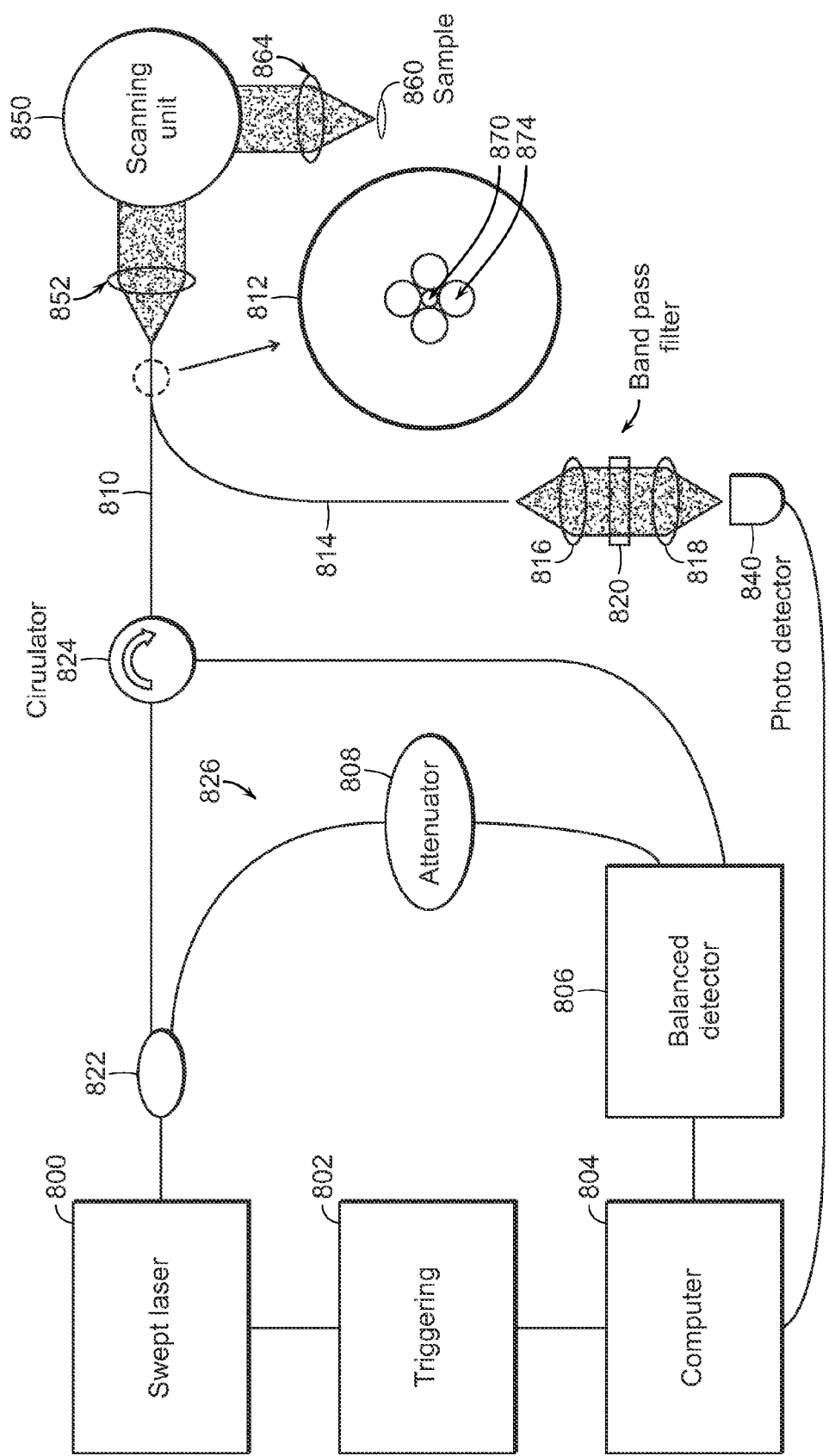
FIG. 12 illustrates a combined Raman and optical coherence tomography system.

A preferred embodiment of the invention uses single sweeping source both for optical coherence tomography (OCT) and Raman light collection. This system provides both morphological and chemical information from the tissue as illustrated in FIG. 12. Using a single sweeping source 800 that is coupled to an optical fiber coupling 812 with optical fiber 810 which is centrally located relative to a surrounding plurality of light collection fibers 814. A pair of lenses 816, 818 are used to couple the collected light through a band pass filter 814 and detector 840. A processing system or computer 804 is programmed with a software module to govern a control system 802 that triggers the laser 800 at selected wavelengths and time intervals corresponding to the selected spectral windows. A fiber splitter 822 separates a reference path 826 to attenuator 808 and first detector 806. A circulator 824 sends a second reference signal to the detector 806.

The fiber coupler 812 delivers light through lens system 852 to a scanning system 850 which scans the sample 860 at different angles using delivery optics 854. The simplicity of the combined system can be integrated in a small catheter for in-vivo diagnosis. The combined system may be useful for diagnosis of the cardiovascular system (ex. coronary artery), gastrointestinal tracts (ex. esophagus and colon).

Many factors can affect wavelength selection and the accuracy and specificity of the measurement. One problem in the measurement includes the effects of photobleaching of the tissue. Other problems include the time lag in exchange between interstitial fluid and blood as described in Barman et al., "Accurate Spectroscopic Calibration for Noninvasive Glucose Monitoring by Modeling the Physiological Glucose Dynamics," Anal. Chem. 82, 6104 (2010), the entire contents of which is incorporated herein by reference.

One of the primary hurdles in attaining the aforementioned calibration transfer is the presence of a varying luminescence (fluorescence) background. Additionally, the significantly greater intensity of the tissue fluorescence frequently limits analysis to strong Raman bands only. The associated photon shot noise and detector noise, which may have intensities similar to that of the Raman signal depending on the signal acquisition times, further compromise the diagnostic capability of the spectroscopic technique.

More importantly, in biological measurements, quenching (photobleaching) of the endogenous fluorophores can change the acquired signal appreciably over time. In the context of the present application, photobleaching can be defined as the reduction in sample autofluorescence intensity over a period of time under sustained laser exposure. A number of different mechanisms, including deactivation of the excited-state fluorophores upon contact with other molecules (commonly known as quenchers) in the tissue or sample, can contribute to the overall drop in fluorescence intensity. In clinical Raman measurements, the biological sample can be subject to a laser beam over a time period varying from a few seconds to several hours. For example, glucose tolerance measurements and glucose/insulin clamping studies in humans and animal can take anywhere between two to six hours. Naturally, fluorescence quenching manifests itself in the Raman spectra acquired over the duration of such measurements.

In order to extract quantitative glucose information from the acquired spectra, it is preferable to employ implicit calibration methods such as partial least squares (PLS) and principal component regression (PCR). These methods require only the concentrations of the analyte of interest and the spectra acquired from the calibration samples to construct a regression model. However, these calibration methods are often misled by chance correlations between non-analyte specific spectral information and the concentrations of the analyte of interest. Spurious effects such as system drift and covariations among sample constituents can lead to apparently functional models, which cannot be successfully employed for prospective prediction.

Photobleaching can introduce spurious correlations in the calibration models for biological Raman spectroscopy, particularly in cases where temporal correlations exist within the concentration dataset. Specifically for the characterization of metabolic activity of the blood glucose regulation system, functional measurements, such as glucose loading or glucose tolerance measurements, are frequently performed where the blood glucose levels are changed by ingestion of glucose or insulin. To establish the clinical use of Raman spectroscopic measurements spectra are typically acquired over the duration of these studies to form a calibration system (in conjunction with the measured analyte concentrations) for prospective prediction of blood glucose levels. Consider first the robustness (and validity) of models developed on samples undergoing photobleaching during glucose tolerance tests. Using numerical simulations and measurements on physical tissue models. A significant deterioration in prospective prediction accuracy is observed when the model is developed on "correlated samples", i.e. calibration samples that demonstrate statistically significant correlation between (photobleached) fluorescence levels and glucose concentrations, compared to when it is developed on "uncorrelated samples." This is attributed to the construction of a spurious calibration model where the regression vector is partly based on the fluorescence signal rather than only on the analyte of interest (glucose). This result has major implications for diabetics, as any tolerance measurement based protocol can lead to an approximately monotonic rise in glucose levels over the measurement period due to the inadequate insulin response. Evidently, the resultant covariation between the glucose concentrations and the photobleaching-induced decay in the tissue auto-fluorescence levels may lead to systematic errors in the calibration model.

The present embodiment of the invention uses fluorescence removal methodologies as tools for avoiding the pitfalls associated with photobleaching. Removal of fluorescence to isolate the Raman bands can include several methodologies including time-gating, derivative processing, least squares polynomial subtraction, shifted excitation Raman difference spectroscopy (SERDS) and shifted subtracted Raman spectroscopy (SSRS). SERDS, which is based on the differential shift response of the Raman and fluorescence signals to the shift in excitation wavelength does not suffer from insufficient photon collection problems (as opposed to the time-gating schemes) and does not, in principle, introduce spectral artifacts like the numerical post-processing techniques. A tunable laser source (or two different sources at different wavelengths) is employed to obtain the sample spectra at two shifted excitation frequencies, which are then subtracted to eliminate the fluorescence background, leaving only the Raman component as first derivative signals. SSRS is similar to the SERDS method, except that it involves shifting the spectrograph grating instead of the laser frequency. SERDS and SSRS can be used successfully to reconstruct "intrinsic" Raman spectra from simple mixture models, however, efficacy in quantitative problems of concentration prediction particularly when used in conjunction with an implicit calibration method has not been analyzed. The following compare the effectiveness of SSRS to numerical post-processing techniques, namely least squares polynomial subtraction and spectral derivative application, for both photobleaching correlated and uncorrelated samples. By exploiting the shifted Raman spectra in SSRS to reject the fluorescence background, this reduces the prospective prediction errors for the calibration models developed on the correlated samples to the levels of the models calibrated on uncorrelated samples.

Figure 13A:
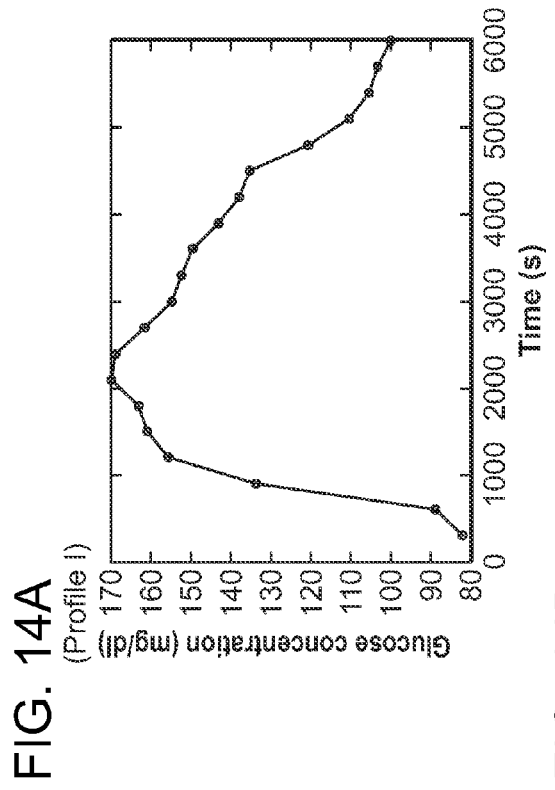
FIGS. 13A-13B illustrate Raman spectra acquired from a human volunteer during an OGTT, and a normalized tissue autofluorescence decay ($I_\lambda/I_{exc}$) obtained as a function of time during the OGTT performance (the measured data points are in circles and the dotted line is the best fit double exponential curve), respectively.
Figure 13B:
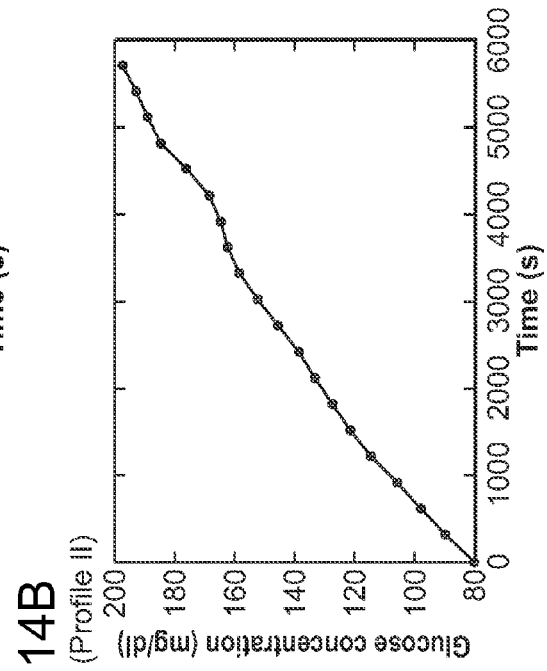

The concentration datasets as well as the tissue fluorescence and photobleaching profile used in the numerical simulations A. Enejder et al., "Raman Spectroscopy for Non-invasive Glucose Measurements," Journal of Biomedical Optics 10(3), 031114 (2005) incorporated herein by reference and in the previously incorporated patent applications. Briefly, NIR Raman spectra were acquired from the forearms of twenty human volunteers undergoing oral glucose tolerance tests (OGTT). An 830-nm diode laser (Process Instruments) was used for Raman excitation and the back-scattered light from the tissue was collected on a liquid-nitrogen cooled CCD (Roper Scientific) coupled to a f/1.8i spectrograph (Kaiser Optical Systems, Inc.). For each volunteer, spectral measurements were initiated following the ingestion of a 220 ml SUN-DEX solution (Fisher Hamilton LLC) containing 75 g of glucose. Spectra were acquired for a total of 3 min per data point at 5 min intervals over approximately a two hour time period forming a measurement time series for each volunteer. A representative spectral time series acquired from a patient is shown in FIG. 13A. The second panel, FIG. 13B, gives the photobleaching profile as measured on this volunteer. It is a curve of $I_\lambda/I_{exc}$ as a function of time, where $I_\lambda$ is the area under the spectral curve over a 20 $cm^{-1}$ band surrounding any arbitrarily selected central value (600 $cm^{-1}$ used for data shown here) and $I_{exc}$ is the measured intensity of the excitation source. The measured values of $I_\lambda/I_{exc}$ were fitted with a double exponential curve, as shown in FIG. 13B.

Figure 14A:
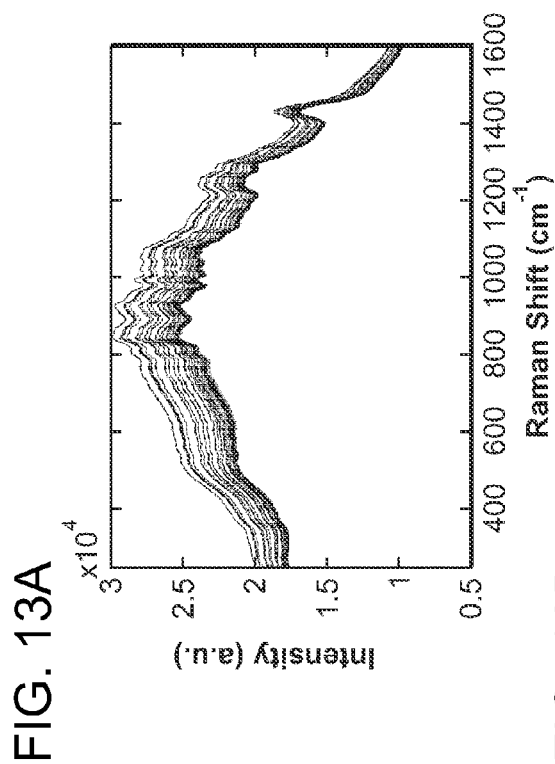
FIGS. 14A and 14B representative glucose concentration profiles taken from two human patients Profile I (FIG. 14A) and Profile II (FIG. 14B).
Figure 14B:
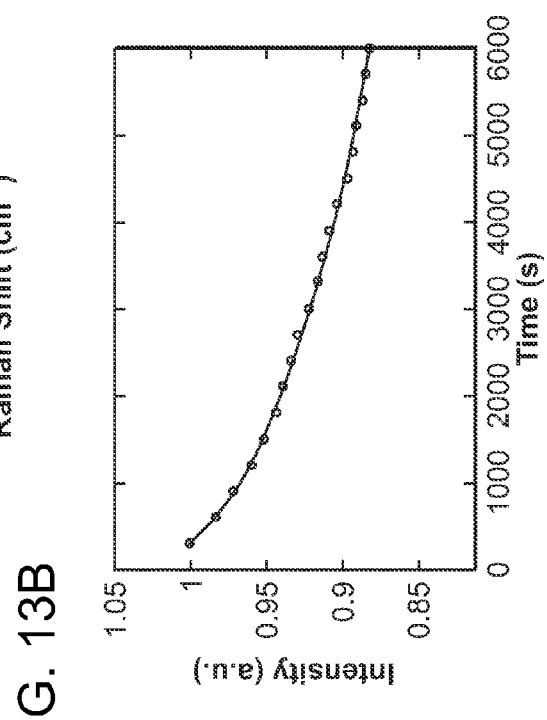

Concomitant with the spectral measurements, blood samples were also collected using finger sticks at regular 10 min intervals for estimation of glucose levels by a clinical glucose analyzer (HemoCue, Inc.). In order to correlate with the spectral measurements, the reference values were approximated at intermediate time points using spline interpolation. For comparison, two such profiles taken from two different volunteers are shown in FIGS. 14A and 14B. Profile I (FIG. 14A) shows a rise in blood glucose concentration (to almost double its normal value) followed by a return to original levels which is indicative of proper functionality of the blood glucose regulation system in the patient. Profile II (FIG. 14B) in sharp contrast, exhibits a nearly monotonic rise in glucose levels over the test period, characteristic of weak insulin-mediated response in this subject.

Physical tissue models (tissue phantoms) in which the fluorescence and Raman scattering can be precisely varied are used to analyze the prediction performance of calibration models based on the correlated and uncorrelated spectral datasets, respectively. Additionally, in conjunction with the numerical simulations, this application describes the effect of fluorescence removal strategies on the prospective prediction accuracy of the developed calibration models.

A total of 50 tissue phantoms were used with aqueous solutions of glucose (analyte of interest), urea (spectral interferent) and indocyanine green (ICG). ICG was employed to produce a fluorescence background similar to the tissue autofluorescence observed with near-infrared (NIR) excitation. To mimic the (photobleached) fluorescence correlation observed in glucose tolerance testing of human subjects with impaired glucose tolerance (see Profile II in FIG. 14B), 20 tissue phantoms were constructed where the correlation between the glucose and ICG concentrations was high ($R^2 \approx 0.95$). The other 30 tissue phantoms had negligible correlation between the glucose and ICG levels ($R^2 \approx 0.1$). For both correlated and uncorrelated tissue phantoms, glucose and ICG concentrations varied from 0.9 to 1.2 M and 0.18 μM to 0.36 μM, respectively. The relatively high concentration of glucose in the tissue phantoms enabled higher fluorescence values to be analyzed while retaining a satisfactory signal-to-noise ratio. The urea concentration in all the tissue phantoms was randomized in the range of 250 to 400 mM.

For Raman excitation, an 830-nm diode laser was focused into the delivery fiber (200 μm core diameter) of an optical fiber and filter probe assembly to deliver an average power of ~100 mW on a spot size of ~1 mm² at the sample. The sample solution was held in a cylindrical glass vial (1 inch diameter) with a top opening, through which the probe tip was immersed directly into the solution without contacting the container. The back-scattered Raman light was collected by 10 collection fibers (200 μm core diameter) before being dispersed via a tunable f/2.0 spectrograph (LS-785, 5 cm⁻¹ resolution, Princeton Instruments) on to a TE-cooled CCD detector (PIXIS 256, Princeton Instruments). The acquisition time for each Raman spectrum was 20 seconds. Spectra of the phantoms were acquired randomly with respect to the constituents' concentration in order to eliminate any potential temporal correlation. Since the optical fiber probe itself generated prominent Raman spectral features at wavelengths below 800 cm⁻¹, the spectral range of 950 to 1800 cm⁻¹ was used for data analysis (PLS calibration and prediction), after vertical binning and cosmic ray removal. Additionally, in order to investigate strategies for removing the effects of the fluorescence background, SSRS was performed by acquiring the tissue phantom spectra after tuning the spectrograph grating position by ~25 cm⁻¹ (approximately the full width half-maximum of the characteristic glucose peak at 1100 cm⁻¹). The Raman shift axis was calibrated using the standard spectra measured from a 4-acetaminophenol powder sample. The tuning of the grating was monitored by the position of the laser line on the CCD detector such that an 18-pixel shift was maintained between the two positions. The difference between the pair of Raman spectra (acquired at two different grating positions) was used for PLS calibration and prediction, and the performance was compared with that of the PLS calibration model constructed using the raw Raman spectra. First derivative spectra were employed for comparison with the aforementioned calibration models. For the first derivative spectra, discrete differencing of the acquired spectra was performed. Additionally, derivative application after smoothing of the acquired spectra (Savitzky-Golay, 9 point window) was used.

Two sets of numerical simulations were used using the measured data from the human subject measurements. The first analysis hereafter was aimed at determining the effect of photobleaching in introducing spurious correlations in calibration models. To characterize this relationship, the robustness and prediction accuracy of calibration models developed on the photobleaching correlated and uncorrelated data sets was analyzed. In the fluorescence removal aspect, the same analysis was repeated with two fluorescence removal techniques in the analysis with: (a) least squares polynomial subtraction and (b) SSRS. This analysis was used to compare the improvement in prediction performance obtained in both cases, correlated and uncorrelated, employment of different fluorescence removal strategies.

Simulation calibration spectra were first generated by forming weighted linear combinations of constituent analyte spectra of glucose, creatinine and urea as measured by the Raman system. For the present embodiment of the invention, glucose is the analyte of interest, with the other two constituents playing the role of spectral interferents in the mixture model. The assigned weights in the linear combinations correspond to the concentrations of the analytes in the sample at that particular time instance. Two sets of simulation spectra were constructed: (a) a correlated spectral dataset and (b) an uncorrelated spectral dataset. Specifically, the correlation coefficient $\rho_{A,B}$ between two random variables A and B is given by:

$$\rho_{A,B} = \frac{\text{cov}(A, B)}{\sigma_A \sigma_B} \qquad (5)$$

where cov(A,B) gives the covariance between A and B and $\sigma_A$ and $\sigma_B$ are the standard deviations of A and B, respectively. For the considered case, the variables A and B are constituted by the fluorescence intensity values and glucose concentrations, respectively. In the following, the strength of correlation is the $R^2$ value, which is the square of $\rho_{A,B}$.

To generate the correlated spectral dataset, the concentrations shown in profile II (FIG. 14B) were assigned to glucose to formulate the mixture Raman spectra. The glucose concentration values of profile II show a strong negative correlation with the photobleached fluorescence levels plotted in FIG. 13B ($\rho_{A,B} \approx -0.95$, $R^2 \approx 0.9$). For the uncorrelated dataset, the concentration values from profile I (FIG. 14A) were allocated for glucose, as the correlation between this profile and the aforementioned photobleaching curve is insignificant ($R^2 \approx 0.1$). Noted that the concentrations of creatinine and urea in both sets of simulation spectra were kept nearly constant (i.e. within 5% variation) to replicate the negligible changes observed in the concentration levels of the other analytes during a typical OGTT.

To represent the fluorescence, hyper-smoothing of a typical tissue spectrum to remove the sharper Raman features and retain only the autofluorescence background. For both correlated and uncorrelated dataset simulations, this hyper-smoothed spectrum was scaled by a factor specified by the photobleaching profile (FIG. 13B at that particular time before addition to the mixture Raman spectra. Moreover, in order to fully evaluate the impact of fluorescence to Raman amplitude ratio on the performance of the calibration models for both the correlated and uncorrelated cases, the relative intensity of the fluorescence and Raman signals was also varied in the range of 5-20. Finally, noise was generated in accordance with the shot-noise-limited condition for addition to the fluorescence-Raman combination spectra. The signal-to-noise ratio (SNR), defined here as the ratio of the maximum intensity of the fluorescence-Raman combination signal to the mean noise magnitude, was varied from 50 to 200. The range of fluorescence to Raman amplitudes and SNR values mentioned above are consistent with that observed in Raman spectra acquired for these types of analytical measurements (typical values of observed SNR-100 and fluorescence-to-Raman ratio-10). At each setting of the tunable parameters, i.e. fluorescence to Raman ratio and SNR, 100 calibration spectra were generated for the correlated as well as the uncorrelated datasets.

The prediction spectra were generated following a method similar to that stated above except that the concentrations of all the analytes were completely randomized in this dataset. The fluorescence levels in the prediction spectra were also completely randomized to simulate those observed in a set of unknown samples where the fluorescence levels and the concentrations of the analytes would be expected to possess minimal correlation with one another. This situation typically occurs when a calibration method developed during a tolerance or loading test is used prospectively on different subjects to determine their glucose levels. For a given setting of the fluorescence to Raman ratio and SNR level, 50 such spectra were included in the prediction data set.

Partial least squares (PLS) analysis was used to develop the calibration models based on leave-one-out cross-validation on the calibration (training) set. The final errors (root-mean-square error of prediction (RMSEP), Eq. (2)) were obtained by employing these calibration models on the independent prediction sets.

$$RMSEP = \sqrt{\sum_{i=1}^{n_p} \frac{(C_{act} - C_{pred})^2}{n_p}} \quad (6)$$

where $C_{act}$ and $C_{pred}$ are the actual and predicted glucose concentrations in the prediction sample and $n_p$ is the number of samples used in the prediction set (25). To ensure reproducibility of these results, the entire calibration-prediction procedure was repeated 20 times.

In this example a similar algorithm as that outlined above was used except that all the spectra (i.e. calibration and prediction, both for correlated and uncorrelated cases) were processed for fluorescence removal. Here, SSRS was employed to quantify its benefits, relative to that of numerical post-processing schemes, for both the photobleaching correlated and uncorrelated cases.

For this analysis a second set of calibration and prediction spectra for both the correlated and uncorrelated datasets was generated by shifting the composite mixture spectra (Raman plus fluorescence) by 25 cm$^{-1}$. These shifted spectra were then subtracted from the original set of spectra to obtain the Raman difference spectra (plus shot noise and residual fluorescence background). This analysis employed the difference spectra directly in analysis to extract concentration information through PLS. The direct incorporation of the difference spectra into calibration analysis is advantageous as it avoids the artificial spectral features and noise (ringing behavior) that may appear due to the application of a reconstruction method (such as Fourier deconvolution).

For fair comparison with numerical strategies, implement three variations of least-squares polynomial subtraction as alternative fluorescence removal tools. First, a lower order polynomial is fit to the broad fluorescence background and subtracted. Specifically, a second or third order polynomial for the PLS analysis is used depending on which order provides the least error in cross-validation. This approach can be pursued for signals with broad fluorescence backgrounds because higher order polynomials tend to overfit the data. Second, an algorithm developed by Mahadevan-Jansen, Appl. Spectrosc. 51(2), 201-208 1997, incorporated herein by reference, which automatically fits a modified polynomial just below the original spectrum, can be used. Third, an adaptive 'minmax' scheme is used to subtract the background fluorescence. PLS analysis is undertaken in conjunction with each of the three numerical processing schemes.

PLS was first used in a leave-one-out cross validation routine on the calibration spectral set. The number of loading factors used to build the final model for prediction was in accordance with the number of constituents that provided the minimum error in cross-validation. The results of the simulations at varying levels of Raman-to-noise ratio for the photobleaching correlated and uncorrelated cases are plotted in FIG. 15 with error bars indicating the standard deviation of the RMSEP values at each setting. It is evident that the calibration model developed on the correlated calibration spectra always performs worse than the model developed on the uncorrelated set, irrespective of the SNR value or the fluorescence-to-Raman amplitude ratio. For example, at a setting of fluorescence-to-Raman of 10 and SNR of 100 (values observed typically for tissue Raman spectra), the mean prediction errors were measured to be 16.3 mM and 5.3 mM for the correlated and uncorrelated cases, respectively, thereby demonstrating an approximately three-fold increase in the prediction error. Expectedly, for lower levels of Raman-to-noise ratio the prediction performance of both methods drop considerably. (It is noted that changing the fluorescence-to-Raman ratio or the SNR has an identical effect, as they both modulate the Raman-to-noise ratio.) Importantly, the performance of the calibration method built on the correlated dataset drops off much more significantly than that developed on the uncorrelated dataset as evidenced by the widening gap between the bars at higher fluorescence-to-Raman (i.e. lower Raman-to-noise) settings. This can be attributed to the fact that it becomes more difficult to distinguish the Raman spectrum of glucose from the confounding fluorescence background in a noisier spectral set. The simplest solution to reducing the disparity between the correlated and uncorrelated datasets is to increase the overall SNR, which can then decrease the RMSEP. However this can come at the cost of either increased exposure time or increased laser power.

The comparison of PLS prediction performance between correlated and uncorrelated datasets (FIG. 15) can be further generalized to show that the amount of deterioration in the prediction performance is dependent on the magnitude of correlation ($R^2$) between glucose concentration and tissue fluorescence. In FIG. 16, RMSEP increases with increasing $R^2$ for all values of fluorescence-to-Raman ratios. At low values of $R^2$, the RMSEP appears to be independent of $R^2$, but displays a steep rise after a threshold value of $R^2$. This suggests that the prediction error at low values of $R^2$ is determined primarily by the spectroscopic SNR, while at higher values of $R^2$, the prediction error depends on both SNR and $R^2$. This can also be visualized by observing the widening gap between any pair of RMSEP curves with an increase in $R^2$ in FIG. 16.

Figure 15:
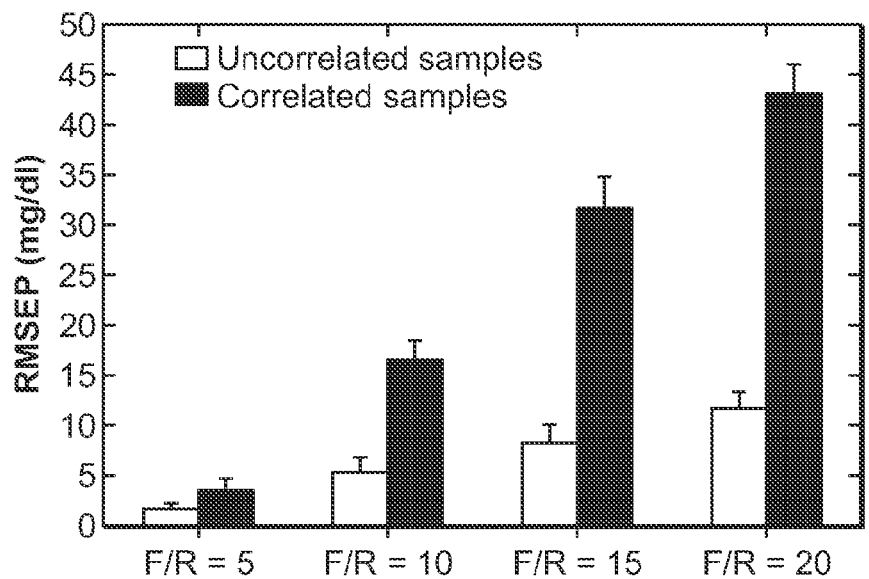
FIG. 15 illustrates a bar plot of RMSEP obtained for calibration models developed on photobleaching correlated (right bar) and uncorrelated (left bar) datasets, respectively, as a function of increasing fluorescence-to-Raman ratio (i.e. decreasing Raman-to-noise ratio), where the SNR is held constant); note that identical results are obtained by changing the SNR while holding the fluorescence-to-Raman ratio fixed.
Figure 16:
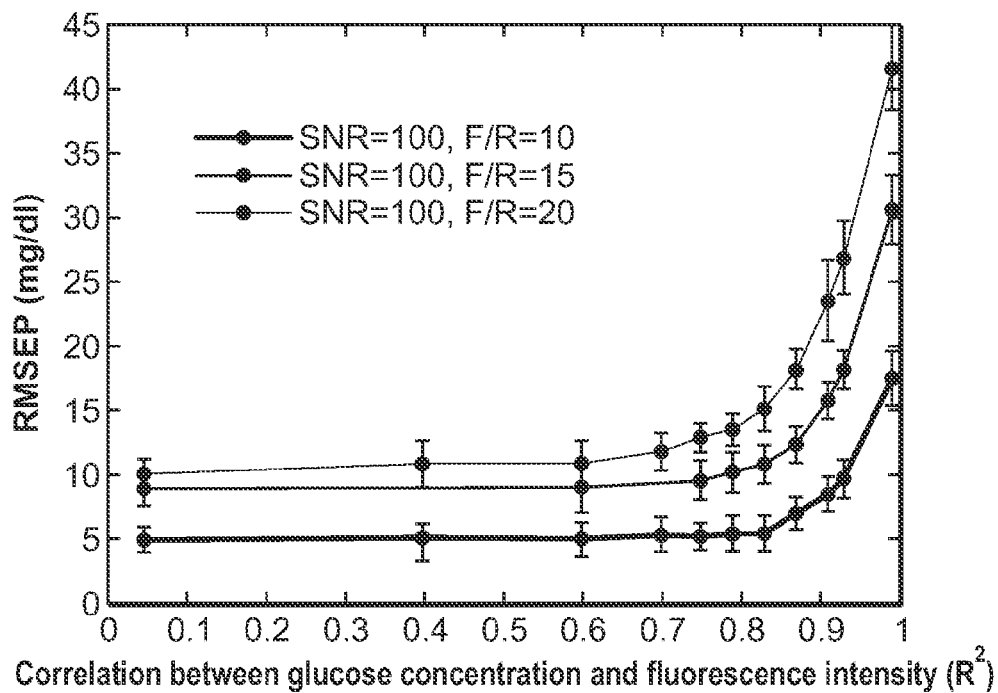
FIG. 16 illustrates RMSEP of simulations as a function of the correlation ($R^2$) between glucose concentration and fluorescence intensity; the fluorescence-to-Raman ratio (F/R) was varied from 10, 15 to 20, and 20 simulations were performed for each case.

The results of FIG. 15-16 also have extensive clinical implications, particularly for the correlated case. Such a situation is representative of measurements from OGTTs performed on diabetic and insulin-resistant patients. Since it is difficult to perform glucose/insulin clamping studies in normal and, particularly, diabetic populations, tolerance tests have remained the most viable protocol for the development of a calibration model using spectroscopic techniques. Moreover, while test strip based measurements and glycosylated hemoglobin (HbA1c) examination are more extensively used at the present time, tolerance tests remain the gold standard of clinical tests of insulin/glucose control system and have been used on a regular basis to screen for gestational diabetes and to determine the level of insulin resistance. However, these results indicate that photobleaching introduces a systematic error in Raman spectroscopic calibration model development using tolerance tests, particularly for people with impaired glucose regulation. Put another way, methods developed on a diabetic population is susceptible to substantial errors in prospective prediction, even when used for diabetic patients only. The remedies to break the unwanted correlation include a change in measurement (e.g. point-of-care measurements across a large population) and removal of the fluorescence background. The inclusion of a large number of human patients in the calibration set may, however, introduce additional complexities such as large variations in tissue optical properties and skin heterogeneity.

Figure 17:
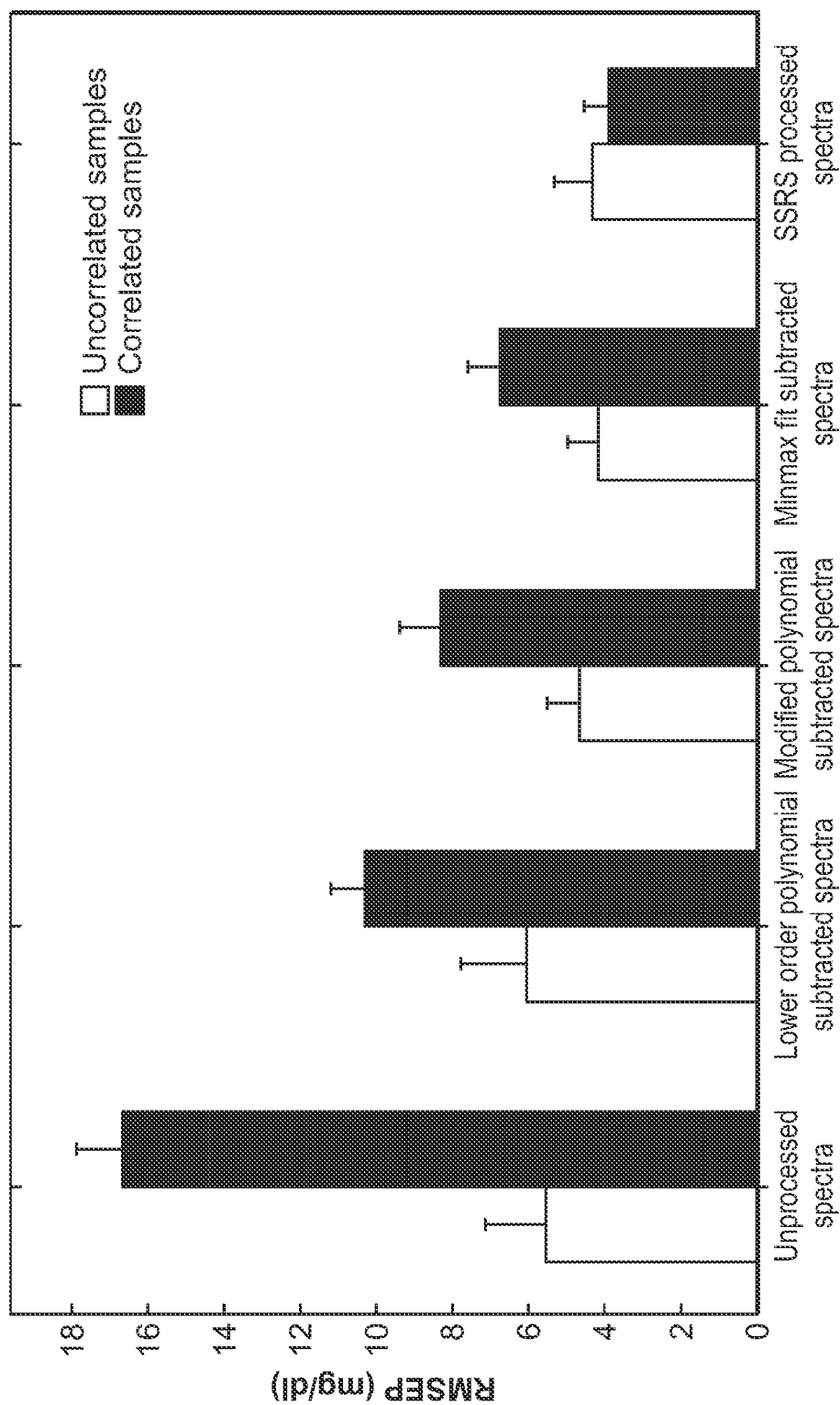
FIG. 17 illustrates a bar plot of RMSEP values obtained for glucose concentrations from simulations on photobleaching correlated (right bar) and uncorrelated (left bar) datasets. The groups represent calibration and prediction performed using the following types of spectra (from left to right) unprocessed, lower order polynomial subtracted, modified polynomial subtracted, minmax fit subtracted and SSRS processed spectra, respectively.

In the present embodiment, the fluorescence removed spectra, SSRS-processed and least squares polynomial subtracted, were used in conjunction with the concentration datasets to build the calibration models. The results of prospective prediction of the five models (i.e. based on raw, lower order polynomial subtracted, modified polynomial subtracted, minmax fit subtracted and SSRS processed spectra) are summarized in FIG. 17. For this set of simulations, experimentally observed values of SNR (of 100) and fluorescence-to-Raman ratio (of 10) were used.

For the correlated case, SSRS provides substantial reduction of prediction error (from 16.7 to 3.8 mg/dl), even lower than the levels obtained using the raw uncorrelated calibration model (5.5 mg/dl). Conventional lower-order polynomial subtraction, on the other hand, provides only about half the amount of improvement (from 16.7 to 10.3 mg/dl) as SSRS processing for the correlated case. This disparity in results could be attributed primarily to the introduction of non-physical negative regions in the spectra and associated artifacts due to the process of fluorescence removal using the polynomial subtraction technique. Newer variants of the polynomial subtraction technique, namely the modified polynomial (8.3 mg/dl) and adaptive minmax fitting (6.7 mg/dl), provide lower average RMSEP values than conventional polynomial subtraction. Thus, the inclusion of meaningful constraints in these techniques enhances the prospective prediction accuracy, though not to the levels obtained using SSRS.

Thus results for the uncorrelated case indicate that application of SSRS or numerical processing do not cause similar changes in prediction performance from the raw spectra results. This occurs because implicit calibration schemes (PLS) can be used for separating the analyte of interest (e.g. glucose) from the confounding analytes (including tissue fluorescence), especially when acceptable levels of SNR are achieved.

Finally, it is important to understand that these numerical simulations have been based on the assumption that the main factor limiting SNR is the shot noise in the system. Although this assumption holds for measurements on tissue samples where exposure times are limited by other constraints, this may not always be the case. There are many situations where it is observed that the random but fixed variations in pixel-to-pixel response on the CCD used in spectrograph systems, for example, might actually be more dominant than shot noise. This is especially true when high signal levels can be achieved and exposure times can be increased without any significant downside (such as when chemical mixtures and powder samples are measured). SSRS can provide an improvement in such applications because the major cause of noise arising from the irregularity in detector response can be canceled when the shifted spectra are subtracted.

Figure 18A:
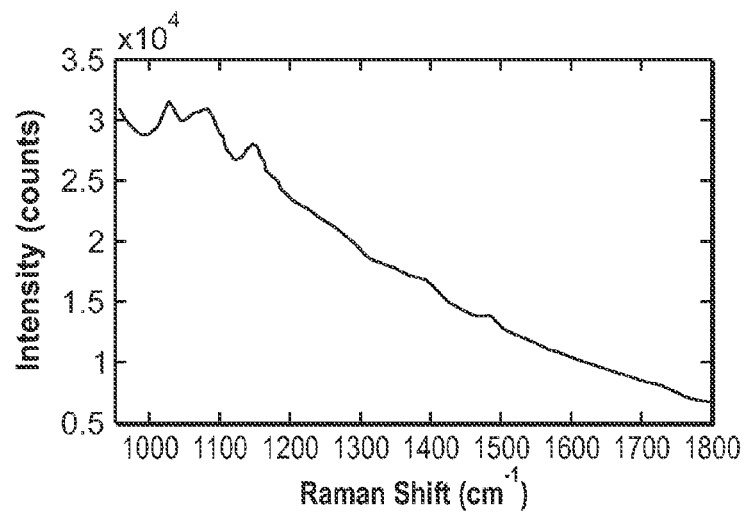
FIGS. 18A-18C are representative Raman spectrum acquired from a tissue phantom; and SSRS spectrum obtained by subtracting two spectra, obtained at spectrograph grating positions 25 $cm^{-1}$ apart; and the first derivative spectrum, respectively.
Figure 18B:
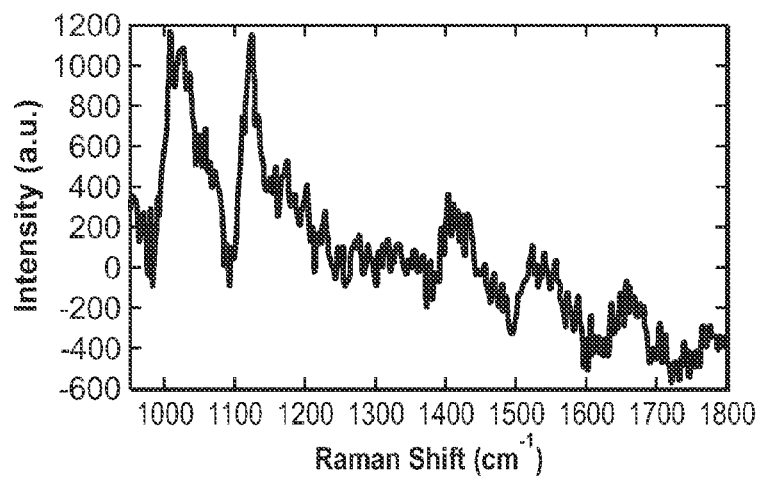
Figure 18C:
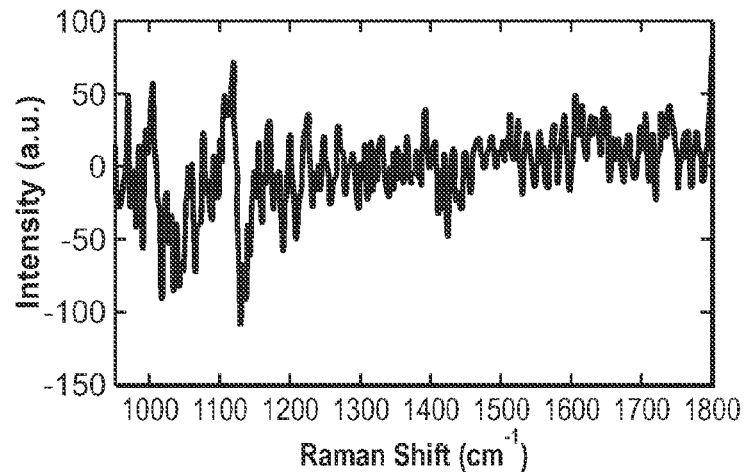

To validate the simulation results, the spectral datasets obtained in the tissue phantom measurements were analyzed. FIG. 18A-18C show: (A) a raw Raman spectrum obtained from a representative tissue phantom, (B) SSRS data obtained by subtracting two raw spectra, obtained at slightly different spectrograph grating positions, 25 cm$^{-1}$ apart and (C) numerical first derivative of the raw spectrum shown in FIG. 18A. It is clear that the fluorescence background can be suppressed using either shifted subtraction at two grating positions (SSRS) or taking the first derivative.

However, the SNR of the SSRS data appears to be significantly better than that of the first derivative spectra. This can be attributed to the cancellation of the fixed pattern noise on the CCD detector, as discussed above. It should be noted that having the correct amount of shift between the two acquired spectra is important to the application of SSRS as too small a shift can result in poor SNR and too large a shift can cause improper background suppression. For the SSRS spectrum, the presence of a small residual background is observed because of the corresponding shift in fluorescence in the two sets of spectra.

A prediction dataset can be formed by randomly extracting 10 uncorrelated tissue phantom data. PLS calibration models can then constructed based on the raw spectra, SSRS spectra and first derivative spectra for both the fluorescence-correlated and uncorrelated datasets (which consisted of 20 tissue phantoms each). Model performance during optimization was judged by comparing the standard error for leave-one-out cross-validation in the calibration data set. The prediction set was withheld from all optimizations and was solely employed to evaluate the performance of the final optimized models. The whole procedure was iterated fifty times to obtain an average and standard deviation of the RMSEP values. Table 4 summarizes the results of prospective prediction.

TABLE 4

|  | Raw | SSRS | $1^{st}$ derivative | $1^{st}$ derivative after smoothing |
| --- | --- | --- | --- | --- |
| Correlated | 53.8 (±7.8) mM | 42.7 (±7.3) mM | 66.3 (±9.2) mM | 56.0 (±8.1) mM |
| Uncorrelated | 39.1 (±6.7) mM | 42.4 (±6.2) mM | 65.0 (±8.1) mM | 55.5 (±8.9) mM |

The prediction performance of the calibration model built on the fluorescence correlated dataset is substantially worse than that built on the uncorrelated phantoms. The mean prospective prediction errors are 53.8 mM and 39.1 mM for the correlated and uncorrelated calibration models, respectively. Importantly, the application of SSRS reduces the error in the correlated calibration model from 53.8 mM to 42.7 mM to the levels achieved with the uncorrelated dataset. The application of SSRS marginally increases the prediction error of the uncorrelated dataset from 39.1 mM to 42.4 mM. This may be attributed to the imperfect rejection of the fluorescence background by SSRS application. Nevertheless, the two primary results observed previous numerical simulations are reinforced by this tissue phantom analysis: (a) calibrations developed from the fluorescence-correlated datasets have a greater prediction error than calibrations developed with fluorescence-uncorrelated datasets and (b) the application of frequency shifted spectra provides more accurate concentration predictions than that obtained from the unprocessed spectra, particularly for the fluorescence-correlated dataset.

In sharp contrast to SSRS, the first derivative application appears to adversely impact the prediction performance for both the fluorescence correlated and uncorrelated datasets. One would expect that this is an outcome of the reduction in SNR of the first derivative spectra shown in FIG. 18C. This is consistent with previous observations, especially when an additional filtering procedure is not employed. It has also been previously reported that the derivative method makes the lower intensity Raman bands difficult to identify in the processed spectrum. Smoothing of the acquired spectra before the differentiation procedure, however, reduces the average RMSEP value, probably due to the resultant increase in SNR, compared to simple derivative application.

Taken in conjunction with the least squares polynomial subtraction results, this indicates that while the numerical fluorescence removal strategies are able to suppress the fluorescence background, the instrumentation-based SSRS technique can provide better quantitative predictions for systems employing a grating.

A central challenge in the development of a robust calibration model for transcutaneous blood analyte detection using Raman spectroscopy lies in overcoming the effects of photobleaching-induced non-analyte specific variations. This analysis indicates that a deterioration in model performance can be observed due to the photobleaching induced spurious correlations. At typically observed levels of SNR and fluorescence to Raman ratio, this may result in a factor of three increase in prediction error. This has implications in developing a calibration model, particularly for diabetic patients using glucose tolerance test-like protocols. To remedy the situation, it is preferable to incorporate a change of the fluorescence removal strategy.

Furthermore, SSRS reduces the prospective prediction error of the developed calibration models by rendering the model less susceptible to spurious effects associated with photobleaching correlated samples. In this regard, SSRS appears to substantially outperform conventional numerical post-processing schemes such as least squares polynomial subtraction and derivative application. Note that newer numerical processing methods, such as the adaptive minmax approach and the automated background removal algorithm can be used to provide better results than the conventional numerical methods. The above analysis indicates that for systems employing a grating, the problem of photobleaching-induced spurious correlation can be better solved by incorporating a tunable spectrograph, as compared to numerical processing schemes. Such implementation ensures that the principal advantages of glucose tolerance tests (i.e. the convenience of testing and the lack of stringent glucose and insulin control requirements as are necessary for clamping studies) are not sacrificed. For preferred embodiments of the present invention in which a grating is not used a SERDS approach is preferred as this has the advantage of reducing the noise in the detected signal and does not require the measurement of a broad spectrum but can be used with either a tunable laser source as described herein or with two lasers operating at different wavelengths that are switched using beamshutters and are routed onto a single optical path using a beamsplitter.

Another factor in the accurate measurement of blood glucose is to adjust for the physiologic lag that can occur between blood glucose and interstitial fluid (ISF) glucose. The optical measurement of blood glucose can be based in many situations on ISF glucose measurements due to the fact that in near infrared wavelengths frequently used penetrate the first 1.0-1.5 mm of tissue where the small density of blood vessels in the skin can limit the effectiveness of the measurement.

Non-invasive glucose diagnosis has received considerable attention due to its important implications for diabetes management and therapeutics. Various techniques ranging from electrochemical assays to optical methods have been proposed to meet the goals of painless and accurate glucose measurements. Vibrational spectroscopy, notably near infrared (NIR) absorption and Raman spectroscopy, has shown substantial promise in this regard. Specifically, NIR Raman spectroscopy has provided successful predictions of glucose at physiologically relevant concentrations in serum, whole blood, and even in human volunteers. However, a clinically accurate and robust algorithm for predicting glucose concentrations in multiple human subjects, or even in the same subject at different times, is currently lacking.

Researchers have identified factors that degrade the glucose measurement accuracy of Raman spectroscopy by introducing non-analyte specific variance into the calibration model. The predominant factors include sample-to-sample variability in absorption and scattering properties (turbidity), tissue autofluorescence and associated quenching, and physiological lag between blood and interstitial fluid (ISF) glucose. Several spectroscopic correction schemes have been implemented to minimize the effect of the first two factors, but correction for the presence of a lag time has not been demonstrated for transcutaneous glucose monitoring, due to its intricate relationship with the fundamental physiological dynamics. This lag time creates an inconsistency in spectroscopic calibration algorithms, which are based on reference blood glucose concentrations and the acquired tissue spectra. This inconsistency arises from the fact that the spectroscopic techniques primarily probe ISF glucose, due to the relatively shallow penetration depth (~1 mm) of NIR light in tissue and the small density of blood vessels in the superficial layers of the skin.

This inconsistency in calibration presents a severe hindrance not only for spectroscopy based non-invasive glucose monitoring but also for minimally invasive electrochemical sensors (such as Medtronic/Minimed's Guardian and Free-Style Navigator from Abbott Diabetes Care), which base their glucose estimates on interstitial fluid measurements. Indeed, as pointed out by Cengiz and Tamborlane, (Diabetes Technal. Ther. 2009, 11, 5-11-16) the physiological lag introduces systematic errors during calibration which adversely impact long-term sensor performance, even in the presence of a positive correlation between blood and ISF glucose. Such diagnostic errors may lead to unnecessary insulin bolus, which significantly increases the risk of hypoglycemia. The presence of systematic errors is one of the main reasons that such continuous glucose monitoring sensors need to be re-calibrated against fingerstick measurements at regular intervals.

Typically, for all ISF glucose-based sensors, spectroscopic or otherwise, the underlying assumption is that the blood-to-ISF glucose gradient remains constant over the measurement range. However, this assumption fails if the sensor is calibrated during rapid changes in blood glucose, as are encountered during glucose tolerance tests, which provide the most viable protocol for the development of calibration models using spectroscopic techniques. Calibration during such non-equilibrium conditions leads to large errors in the developed model. To account for the differences in blood and ISF glucose, a method for ISF glucose measurement can be done by considering the ISF and blood glucose to reside in two "compartments", and performing a mass balance between them. Using this method, glucose concentration can be extracted from subcutaneous ISF glucose-based measurements. This involves spectroscopic calibration methods, which are relatively complex in contrast to prior methods because of the multivariate nature of the data.

Furthermore, even if an accurate calibration model can be established by performing all measurements under equilibrium conditions (e.g. by employing glucose clamps), the lack of knowledge of glucose kinetics in prediction samples can introduce an uncertainty in the concentration estimates. Such prediction uncertainties may lead to inappropriate treatments.

The present invention utilizes spectroscopic calibration based on "dynamic concentration correction" (DCC), which is based on a two-compartment mass transfer representation of blood and ISF glucose and is designed to provide an accurate estimate of glucose concentrations for non-invasive measurements. These transformations are performed iteratively in conjunction with an implicit calibration method, such as partial least squares (PLS), to form an accurate and consistent regression model. The resulting calibration method can be used on a new set of acquired spectral samples, referred to as the prediction set, to calculate the ISF glucose concentrations of the samples. Subsequent application of the DCC method converts the estimated ISF glucose concentrations to the equivalent blood glucose concentrations of the prediction samples.

This embodiment employs Raman spectroscopy as a specific example to demonstrate the effectiveness of the new calibration method, with the understanding that this method can be similarly applied to other spectroscopic techniques, such as NIR absorption measurements. Using blood and ISF glucose concentration datasets, first demonstrate that predicted glucose concentrations using the DCC calibration method closely match the measured blood glucose concentrations, whereas those generated solely by the conventional implicit calibration methods show significantly larger deviations from the measured values. These results are further validated on spectral and concentration datasets obtained from clinical studies on human subjects undergoing glucose tolerance tests.

In addition, analytical expressions for the limiting uncertainty introduced in the concentration predictions due to presence of the physiological lag, with and without application of DCC. Here, limiting uncertainty is defined as the uncertainty in concentration estimate in the case where all modeling noise is disregarded, i.e. where the calibration model is assumed to be completely accurate and noise free. Employing the human data, the concentration uncertainty due to the lag phenomenon is comparable to that arising from the noise and overlap in the prediction spectra and that this major source of uncertainty can be significantly reduced (approximately six-fold) when DCC is used, providing further motivation for its use in spectroscopy-based transcutaneous blood glucose monitoring.

The primary motivation for proposing a spectroscopic calibration method for blood glucose detection is to establish consistency in the calibration model, which maps the spectral measurements to the glucose concentrations. The conventional linear calibration equation can be written as:

$$b = S^* c, \quad (7)$$

where b is the spectrum of regression coefficients (also called the regression vector), S is the matrix of calibration spectra and c is the vector of measured concentrations of the analyte of interest in the calibration samples. S* is the appropriate inverse of S, as evaluated by the calibration method of choice. (Lowercase boldface represents a vector and uppercase boldface denotes a matrix.)

Since the spectral measurements are predominantly contributed by ISF glucose, the relevant input concentrations to the implicit calibration method incorporate the ISF glucose concentrations. However, the ISF glucose concentrations are typically not available in a real-life clinical setting—instead, blood glucose values obtained from frequent blood withdrawals are used as reference concentrations. This creates a regression vector, which is neither based completely on blood glucose nor on ISF glucose, but a mixture of the two contributions. This, in turn, also creates a problem in the prediction step, where the predicted glucose concentration c is obtained by a scalar product of the regression vector b and the spectrum acquired from the prediction sample s:

$$c = s^T \cdot b. \quad (8)$$

(Lowercase italics indicates a scalar quantity and the superscript T denotes the transpose of the vector.) In the conventional calibration framework, the predicted glucose concentration is reported as the blood glucose concentration, although this clearly is not an accurate representation.

To correct for this issue a calibration methodology (DCC) in which the concentrations are appropriately changed to conform to the spectral measurements. The transformation in the concentration domain is based on a two-compartment mass transfer model, which establishes a well-defined relationship between blood glucose, ISF glucose and the system parameters. Specifically, the following two transformations are performed in DCC:

(a) Pre-calibration DCC (PC-DCC): Transform the blood glucose concentrations in the calibration dataset to their corresponding ISF values before inputting into the implicit calibration method. This ensures that the regression vector is solely based on ISF glucose contributions.

(b) Post-prediction DCC (PP-DCC): Re-transform the predicted ISF glucose concentration, which is determined by Eq. (2), to the corresponding blood glucose value.

Figure 19B:
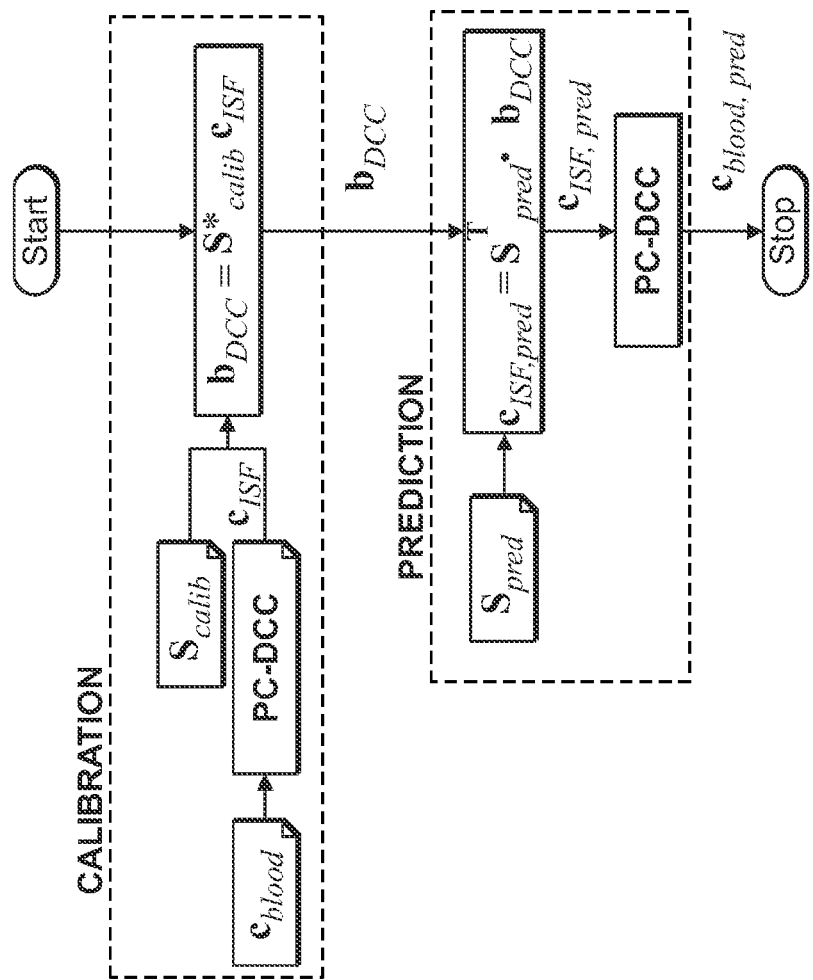
FIGS. 19A and 19B illustrate calibration process flow diagrams in accordance with the invention.
Figure 19A:
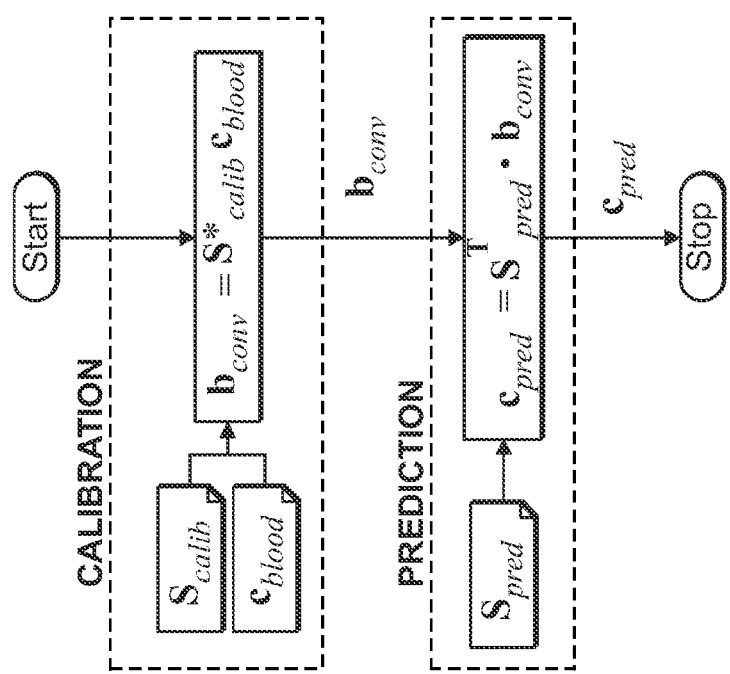

The conceptual differences between the conventional and proposed (DCC-based) calibration methods can be seen in FIG. 19A-19B.

For the subsequent analysis, assume that the sampling volume (i.e. the volume of tissue probed by the NIR light) is a subset of the interstitial fluid space. This assumption is primarily based on the fact that the ISF constitutes nearly 45% of the volume fraction of the human skin in contrast to the blood vessels which contribute about 5% of the skin volume.

Transfer of glucose from the blood to the ISF compartment occurs by passive diffusion across an established concentration gradient. The mass transfer rate is affected by several variables, such as the blood flow rate to the site, rate of glucose uptake by the surrounding tissue, and the capillary permeability. Nevertheless, a simple two-compartment mass-transfer model can be written for the ISF volume $V_{ISF}$:

$$V_{ISF} \frac{dc_{ISF}}{dt} = k_M A(c_{BG} - c_{ISF}) - k_U V_{ISF} c_{ISF}, \quad (9)$$

where $c_{ISF}$ and $c_{BG}$ are the ISF and blood glucose concentrations (mol/cm$^3$) respectively, $k_M$ is the glucose mass transfer coefficient (cm/s), A is the effective mass transfer surface area (cm$^2$) and $k_U$ is the rate of glucose uptake by the neighboring cells (1/s). The effect of insulin on the uptake term has been ignored. This approximation is consistent with the observed result that the glucose levels in (subcutaneous) ISF are largely unaffected by the local insulin concentration.[34] In fact, the uptake term itself has been observed to be very small for subcutaneous glucose sensing. This is attributed to the fact that skin tissue, as opposed to muscle or adipose tissue, is unlikely to have significant glucose uptake, even in the presence of high insulin concentration. Consequently, dropping the uptake term in further analysis. Eq. (3) can then be simplified to:

$$c_{BG} = c_{ISF} + \alpha \frac{dc_{ISF}}{dt}, \quad (10)$$

where $$\alpha \left( = \frac{V_{ISF}}{k_M A} \right)$$

is a lumped mass-transfer parameter having units of time. The parameter α provides a measure of the physiological lag time arising from the diffusion process and is henceforth called the characteristic lag time constant. This equation provides the ability to construct blood glucose estimates based on the spectroscopy-based ISF glucose prediction values and a priori knowledge of the lag time constant in the sample. The numerical evaluation of this equation, which provides the post-prediction (PP-DCC) step.

The other important portion of the proposed scheme is the pre-calibration (PC-DCC) step. In order to obtain consistency in the calibration model, convert the measured blood glucose concentrations to the corresponding ISF glucose values. To perform this transformation, using Eq. (10) in its integral form:

$$c_{ISF}(t_f) = c_{ISF}(t_i) \exp\left(-\frac{1}{\alpha}(t_f - t_i)\right) + \frac{1}{\alpha} \int_{t_i}^{t_f} c_{BG} \exp\left(-\frac{1}{\alpha}(t_f - t_i)\right) dt, \quad (11)$$

where the definite integral is evaluated from time $t_i$ to $t_f$. Details of the numerical implementation of this equation are given.

After employing integration by parts for the second term of Eq. (11), numerical integration was performed by using Simpson's rule to get the following equation:

$$c_{ISF}(t_f) = c_{BG}(t_f) + (c_{ISF}(t_i) - c_{BG}(t_i)) \exp\left(-\frac{t_f - t_i}{\alpha}\right) - \frac{t_f - t_i}{6} A \quad (12)$$

where $$A = \dot{c}_{BG}(t_i) \exp\left(-\frac{t_f - t_i}{\alpha}\right) + 4\dot{c}_{BG}\left(\frac{t_i + t_f}{2}\right) \exp\left(-\frac{t_f - t_i}{2\alpha}\right) + \dot{c}_{BG}(t_f) \quad (13)$$

Here, $c_{BG}\dot{}(t)$ refers to the derivative of $c_{BG}$ evaluated at t. This equation can be readily evaluated by approximating $c_{BG}\dot{}(t)$ via a first-order finite difference approximation similar to that employed in Eq. (14) for the PP-DCC step. A first-order accurate estimate of the blood glucose concentration can be obtained by using a finite difference approximation for the derivative term of Eq. (14):

$$c_{BG}(t) = c_{ISF}(t) + \alpha \frac{c_{ISF}(t) - c_{ISF}(t - \Delta t)}{\Delta t} \quad (14)$$

where Δt is the time interval at which spectroscopic measurements (and thus, ISF glucose concentration estimates) are obtained. The above equation gives the discrete transformation equation of the post-prediction (PP-DCC) step, which can be applied in real-time. There are a couple of points worth noting about the application of Eq. (14). Firstly, it is evident from the above equation that at least two spectroscopic predictions of ISF glucose (at t and t−Δt) are necessary in order to determine the blood glucose concentration at time t. In practice, it is beneficial to perform multiple spectroscopic acquisitions so that the corresponding blood glucose estimates can be averaged to ensure less fluctuations in the predicted blood glucose value. Secondly, the time interval Δt, at which the spectroscopy based ISF glucose predictions should be performed, needs to be ascertained. Although spectroscopic acquisitions can be performed rapidly, having a very small Δt is not too useful as it may fail to capture the changes in the glucose levels due to the slow diffusion kinetics—thereby rendering the DCC approach ineffective. On the other hand, too large a time interval would introduce substantial errors in the derivative term. Using these limiting cases as a guideline, optimize the value of Δt with a starting point given by a fraction of the typical physiological lag time (~5-10 min).

The resultant discretized version of Eqs. 12 and 13 give the transformation equation for the PC-DCC step. The primary challenge in the evaluation of these equations lies in having a priori knowledge of the initial ISF glucose value, i.e. at the start of the time window $[t_i, t_f]$. Generally, such information is not available for an arbitrary time window. However, during a spectroscopic calibration study such as glucose clamp or tolerance test, one can ensure that the ISF glucose and blood glucose values are completely in equilibrium at the start of the experiment by restricting the glucose intake of the subject prior to the measurements. For example, a typical oral glucose tolerance test (OGTT) protocol stipulates that the patient must fast for 8-14 hours before the study. This initial condition enables successful evaluation of Eqs. 12 and 13 for the first time window. For each subsequent evaluation, the ISF glucose value at time $t_f$ for the previous window is inputted as the initial value (at time $t_i$) for the current window. Evidently, the shorter the time window over which the evaluation is performed, the higher the accuracy of the determined ISF glucose concentrations. Nevertheless, the time window cannot be shortened below a lower bound, governed by the maximum permissible frequency of blood withdrawal from a human subject. Generally, for example, sample blood glucose at time intervals ranging from 2.5-10 minutes. To determine the values of the concentrations and their derivatives at intermediate points, spline interpolation can be employed.

In order to quantify the precision of spectroscopy based calibration models, Lorber and Kowalski derived a prediction error formula, which describes the error propagation for linear multivariate prediction algorithms. The analytical expressions for uncertainty in concentration prediction for the specific case where noise in the prediction dataset (spectra) is the dominant source of error. This case is important, as in most biomedical applications constraints on the acquisition time in prediction samples cause the noise in the prediction dataset to be significantly higher than that observed in the calibration dataset (where acquisition times are typically much longer). In such cases, it can be assumed that an accurate calibration model can be achieved by developing it on calibration samples in which sufficiently high signal-to-noise ratio (SNR) can be attained. Under such conditions, the limiting uncertainty in the predicted concentrations arises from the spectral overlap between the analyte of interest and the other tissue constituents, and the measurement noise in the spectra acquired from the prediction samples. Mathematically, the spectroscopic uncertainty for the analyte of interest (glucose) is given by $\Delta c_s$[33]:

$$\hat{c} = (s \pm \Delta s)^T \cdot b = s^T \cdot b \pm \Delta s^T \cdot b = c \pm \Delta c_s \quad (15)$$

where $$\Delta c_s = \frac{\sigma}{s_g} olf \quad (16)$$

Here, $\hat{c}$ and $c$ are the estimated and actual analyte concentrations in the prediction sample, respectively and $\Delta s$ represents the spectral noise in the prediction spectrum s. As the modeling noise is ignored in computation of the limiting uncertainty, b represents the ideal (noise-free) regression vector for glucose. $\sigma$ is a measure of the noise magnitude in the prediction spectrum, $s_g$ quantifies the signal strength of glucose at unit concentration, and olf indicates the amount of overlap between glucose and the other spectral interferents (such as proteins, lipids, and water).

In addition to the spectroscopic uncertainty, there exists a prediction uncertainty for transcutaneous glucose measurements that arises from the physiological lag between blood and ISF glucose levels. Even if the calibration models are developed under conditions in which the blood and ISF glucose concentrations are in equilibrium (such as those obtained by employing glucose/insulin clamps), the predicted concentrations will still contain uncertainties due to the unaccounted physiological lag in the prediction samples. The following error propagation analysis can be used to determine the limiting uncertainty in concentration prediction due to the physiological lag, with and without DCC. Assume that the developed calibration model itself is accurate, i.e. devoid of noise and lag-related errors.

When the modeling noise is ignored, Eqs. (15) and (16) provide the relationship between the estimated and the actual glucose concentrations. However, for in vivo prediction, there will be a lag between the instantaneous blood and ISF glucose values in the sample, where the latter is measured by the prediction spectrum. Taking this into account, re-writing Eqs. (15) and (16) in terms of the estimated ($\hat{c}_{ISF}$) and actual ($c_{ISF}$) ISF glucose concentrations:

$$\hat{c}_{ISF} = (s \pm \Delta s)^T \cdot b = c_{ISF} \pm \Delta c_s. \quad (17)$$

Based on the two-compartment model, the actual blood glucose concentration, $C_{BG}$, can be determined from the actual ISF glucose concentration using Eq. (10), given the correct lag time constant for the prediction sample ($\alpha_{actual}$). Substituting the value of the actual ISF glucose concentration from Eq. (17) into Eq. (10), obtain:

$$c_{BG} = c_{ISF} + \alpha_{actual} \frac{dc_{ISF}}{dt} = \hat{c}_{ISF} + \alpha_{actual} \frac{d\hat{c}_{ISF}}{dt} \pm \Delta c_s. \quad (18)$$

However, the conventional models report the estimated ISF glucose concentration as the blood glucose concentration ($\hat{c}_{BG}$) in the prediction sample:

$$\hat{c}_{BG} = \hat{c}_{ISF}. \quad (19)$$

Substituting Eq. (19) into Eq. (18) and re-arranging, obtain:

$$\hat{c}_{BG} = c_{BG} - \alpha_{actual} \frac{dc_{ISF}}{dt} \pm \Delta c_s \quad (20)$$

Equation (10) implies that under the conventional calibration framework, the limiting uncertainty in the concentration estimate has two separate contributions: (i) the uncertainty resulting from the measurement noise in the prediction spectrum and the spectral overlap, $\Delta c_s$ and (ii) the uncertainty due to the glucose physiological lag, $$\Delta c_{conv} = \alpha_{actual} \frac{dc_{ISF}}{dt}.$$

Figure 20A:
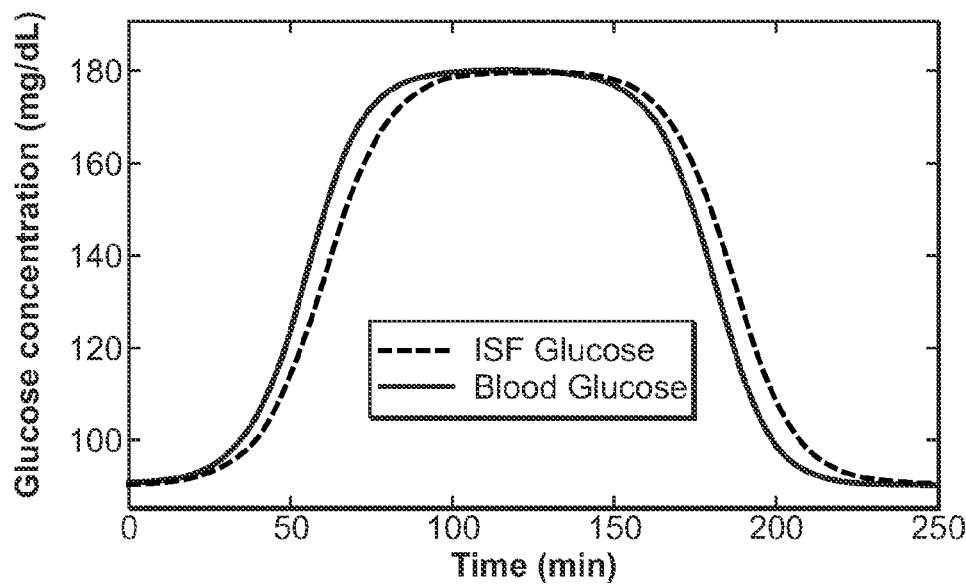
FIGS. 20A and 20B illustrate blood/ISF glucose concentration profile and ISF versus blood concentration profiles, respectively.
Figure 20B:
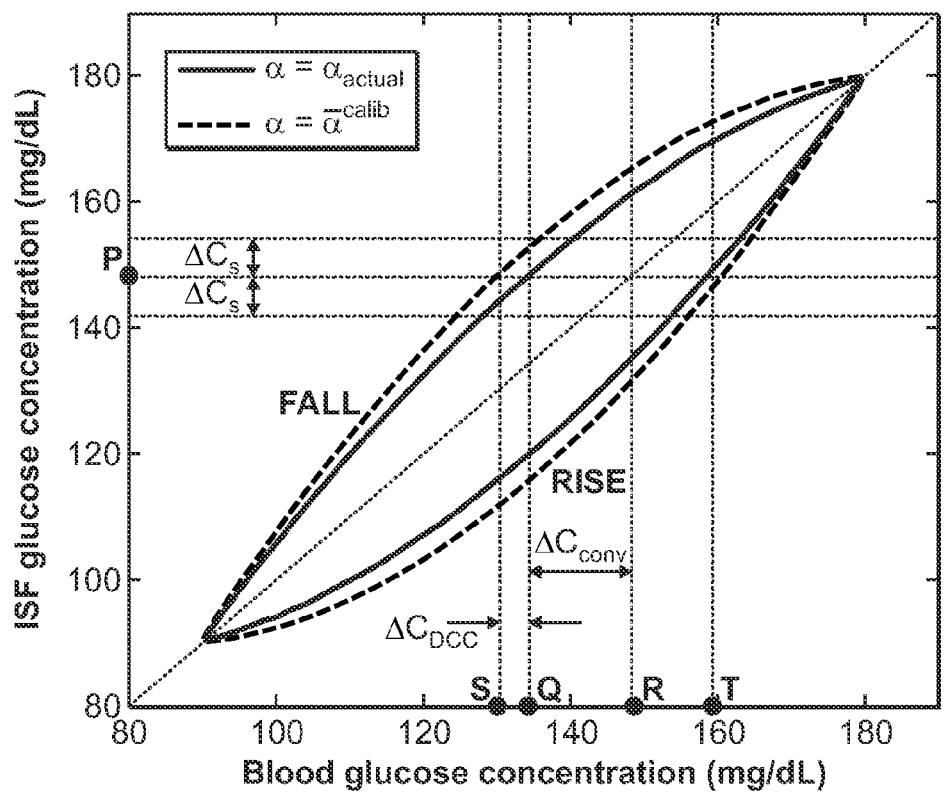

While the former (i) is a well-known quantity, the latter uncertainty (ii) has not been examined before. FIGS. 20A-20B illustrate the two contributing factors of the prediction uncertainty. The simulated blood and ISF glucose data in FIG. 20A (which mimics the glucose profiles obtained from a tolerance test) are plotted against each other to construct the solid line curve in FIG. 20B. It is evident that the physiological lag between the blood and ISF glucose profiles in FIG. 20A introduces a hysteresis-like closed loop behavior when blood glucose is plotted against ISF glucose, showing the lack of a one-to-one correspondence between the glucose concentrations in the two compartments. For example, given an ISF concentration of 148 mg/dl at point P, the actual blood glucose concentration could be either 132 mg/dl (Q) or 158 mg/dl (T). However, conventional methods that have the underlying assumption of a constant blood-to-ISF glucose gradient would predict 148 mg/dl (R), giving rise to a significant error in prediction. Specifically, when the glucose levels are increasing, the blood glucose concentrations are greater than the corresponding ISF glucose concentrations. This set of values is represented by the points on the concave upwards curve (labeled "RISE"). Similarly, the set of values obtained during the falling phase is represented by the concave downwards curve (labeled "FALL"). The lag uncertainty $\Delta c_{conv}$ in the predicted blood glucose concentration for the conventional calibration model is given by the distance between points Q and R. The uncertainty due to the noise and spectral overlap in the prediction spectrum is marked as $\Delta c_s$.

In contrast to the conventional model, the DCC method explicitly accounts for the physiological glucose dynamics. Specifically, the post-prediction equation (PP-DCC) is used to transform the spectroscopy-based ISF glucose estimate ($\hat{c}_{ISF}$) to a corresponding blood glucose value ($\hat{c}_{BG}$), and this step needs to be considered in evaluating the limiting uncertainty. As the correct lag time constant in the prediction sample is unknown in a real clinical setting, some uncertainty due to the physiological lag is introduced via the PP-DCC step. This employs the (ensemble) average of the lag time constants obtained from the calibration samples to approximate the actual lag time constant in the prediction sample. Based on this approximation, the PP-DCC equation can be re-written as:

$$\hat{c}_{BG} = \hat{c}_{ISF} + \overline{\alpha}^{calib} \frac{d\hat{c}_{ISF}}{dt}, \quad (21)$$

where $\overline{\alpha}^{calib}$ refers to the average value of $\alpha$ computed from the calibration samples.

Substituting Eq. (17), into Eq. (21):

$$\hat{c}_{BG} = c_{ISF} \pm \Delta c_s + \overline{\alpha}^{calib} \frac{dc_{ISF}}{dt}. \quad (22)$$

The deviation of $\overline{\alpha}^{calib}$ from the actual lag time constant in the prediction sample, $\alpha_{actual}$ can be written as:

$$\overline{\alpha}^{calib} = \alpha_{actual} \pm \Delta\alpha, \quad (23)$$

where $\Delta\alpha$ is the error (uncertainty) in the estimation of the lag time constant.

Substituting Eq. (23) into Eq. (22) and re-writing the first term of the above equation as $c_{BG}$:

$$\hat{c}_{BG} = c_{BG} \pm \Delta\alpha \frac{dc_{ISF}}{dt} \pm \Delta c_s \quad (24)$$

Equation (24), which is analogous to Eq. (20) for the conventional calibration model, implies that even with DCC, the net uncertainty is a combination of the uncertainties arising from the spectral noise and overlap ($\Delta c_s$) and the physiological lag $$\left(\Delta c_{DCC} = \Delta\alpha \frac{dc_{ISF}}{dt}\right).$$

However, the primary difference between the two cases—with and without DCC—lies in the magnitude of uncertainty introduced due to the physiological lag. The lag uncertainty for the conventional calibration model case (which is proportional to $\alpha_{actual}$) is significantly larger than that observed for DCC calibration (which is proportional to $\Delta\alpha$). This can be visualized in FIG. 20B. The dashed line curve of FIG. 20B connects the points whose co-ordinates are given by the model estimated blood and ISF glucose concentrations (in contrast to the solid line curve represents the points whose co-ordinates are given by the actual blood and ISF glucose concentrations). Since the exact lag time constant of the prediction sample is unknown, the estimated blood glucose concentrations will differ from the actual blood glucose concentrations by the product of the rate of change in glucose concentration and the estimation uncertainty of the lag time $$\left(\Delta c_{DCC} = \Delta\alpha \frac{dc_{ISF}}{dt}\right).$$

It is worth noting that the dashed (DCC estimated) curve is computed using Eq. (11), whereas the blood and ISF glucose concentrations of the solid curve are related by Eq. (10). From the above Figs., it is evident that $\Delta c_{DCC}$, the distance between points Q and S, is substantially smaller than $\Delta c_{conv}$, the distance between points Q and R, as long as the lag time constant used in the DCC model provides a reasonably close approximation to the actual lag time constant. A quantitative comparison of the two lag uncertainties and the spectroscopic uncertainty is described below.

Numerical simulations and measurements were used to: (1) demonstrate the improvement in prospective prediction performance of the calibration model on application of DCC and (2) estimate the distribution of the lag time constant in a human population and characterize the prediction uncertainty introduced due to the physiological lag. To accomplish (1), a numerical simulation study was undertaken. ISF and blood glucose concentration datasets were used to generate tissue Raman spectra for calibration and prediction. The simulations were also used to understand the relationship between the SNR in the spectral dataset and performance of the conventional and DCC calibration models. In order to investigate the lag time distribution in a human population, datasets obtained from clinical studies on human subjects were employed. Additionally, the human measurements were used to determine the limiting uncertainty arising from the physiological glucose dynamics.

Figure 21:
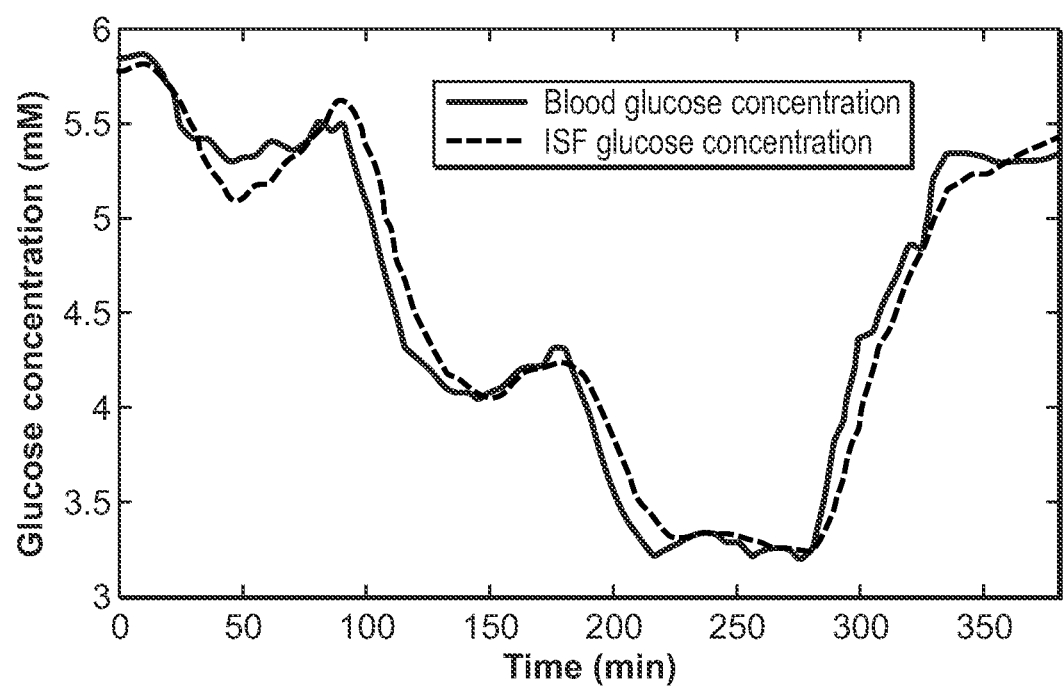
FIG. 21 illustrates an insulin induced measurement of blood and ISF glucose concentration.

The dataset used in numerical simulations were based on existing blood and ISF glucose concentrations. This work monitored blood and ISF glucose concentrations in non-diabetic human subjects during glucose clamping. After 10-12 hours of overnight fasting, glucose was sequentially clamped at approximately 5, 4.2 and 3.1 mM (1 mM of glucose≈18 mg/dL) for 90 minutes each by insulin and glucose infusion, and subsequently allowed to return to euglycemic levels. ISF glucose was measured by two MiniMed (Medtronic, Inc.) subcutaneous amperometric glucose sensors. Blood was withdrawn at regular intervals for blood glucose measurements using a clinical glucose analyzer. Analysis uses the blood and ISF glucose concentrations from 90 to 380 minutes after initial insulin and glucose infusion, as shown in FIG. 21. The simulated spectra and corresponding blood glucose concentrations is divided into calibration (dataset spanning from 90 to 220 min) and prediction (dataset from 230 to 380 min) sets, respectively.

In this embodiment, the simulated Raman spectra are generated by forming weighted linear combinations of the constituent Raman spectra of glucose, creatinine and urea. The weights assigned for glucose (the analyte of interest) are determined by the experimentally measured ISF glucose concentrations of the existing dataset. The other two constituents (spectral interferents) are assigned weights that randomly varied within 2% of a constant value, in order to mimic the small changes observed in these constituents during typical glucose tolerance and clamping tests. To simulate normal experimental conditions, zero-mean Gaussian white noise is added to the mixture spectra at varying levels of SNR (20-40 dB) to study its effect on prediction performance of the calibration models. The uniform noise across the spectra and the SNR range are consistent with typical Raman spectra of biological samples.

In contrast to the conventional PLS calibration strategy, where the number of loading vectors are optimized, in the DCC calibration the number of loading vectors as well as the lag time constant, $\alpha$, need to be optimized. To accomplish this, assign default values to $\alpha$ (0 minutes) and the number of loading vectors (2) employed, respectively. Prior to constructing the leave-one-out calibration model, all but one of the reference blood glucose concentrations are converted to the corresponding ISF glucose values using PC-DCC (Eq. (11)). This allows the creation of a calibration model based purely on ISF glucose. The developed calibration model, in conjunction with the spectrum of the excluded data point (which constitutes the validation data), is then used to predict the ISF glucose concentration at that point. Subsequently, PP-DCC (Eq. (10)) is used to re-transform the predicted ISF glucose concentration to the blood glucose value. This process is repeated till each data point is used once as the validation data. The resultant blood glucose estimates are compared with the actual blood glucose values to give the root-mean-squared error of cross-validation (RMSECV). The whole procedure is iterated for appropriate ranges of $\alpha$ (0 to 20 min) and number of loading vectors (LV) (2 to 10) to determine the optimal combination of parameters ($\alpha_{opt}$, $LV_{opt}$) that yields the minimum RMSECV. This combination of parameters is then used to obtain the PLS regression vector, $b_{opt}$. Prospective prediction on a separate portion of the data set was performed by taking the scalar product of the prediction spectra with $b_{opt}$ (Eq. (8)). The ISF glucose predictions are re-converted to the blood glucose values using PP-DCC, where $\alpha_{opt}$ is used in place of a in Eq. (10). The root-mean-squared error of prediction (RMSEP) is computed from the predicted blood glucose concentrations and the reference blood glucose values.

Conventional PLS calibration and prediction is also performed on the same dataset to compare the relative performance with the DCC model. Twenty simulations are carried out for each value of SNR in the spectral dataset (both calibration and prediction) to establish the mean and standard deviation of the prospective prediction errors.

To investigate the lag time distribution in a human population, clinical datasets consisting of blood glucose concentrations and tissue Raman spectra are used. Raman spectra were collected from the forearms of healthy Caucasian and Asian human subjects undergoing OGTT. The age of the tested human subjects was in the range of 21-29, with a mean of 24.5. For the excitation source, an 830 nm diode laser (Process Instruments) was used at an average power of ~300 mW in a ~1 mm² spot. A f/1.8 spectrograph (Kaiser Optical Systems) was coupled to a liquid nitrogen-cooled CCD (1340×1300 pixels, Roper Scientific) for spectral dispersion and acquisition, respectively. For each volunteer, OGTT was initiated by the ingestion of a glucose-rich solution, and Raman spectra were collected every 5 minutes over a two-hour period. Concurrently, the reference blood glucose concentrations were measured every 10 minutes from blood samples using a clinical glucose analyzer (HemoCue, Inc.), and spline interpolation was used to correlate the measured blood glucose concentrations with the spectra collected at intermediate time points.

Figure 22A:
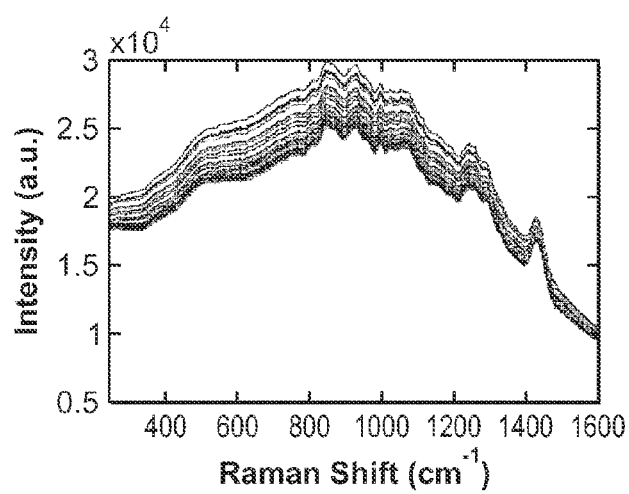
FIGS. 22A and 22B show measured Raman spectra of a human subject and the blood glucose concentration for the same time period.
Figure 22B:
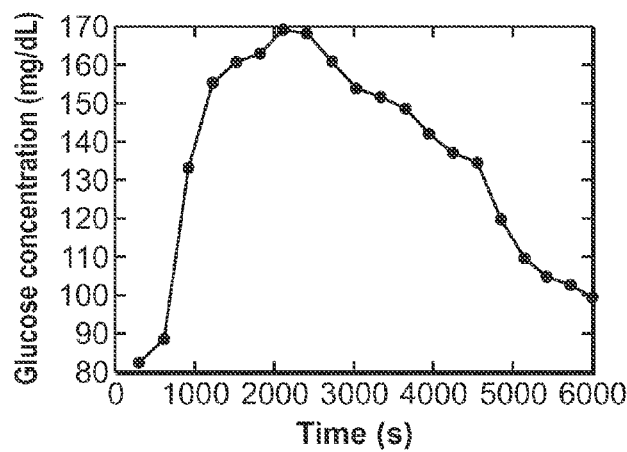

Datasets from volunteers exhibiting motional artifacts, inadequate SNR in the acquired spectra, and impaired glucose tolerance characteristics are excluded from further analysis. A representative set of tissue Raman spectra and the corresponding blood glucose concentration profile acquired from one of the human volunteers are shown in FIGS. 22A and 22B. For the selected volunteer datasets, DCC calibration is performed using a leave-one-out cross-validation routine on the measured Raman spectra and reference blood glucose concentrations to determine the optimal value of α for each individual. In addition, conventional PLS calibration is also performed on the same datasets to compare the resultant cross-validation errors. The cross-validation procedures in both cases remain the same as that described previously, except that experimentally measured Raman spectra are used in place of the simulated Raman spectra. The mean and standard deviation of α determined from the human subjects are used to approximate $\alpha_{actual}$ and $\Delta\alpha$ for the quantification of uncertainty due to physiological lag for the DCC and conventional calibration schemes respectively. These uncertainty estimates are also compared with the spectroscopic uncertainty, $\Delta c_s$.

Figure 23:
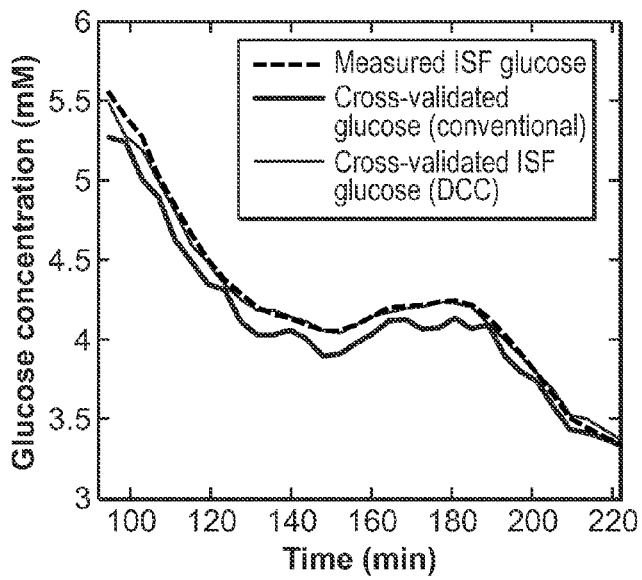
FIG. 23 illustrates cross validated results of glucose measurements overtime.

Numerical simulations were used to compare the prospective prediction capability of the conventional and DCC calibration models. DCC implementation was found to reduce the RMSECV of the simulated dataset from 0.15 mM to 0.04 mM, when the measured ISF glucose concentrations were used for computing the cross validation errors. These simulation results were obtained for a SNR of 40 dB. This result is represented in FIG. 23, where the measured ISF glucose concentrations are plotted together with cross-validated glucose concentrations from the conventional and DCC calibration models. It is evident that the ISF glucose concentration profile generated with DCC closely matches the measured ISF glucose concentrations, while that generated without DCC shows significantly larger deviations. The cross-validation routine also optimized the lag time constant for the DCC calibration model and the number of loading vectors for both models. For this dataset, the characteristic lag time constant $\alpha_{opt}$ was determined to be 6.1 minutes, in agreement with the experimentally observed values of 6-8 minutes.

Figure 24:
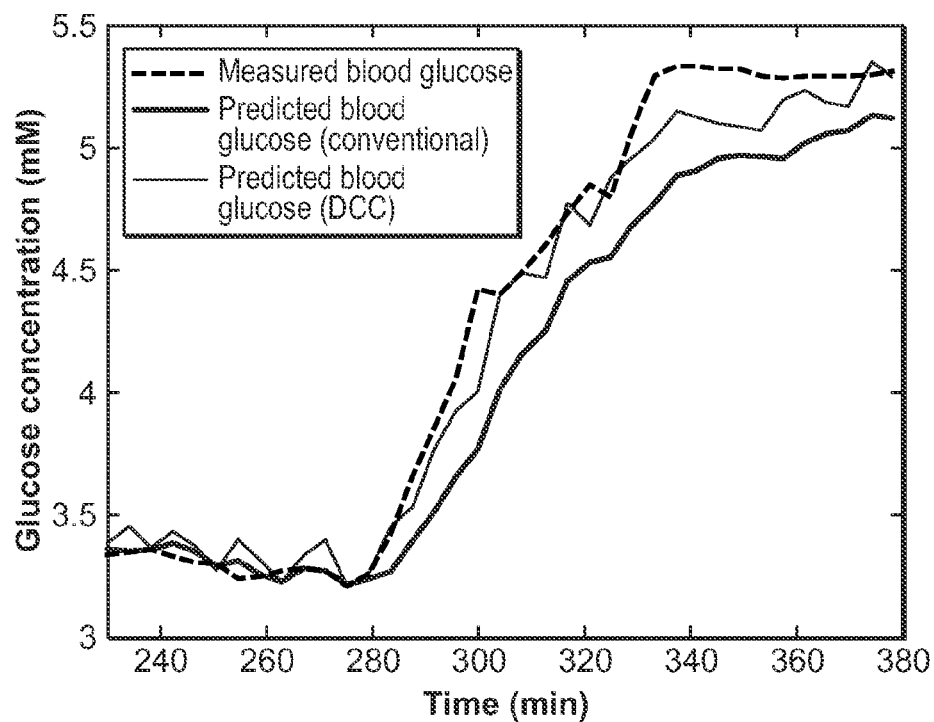
FIG. 24 illustrates prospective prediction results.

When the calibration models were applied prospectively to the prediction dataset, the DCC model (RMSEP=0.14 mM) exhibited significantly improved prediction accuracy compared with the conventional PLS scheme (RMSEP=0.28 mM). FIG. 23 shows the results of prospective prediction, in which the measured blood glucose concentration profile is plotted alongside of the prediction profiles, with and without DCC. This demonstrates how calibration during non-equilibrium conditions leads to systematic errors giving rise to much higher prediction errors (FIG. 24) than estimated during cross-validation (FIG. 23). In fact, in the presence of such errors, the predicted glucose concentration may have no statistically significant correlation with the actual glucose concentrations during rapidly rising and declining glucose concentrations. An even closer correlation with the measured blood glucose concentration profile can be done by smoothing out the noisy fluctuations observed in the concentration profile of the DCC prediction of FIG. 24. However, such smoothing methods were not employed as they might introduce artifacts and additional delays to the concentration profile that are unrelated to glucose equilibration.

Figure 25:
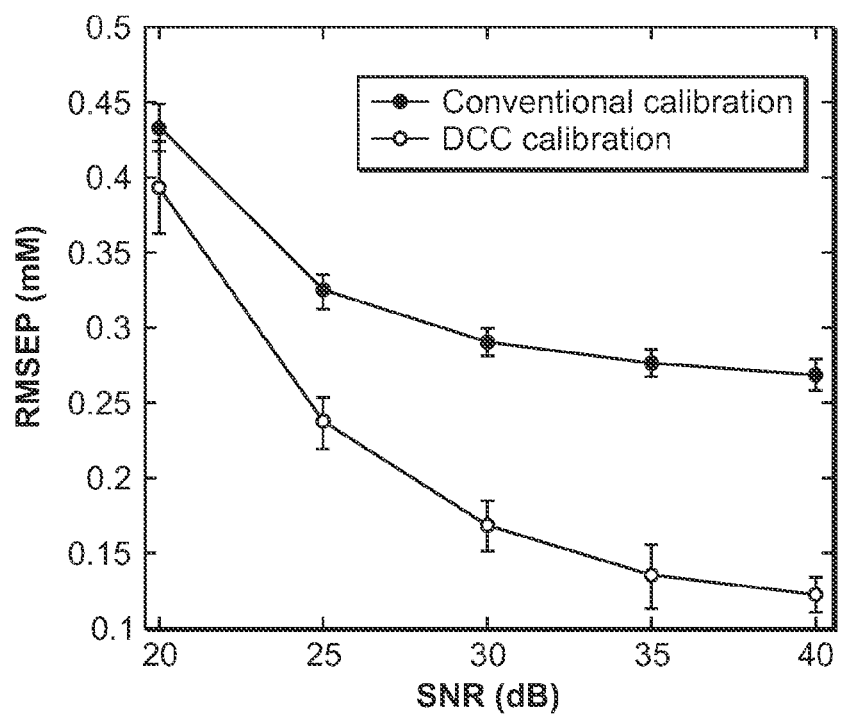
FIG. 25 graphically illustrates RMSEP as a function of SNR.

The accuracy of blood glucose concentration prediction with and without DCC was also compared at varying levels of SNR in the spectral dataset. FIG. 25 shows a plot of the RMSEP of blood glucose prediction with conventional and DCC calibration models as a function of SNR. In both cases, increase in noise level corresponded to an increase in error values, as expected. However, under all tested values of SNR, the prediction error of DCC calibration models was consistently smaller compared to that of the conventional PLS models.

Clearly for DCC implementation, a time series of glucose measurements (such as those obtained from glucose tolerance tests) are required from human subjects included in the calibration study for characterization of the glucose kinetics. It is not possible to develop a consistent calibration model based only on single spectroscopic measurements from multiple human subjects, as such measurements do not provide information on the glucose kinetics.

It is also worth noting that application of an enhanced calibration scheme, such as support vector machines or hybrid calibration methods, alone would not alleviate inconsistencies in the calibration models as they do not address the lack of one-to-one correspondence between the ISF and blood glucose concentrations (FIG. 21). Nevertheless, when used in conjunction with DCC, such calibration schemes may potentially further improve the prediction accuracy.

Table 5 lists the results of the leave-one-out cross-validation on the dataset from each human subject, using DCC calibration as well as the conventional PLS routine. Note that, on average, the RMSECV for the blood glucose concentrations of the human subjects reduces on application of DCC by 15.5%, with a maximum reduction of 28.6%. This demonstrates the applicability of DCC in clinical situations, where the number of tissue components probed is vastly greater than the three constituents (glucose, creatinine and urea) employed in simulations.

TABLE 5

Summary of cross-validation results of conventional and DCC calibration models applied on the human volunteer data.

| Volunteer | No. of data points | DCC Model α_opt (min) | DCC Model RMSECV (mM) | Conventional Model RMSECV (mM) | % change in RMSECV |
|---|---|---|---|---|---|
| 1 | 25 | 9.5 | 0.87 | 1.07 | 19.10 |
| 2 | 26 | 11.5 | 0.52 | 0.72 | 27.56 |
| 3 | 26 | 10.5 | 0.70 | 0.97 | 28.62 |
| 4 | 30 | 11.1 | 1.02 | 1.08 | 5.74 |
| 5 | 25 | 8.4 | 0.68 | 0.79 | 13.35 |
| 6 | 26 | 8.4 | 0.64 | 0.82 | 22.00 |
| 7 | 25 | 7.5 | 0.42 | 0.51 | 17.61 |
| 8 | 29 | 8.1 | 0.76 | 0.87 | 12.44 |
| 9 | 31 | 8.3 | 0.96 | 1.00 | 3.41 |
| 10 | 27 | 12 | 0.50 | 0.53 | 5.25 |

As mentioned, in formulating DCC, it has been assumed that the sampling volume is a subset of the interstitial fluid space. This assumption was based on: (i) NIR light has a penetration depth of ~1 mm in skin tissue and (ii) the blood vessels contribute only 5% to the total skin volume,[36] with the outermost epidermis being completely avascular. However, a small fraction of the inelastically scattered (Raman) light arises from the glucose residing in the blood compartment. This results in a reduction in the value of the lag time constant α, as determined by DCC model. Nevertheless, results demonstrate that DCC successfully models the clinical human volunteer data, even though a small Raman contribution from the blood glucose component is present. This shows that the DCC approach is effective in improving consistency in the calibration model and thus in prospective prediction, as long as the spectral contribution of blood glucose is small compared to that of ISF glucose.

The results also suggest that the value of the lag time is fairly constant for the tested human volunteer population. This is established by the lag time distribution obtained from the clinical data, where the mean of α, 9.5 min, is significantly larger than the standard deviation, 1.6 min. The relative constancy of α indicates that the mean lag time of the calibration set provides a fairly accurate approximation to the lag time of any prospective subject, on whom the method has not been applied before. Thus, the present invention can include the measurement of the lag time distribution in a human population by optical methods. Previous attempts with subcutaneous amperometric sensors have been observed to have significant sensor specific lag, which obscures the precision of the physiological lag measurements. In addition to the sensor specific lag of the sub-cutaneous amperometric monitors, the difference in lag time constants observed from the numerical simulations using the Steil dataset (6.1 min) and clinical studies on human subjects (9.5±1.6 min) can be attributed to: (a) the difference in the composition of glucose (i.e. the proportion of blood and ISF) sampled by the spectroscopic and amperometric sensors and (b) the variations in the population demographics studied in the two cases.

Thus, the measurement of human subjects indicates a reasonably constant value of α, however, there is some indication that the response times between blood and ISF glucose may be different for the rising and falling phases. It has been asserted that ISF glucose falls in advance of blood glucose during the time of declining glucose levels. In such situations, a modified DCC model can be implemented by employing two distinct α's during the rising and falling phases through a piece-wise application of Eq. (10) and (11).

The mean and standard deviation of α obtained on the human volunteer dataset were also employed in determining the physiological lag uncertainties for the DCC and conventional calibration schemes. For the conventional schemes, the uncertainty is calculated as $$\alpha_{actual} \frac{dc_{ISF}}{dt},$$

where the mean α of the human volunteers is used for $\alpha_{actual}$. At times of reasonably rapid increase in glucose levels, the concentration of glucose in either compartment may change by ~2 mg/dL/min (0.11 mM/min). Inserting in these values, for conventional calibration, the prediction uncertainty due to lag amounts to approximately 1.06 mM. For the DCC model, the uncertainty due to lag can be computed by $$\Delta\alpha \frac{dc_{ISF}}{dt},$$

where $\Delta\alpha$ is approximated by the standard deviation of α obtained from the human volunteer dataset. Based on this value of $\Delta\alpha$, a lag uncertainty of 0.18 mM can occur for the DCC calibration method. The calculated values project to an approximately six-fold reduction in the lag uncertainty on application of DCC.

Previously, using tissue phantom studies it has been estimated that the spectroscopic uncertainty for glucose using Raman instrument was 1.04 mM (obtained for σ=61.03 (photon counts), $s_g$=83.74 (photon counts/mM) and olf$_g$=1.43 in Eq. (15)). Prior to this work, this spectroscopic uncertainty was considered to be the limit of detection, i.e. the smallest concentration at which glucose could be detected in the tissue. For the specific case of non-invasive glucose detection this does not provide the full picture, as it ignores the lag uncertainty. For example, when conventional calibration schemes are employed, results suggest that the uncertainty due to lag (1.06 mM) is comparable to the spectroscopic uncertainty (1.04 mM), especially at times of rapid changes in glucose levels. Consequently, the resultant limit of detection, which is sum of the uncertainties arising from spectroscopic considerations and physiological lag (2.1 mM), may be nearly twice that of the previously accepted value (1.04 mM). On the other hand, the net uncertainty on application of DCC (1.22 mM) predominantly arises from spectroscopic considerations (SNR and spectral overlap) and the glucose kinetics plays only a minor role.

The claims should not be read or limited to the described order or elements unless stated to that effect. Therefore, all embodiments that come within the scope and spirit of the following claims and equivalents thereto are claimed as the invention.

What is claimed is:

1. A method for measuring glucose concentration in a patient comprising:
   illuminating a region of tissue with light including a plurality of sequential illumination wavelengths;
   detecting Raman shifted light from the tissue with a detector in response to the plurality of sequential illumination wavelengths of light;

determining, with a data processor, a subset of the sequential illumination wavelengths using error minimization to define a plurality of separated spectral illumination bands, each spectral illumination band including a plurality of different illumination wavelengths, the determining step including processing the detected Raman shifted light to determine the illumination wavelengths of the plurality of separated spectral illumination bands;

subsequently, illuminating a region of tissue in the patient, the region of tissue having a glucose concentration to be measured, with illuminating light having the plurality of different illumination wavelengths within each of the plurality of separated spectral illumination bands;

detecting light from the tissue with the detector in response to the plurality of separated spectral illumination bands of light, the detector generating Raman spectral data; and analyzing the Raman spectral data with the data processor to determine a concentration of glucose in the region of tissue in the patient.

2. The method of claim 1 further comprising illuminating the tissue with a fiber optic probe having an optical concentrator.

3. The method of claim 2 wherein the optical concentrator comprises a compound parabolic concentrator.

4. The method of claim 2 wherein the optical concentrator comprise a compound hyperbolic concentrator.

5. The method of claim 1 further comprising illuminating the region of tissue with a fiber optic probe having a light delivery fiber and a plurality of light collection optical fibers, the light delivery fiber having a first light filter and the plurality of light collection optical fibers having a second filter.

6. The method of claim 1 further comprising using a light source that emits illuminating light that illuminates the region of tissue with the plurality of separated bands having at least 300 spectral points and less than 900 spectral points.

7. The method of claim 1 further comprising using a illumination light filter that defines the separated spectral illumination bands.

8. The method of claim 1 wherein the determining steps further comprises processing spectral data to select the plurality of illumination bands.

9. The method of claim 8 wherein the processing step comprises using a nonlinear representation of spectral data to select the plurality of Raman spectral regions.

10. The method of claim 8 wherein the nonlinear representation comprises support vector regression.

11. The method of claim 8 further comprising forming a regression vector to determine glucose concentration.

12. The method of claim 9 wherein the step of using a non-linear representation comprises a physiological lag component of a glucose concentration measurement.

13. The method of claim 9 wherein the step of using a non-linear representation comprises a tissue turbidity component.

14. The method of claim 1 further comprising detecting the plurality of Raman spectral regions with a single photodetector.

15. The method of claim 1 wherein the plurality of sequential illumination wavelengths comprises a moving window of illumination wavelengths that sequentially illuminates the region of tissue over an infrared spectral range.

16. The method of claim 1 wherein the determining step further comprises determining an error value for each of a plurality of spectral points and selecting the plurality of separated spectral illumination bands from the error values.

17. A portable device for measuring glucose within a body comprising:
a handheld glucose measurement device including:
a light source system in the device that illuminates a region of tissue with a plurality of separated wavelength bands with at least 300 spectral points of illumination;
an optical system in the device that delivers and collects light from the region of tissue in response to the illuminating light;
a detector in the device that detects a plurality of separated spectral regions of Raman shifted a light collected by the optical system in response to each of the at least 300 spectral points of illumination, the detector generating Raman spectral data;
a data processor in the device, the data processor being connected to the detector, the data processor being configured to process the Raman spectral data using a calculated error value to select a subset of the at least 300 spectral points of illumination and process the Raman spectral data associated with the selected subset of spectral points to determine a glucose level within the region of tissue.

18. The device of claim 17 wherein the light source system comprises a tunable laser.

19. The device of claim 17 wherein the light source system further comprises an acousto optic modulator to control the wavelength of illuminating light.

20. The device of claim 17 further comprising a phase modulator.

21. The device of claim 17 wherein the detector comprises a photodetector.

22. The device of claim 17 further comprises the data processor processes Raman spectral data to determine an increase or decrease in glucose concentration.

23. The device of claim 22 wherein the processor is programmed to apply a non-linear representation to the data.

24. The device of claim 23 wherein the representation comprises support vector regression.

25. The device of claim 17 wherein the detector comprises a tunable filter.

26. The device of claim 17 further comprising a compound optical concentrator coupled to a fiber optic device.

27. The device of claim 17 further comprising a control circuit connected to the light source system to control a sequence of illuminating wavelengths of light within the separated wavelength bands.

28. The device of claim 17 further comprising an adjustable filter that filters light incident on the detector having a wavelength outside of a separated spectral region at a selected time.

29. The device of claim 17 wherein the calculated error comprises a root mean squared error value at each spectral point.

30. A handheld Raman diagnostic device comprising:
a handheld unit having a laser light source system, a data processor and a detector system, the laser light source system configured to emit light at a plurality of different illumination wavelengths wherein the detector system detects Raman scattered light from a region of interest in a portion of tissue of a patient and wherein the device operates the laser light source to emit a plurality of illumination spectral bands, each spectral band having a plurality of separated illumination wavelengths that are optically coupled to the region of interest, the detector system configured to detect Raman light from the region of interest and to generate Raman spectral data at a plurality of Raman shifted wavelengths in response to each of the plurality of separated Illumination wavelengths in the plurality of illumination spectral bands wherein the data processor is configured to select, using error minimization, the plurality of illumination spectral bands from the plurality of different illumination wavelengths and to process the Raman spectral data to determine a glucose level in the region of interest.

31. The device of claim 30 further comprising a filter device that filters light from the region of interest to transmit selected Raman spectral detection bands.

32. The device of claim 30 further comprising a fiber optical probe connected to the handheld unit.

33. The device of claim 30 further comprising a control circuit connected to the light source system to control sequential transmission of illuminating light at the plurality of separated spectral bands with at least 300 spectral points of illumination.

34. The device of claim 30 wherein the device has a weight of less than 10 pounds and the processor is programmed to control actuation of the light source system in combination with control of the detector system.

35. The device of claim 30 further comprising a compound parabolic concentrator.

36. The device of claim 30 further comprising a compound of hyperbolic concentrator.

37. The device of claim 30 further comprising an acousto-optic tunable filter.

38. The device of claim 30 wherein the processor is programmed to compute a regression vector to determine glucose concentration.

39. The device of claim 30 further comprising a filter device that filters light incident on the detector.

40. The device of claim 30 wherein the detector system comprises a photodiode.

41. The device of claim 30 wherein the light source system comprises a diode laser.

42. The device of claim 30 wherein the device comprises a body worn device.

43. The device of claim 30 wherein the each spectral band that illuminates the region of interest comprises at least a full width at half maximum of 4 $cm^{-1}$.

* * * * *